United States Patent
Kakkis

(10) Patent No.: US 9,554,987 B2
(45) Date of Patent: *Jan. 31, 2017

(54) METHODS AND FORMULATIONS FOR TREATING SIALIC ACID DEFICIENCIES

(71) Applicant: ULTRAGENYX PHARMACEUTICAL INC., Novato, CA (US)

(72) Inventor: Emil Kakkis, Novato, CA (US)

(73) Assignee: ULTRAGENYX PHARMACEUTICAL INC., Novato, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/745,106

(22) Filed: Jan. 18, 2013

(65) Prior Publication Data

US 2013/0225513 A1 Aug. 29, 2013

Related U.S. Application Data

(63) Continuation-in-part of application No. 13/810,068, filed as application No. PCT/US2011/043910 on Jul. 13, 2011.

(60) Provisional application No. 61/363,995, filed on Jul. 13, 2010, provisional application No. 61/588,069, filed on Jan. 18, 2012, provisional application No. 61/709,549, filed on Oct. 4, 2012.

(51) Int. Cl.

| A61K 9/00 | (2006.01) |
|---|---|
| A61K 31/7012 | (2006.01) |
| A61K 9/20 | (2006.01) |
| A61K 31/335 | (2006.01) |
| A61K 31/35 | (2006.01) |
| A61K 9/48 | (2006.01) |

(52) U.S. Cl.

CPC .......... *A61K 9/0002* (2013.01); *A61K 9/2031* (2013.01); *A61K 9/2054* (2013.01); *A61K 9/2063* (2013.01); *A61K 31/7012* (2013.01); *A61K 9/20* (2013.01); *A61K 9/2004* (2013.01); *A61K 9/48* (2013.01); *A61K 31/335* (2013.01); *A61K 31/35* (2013.01)

(58) Field of Classification Search

None

See application file for complete search history.

(56) References Cited

U.S. PATENT DOCUMENTS

| 4,698,332 | A | 10/1987 | Ogasawara et al. |
|---|---|---|---|
| 5,624,677 | A | 4/1997 | El-Rashidy et al. |
| 5,747,475 | A | 5/1998 | Nordquist et al. |
| 6,444,649 | B1 | 9/2002 | Inamori et al. |
| 8,524,772 | B2 | 9/2013 | Arad et al. |
| 8,840,926 | B2 | 9/2014 | Kaskkis et al. |
| 2004/0192642 | A1 | 9/2004 | Yang et al. |
| 2008/0085306 | A1 | 4/2008 | Nangia et al. |
| 2008/0260824 | A1 | 10/2008 | Nangia et al. |
| 2010/0159001 | A1 | 6/2010 | Cardinal et al. |
| 2010/0160363 | A1 | 6/2010 | Cardinal et al. |
| 2010/0226855 | A1 | 9/2010 | Nangia et al. |
| 2012/0264928 | A1* | 10/2012 | Noguchi et al. ........... 536/53 |
| 2013/0109637 | A1 | 5/2013 | Kakkis et al. |
| 2013/0122094 | A1 | 5/2013 | Kakkis |
| 2013/0273160 | A1 | 10/2013 | Kakkis |
| 2015/0038693 | A1 | 2/2015 | Kakkis et al. |

FOREIGN PATENT DOCUMENTS

| EP | 2332552 | 6/2011 |
|---|---|---|
| WO | WO 2004/000366 | 12/2003 |
| WO | WO 2006/096161 | 9/2006 |
| WO | WO 2008/150477 | 12/2008 |
| WO | WO 2009/032605 | 3/2009 |
| WO | WO 2010/131712 | 11/2010 |
| WO | WO 2012/009474 | 1/2012 |
| WO | WO 2013/063149 | 5/2013 |
| WO | WO 2013/109906 | 7/2013 |

OTHER PUBLICATIONS

Vippagunta et al, "Crystalline Solids", Advanced Drug Delivery Reviews, vol. 48, pp. 3-26 (2001).*
Gavezzotti, "Are Crystal Structures Predictable?", Accounts of Chemical Research, vol. 27, pp. 309-314 (1994).*
Office Action for U.S. Appl. No. 13/659,550, mailed Oct. 7, 2013.
International Search Report for International Application No. PCT/US2012/061737, mailed Mar. 15, 2013.
Office Action for Australian Application No. 2011279158, dated Oct. 23, 2013.
Supplementary European Search Report for European Application No. 11807478, mailed Dec. 5, 2013.
Office Action for U.S. Appl. No. 13/659,540, mailed Dec. 19, 2013.
International Search Report and Written Opinion for International Application No. PCT/US2011/043910, mailed Oct. 18, 2011.
Aich, U. et al, "Development of Delivery Methods for Carbohydrate-based Drugs: Controlled Release of Biologically-Active Short Chain Fatty Acid-Hexosamine Analogs," Glycoconjugate Journal, 27(4):445-459 (2010).
Allevi, P. et al., "Chemoselective synthesis of sialic acid 1,7-lactones," J. Org. Chem., 75(16):5542-5548 (2010).
Argov, Z. et al., "Hereditary inclusion body myopathy. The Middle Eastern genetic cluster," Neurology, 60(9):1519-1523 (2003).
Askanas, V. et al., "Sporadic inclusion-body myositis and hereditary inclusion-body myopathies: current concepts of diagnosis and pathogenesis," Curr. Opin. Rheumatol., 10:530-542 (1998).
Broccolini, A. et al., "Novel GNE mutations in Italian families with autosomal recessive hereditary inclusion-body myopathy," Human Mutation, 23(6):632 (2004).
Rezende, M. C. et al., "A facile route to 9-phosphorylated neuraminic acid derivatives," Synthetic Communications, 28(23):4393-4400 (1998).
Colombo, R. et al., "The first synthesis of N-acetylneuraminic acid 1,7-lactone," Chem. Commun., 43:5517-5519 (2008).
Eisenberg, I. et al., "The UDP-N-acetylglucosamine 2-epimerase/N-acetylmannosamine kinase gene is mutated in recessive hereditary inclusion body myopathy," Nat. Genet., 29(1):83-87 (2001).
Frost, R. A. et al., "Regulation of insulin-like growth factor-I in skeletal muscle and muscle cells," Minerva Endocrinol., 28(1):53-73 (2003).
Galeano, B. et al., "Mutation in the key enzyme of sialic acid biosynthesis causes severe glomerular proteinuria and is rescued by N-acetylmannosamine," The Journal of Clinical Investigation, 117(6):1585-1594 (2007).
Jay, C. M. et al., "Hereditary Inclusion Body Myopathy (HIBM2)," Gene Regulation and Systems Biology, 3:181-190 (2009).
Malicdan, M. C. V. et al., "Prophylactic treatment with sialic acid metabolites precludes the development of the myopathic phenotype in the DMRV-hIBM mouse model," Nature Medicine, 15(6):690-695 (2009).
Nishino, I. et al., "Distal myopathy with rimmed vacuoles is allelic to hereditary inclusion body myopathy," Neurology, 59:1689-1693 (2002).
Nishino, I. et al., "Muscular dystrophies," Current Opinion in Neurology, 15:539-544 (2002).

(Continued)

*Primary Examiner* — James Rogers
(74) *Attorney, Agent, or Firm* — Cooley LLP

(57) ABSTRACT

The present invention relates to compositions and methods for treating sialic acid deficiencies comprising extended release formulations.

22 Claims, 29 Drawing Sheets

(56) References Cited

OTHER PUBLICATIONS

Noguchi, S. et al., "Reduction of UDP-N-acetylglucosamine 2-Epimerase/N-Acetylmannosamine Kinase Activity and Sialylation in Distal Myopathy with Rimmed Vacuoles," The Journal of Biological Chemistry, 279(12):11402-11407 (2004).

Oetke, C. et al., "Evidence for efficient uptake and incorporation of sialic acid by eukaryotic cells," European Journal of Biochemistry, 268(16):4553-4561 (2001).

Oetke, C. et al., "Versatile Biosynthetic Engineering of Sialic Acid in Living Cells Using Synthetic Sialic Acid Analogues," The Journal of Biological Chemistry, 277:6688-6695 (2002).

Penner, J. et al., "Influence of UDP-GlcNAc 2-Epimerase/ManNAc Kinase Mutant Proteins on Hereditary Inclusion Body Myopathy," Biochemistry, 45:2968-2977 (2006).

Pubchem Compound Database, CID 440962, "N-acetylneuraminate 9-phosphate," Created on Date: Jun. 24, 2005, 5 pages.

Ricci, E. et al., "NCAM is hyposialylated in hereditary inclusion body myopathy due to GNE mutations," Neurology, 66:755-758 (2006).

Rota, P. et al., "General and chemoselective N-transacylation of secondary amides by means of perfluorinated anhydrides," Angewandte Chemie International Edition, 49(10):1850-1853 (2010).

Seppala, R. et al., "Mutations in the Human UDP-N-Acetylglucosamine 2-Epimerase Gene Define the Disease Sialuria and the Allosteric Site of the Enzyme," Am. J. Hum. Genet., 64:1563-1569 (1999).

Sparks, S. E. et al., "Use of a cell-free system to determine UDP-N-acetylglucosamine 2-epimerase and N-acetylmannosamine kinase activities in human hereditary inclusion body myopathy," Glycobiology, 15(11):1102-1110 (2005).

Wajnrajch, M. P., "Physiological and Pathological Growth Hormone Secretion," Journal of Pediatric Endocrinology & Metabolism, 18(4):325-338 (2005).

Supplementary Partial European Search Report for European Application No. 12843460.2, mailed Feb. 25, 2015, 6 pages.

Supplementary European Search Report for European Application No. 12843460.2, mailed Aug. 12, 2015, 14 pages.

Supplementary European Search Report for European Application No. 13739040.7, mailed Aug. 4, 2015, 8 pages.

Dufner, G. et al., "Base- and Sugar-Modified Cytidine Monophosphate N-Acetylneuraminic Acid (CMP-Neu5Ac) Analogues—Synthesis and Studies with α(2-6)-Sialyltransferase from Rat Liver," European Journal of Organic Chemistry, 2000(8):1467-1482 (Apr. 2000).

Horn, E. J. et al., "Investigation into an efficient synthesis of 2,3-dehydro-N-acetyl neuraminic acid leads to three decarboxylated sialic acid dimers," Carbohydrate Research, 343(5):936-940 (2008).

Liu, J. L-C et al., "Overproduction of CMP-Sialic Acid Synthetase for Organic Synthesis," J. Am. Chem. Soc., 114(10):3901-3910 (1992).

Martin, R. et al., "The synthesis and enzymatic incorporation of sialic acid derivatives for use as tools to study the structure, activity, and inhibition of glycoproteins and other glycoconjugates," Bioorganic & Medicinal Chemistry, 6(8):1283-1292 (1998).

Nishino, I., "Development of a Fundamental Therapy for Distal Myopathy with Rimmed Vacuoles," Research Report Summary, Heisei 19 Soukatsu / Buntan Kenkyu Houkokusho, pp. 1-7 (2008) (with English Abstract).

Sato, S. et al., "Studies on sialic acids. XIV. Lactone derivatives of N-Acetylneuraminic acid," Chemical & Pharmaceutical Bulletin, 36(12):4678 (1988).

International Preliminary Report on Patentability for International Application No. PCT/US2012/061737, dated Apr. 29, 2014, 9 pages.

International Preliminary Report on Patentability for International Application No. PCT/US2011/043910, dated Jan. 15, 2013, 8 pages.

International Preliminary Report on Patentability for International Application No. PCT/US2013/022167, dated Jul. 22, 2014, 4 pages.

* cited by examiner

Particle Size Distribution of Un-sieved Sialic Acid

Particle Size distribution Plot for ProCR Sialic Acid, 250 Final Blends

Dissolution Plot of Sialic Acid 250 and 325mg SR Tablets by Direct Compression

Dissolution Profile of Sialic Acid 325 and 500 mg SR Tablets Uncoated

Dissolution Profile of Sialic Acid 325mg and 500mg SR Tablets (Coated), Initial Stability

Dissolution Profile of ManNAc 325mg Tablets

ManNAc (325 mg Tabs)

| Sample # | Lots: | | Comments | |
|---|---|---|---|---|
| 1,2,3,4,5,6 | 11216-062 | ALJ684 | ManNAc | |

Dissolution Profile

Date Tested: 15Jun2011
DissolutionConditions
Sample Volume: 900 mL
Apparatus: USP 1 (Baskets)
Dissolution Medium: 50 mM Phosphate, pH 6.8
Basket Speed: 100 rpm
Pull Volume: 10 mL (No replenishment)
Temperature: 37C

| Sample | Time (hours) Dissolved (%LC) | | | | | |
|---|---|---|---|---|---|---|
| | 2 | 4 | 6 | 8 | 12 | 24 |
| 1 | 32 | 51 | 66 | 77 | 89 | 95 |
| 2 | 32 | 52 | 68 | 78 | 90 | 97 |
| 3 | 33 | 53 | 68 | 79 | 90 | 95 |
| 4 | 33 | 52 | 67 | 78 | 91 | 97 |
| 5 | 31 | 51 | 66 | 76 | 87 | 94 |
| 6 | 32 | 51 | 66 | 76 | 87 | 94 |
| Mean | 32 | 52 | 67 | 77 | 89 | 95 |
| %RSD | 1.5 | 1.5 | 1.7 | 1.8 | 1.6 | 1.5 |

Individual Concentrations of Sialic Acid versus Time in Beagle Dog Serum Following IV or Oral Administration

FIGURES 24A-F

METHODS AND FORMULATIONS FOR TREATING SIALIC ACID DEFICIENCIES

CROSS-REFERENCE TO RELATED APPLICATIONS

This application claims the benefit of priority of U.S. Provisional Application No. 61/588,069, filed on Jan. 18, 2012 and entitled "Methods and Formulations for Treating Sialic Acid Deficiencies", and U.S. Provisional Application No. 61/709,549, filed on Oct. 4, 2012 and entitled "Methods and Formulations for Treating Sialic Acid Deficiencies". This application is also a continuation-in-part application of U.S. patent application Ser. No. 13/810,068, filed on Jan. 14, 2013, which is a national stage application of International Application No. PCT/US2011/043910, filed on Jul. 13, 2011 and entitled "Methods and Formulations for Treating Sialic Acid Deficiencies", which claims the benefit of priority to U.S. Provisional Patent Application No. 61/363,995, filed on Jul. 13, 2010 and entitled "Method and Formulations for Treating Sialic Acid Deficiencies". The content of these applications are herein incorporated by reference in their entireties for all purposes.

BACKGROUND

Sialic acid (SA) is a sugar with a net negative charge. It is often present on terminating branches of N-glycans, O-glycans, and glycosphingolipids (gangliosides), and occasionally capping side chains of GPI anchors. Sialic acid modification of cell surface molecules plays a role in many biological phenomena such as protein structure stability, regulation of cell adhesion, and signal transduction. Sialic acid deficiency disorders such as Hereditary Inclusion Body Myopathy (HIBM or HIBM type 2), Nonaka myopathy, and Distal Myopathy with Rimmed Vacuoles (DMRV) are clinical diseases resulting from a reduction in sialic acid production.

HIBM is a rare autosomal recessive neuromuscular disorder caused by a biosynthetic defect in the sialic acid synthesis pathway. Eisenberg et al., *Nat. Genet.* 29:83-87 (2001). The disease usually manifests between the ages of 20 to 40 such as foot drop and slowly progressive muscle weakness and atrophy. Patients may suffer difficulties walking with foot drop, gripping, use of hands, and swallowing. The disease is progressive; most afflicted individuals become incapacitated and wheelchair-confined within two to three decades. No treatments are available.

Studies of an Iranian-Jewish genetic isolate mapped the mutation associated with HIBM to chromosome 9p12-13. Argov et al., *Neurology* 60:1519-1523 (2003). The causative mutations were identified for HIBM in the gene GNE, which encodes the bifunctional enzyme UDP-N-acetylglucosamine-2-epimerase/N-acetylmannosamine kinase (GNE/MNK). Eisenberg et al., *Nat. Genet.* 29:83-87 (2001). DMRV is a Japanese variant, allelic to HIBM. Nishino et al., *Neurology* 59:1689-1693 (2002).

The biosynthesis steps and feedback regulation of GNE/MNK is depicted in FIG. 1. The production of sialic acid on glycoconjugates requires the conversion of N-acetylglucosamine (conjugated to its carrier nucleotide sugar UDP) to sialic acid. The sialic acid subsequently enters the nucleus where it is conjugated with its nucleotide sugar carrier CMP to make CMP-sialic acid, which is used as a donor sugar for glycosylation reactions in the cell. CMP-sialic acid is a known regulator of GNE/MNK activity. Jay et al., *Gene Reg. & Sys. Biol.* 3:181-190 (2009). Patients with HIBM have a deficiency in the production of sialic acid by the GNE/MNK enzyme, which is involved in the first two steps of this sequence. Nearly twenty GNE mutations have been reported in HIBM patients from different ethnic backgrounds with founder effects among the Iranian Jews and Japanese. Broccolini et al., *Hum. Mutat.* 23:632 (2004).

Because the production of sialic acid is the key reason the mutation causes the disease, replacing a metabolite after the genetic block in the pathway could, in theory, alleviate symptoms of a sialic acid deficiency. Jay et al., *Gene Reg. and Sys. Biology* 3:181-190 (2009). In practice, however, administering one or more compounds in the sialic acid biosynthetic pathway in vivo is a significant challenge. These compounds have extraordinarily rapid clearance rates and are excreted in the urine before they can be metabolized.

SUMMARY OF THE INVENTION

The present invention provides method for treating a sialic acid deficiency in an individual in need thereof comprising orally administering a sialic acid, or a pharmaceutically acceptable salt, solvate, or ester thereof, wherein the method provides a therapeutically effective amount of sialic acid over a period of greater than about four hours.

In some embodiments of the present invention, the sialic acid, or a pharmaceutically acceptable salt, solvate, or ester thereof, is in an extended release formulation. In some embodiments of the present invention, the sialic acid, or a pharmaceutically acceptable salt, solvate, or ester thereof, is in both an extended release formulation and an immediate release formulation.

In some embodiments of the present invention, the method provides a mean $C_{min}$ sialic acid of at least about 0.11 mcg/ml at steady state during the dosing intervals.

In some embodiments of the present invention, the method provides a mean plasma concentration of sialic acid of at least about 0.16 mcg/ml at steady state during the dosing intervals.

In some embodiments the present invention, the method provides a mean plasma concentration of sialic acid at steady state during the dosing intervals that is at least about 50% higher than the mean plasma concentration of sialic acid in the individual before the administration of the sialic acid, or a pharmaceutically acceptable salt, solvate, or ester thereof.

In some embodiments of the present invention, the method provides an improved absorption profile when the extended release formulation is administered under fed conditions than being administered under fasting conditions.

In some embodiments of the methods, the sialic acid deficiency is a myopathy associated with sialic acid deficiency.

In some embodiments of the methods, the sialic acid deficiency is a myopathy associated with sialic acid deficiency. In some embodiments, the myopathy associated with sialic acid deficiency is Hereditary Inclusion Body Myopathy (HIBM), Nonaka myopathy, and/or Distal Myopathy with Rimmed Vacuoles (DMRV).

In some embodiments of the methods, the extended release formulation is in a solid matrix form.

DETAILED DESCRIPTION

Figure 1:
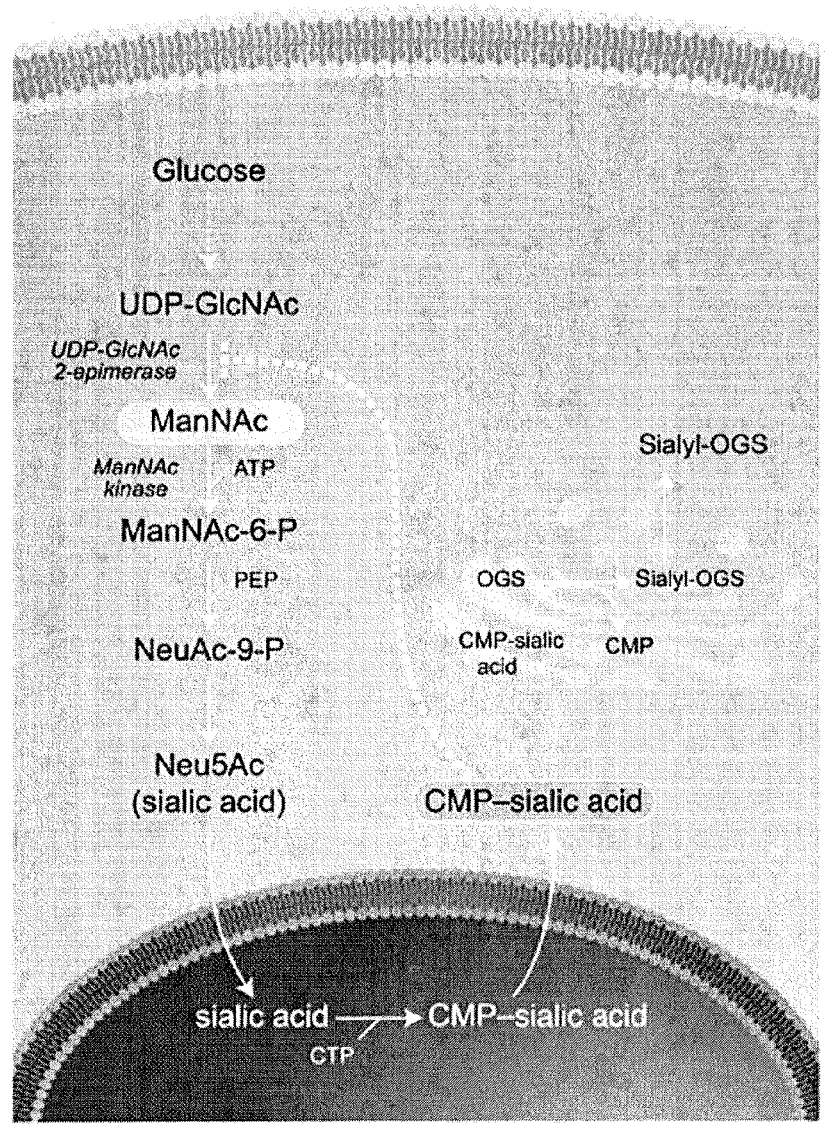
FIG. 1 provides a diagram of intracellular sialic acid metabolism.

The present application provides extended release pharmaceutical formulations comprising one or more compounds in the sialic acid biosynthetic pathway or derivative thereof and methods of treating and preventing sialic acid deficiencies utilizing the extended release pharmaceutical formulations. This invention concerns designing an approach to substrate replacement that provides individuals with sialic acid deficiencies stable and steady day and nighttime replacement without high concentration spikes across a broad range of genotypes and in multiple tissues.

This invention can optimally achieve this substrate replacement and treatment benefit through the combination of using extended release formulations and one or more metabolites, including combinations of metabolites.

It is understood that the description refers to and includes effective amounts of an active agent, such as the compounds provided herein, which include but are not limited to the compounds included under the heading "Therapeutic Agent." Thus, it is understood that any of the extended release formulations detailed herein may comprise an effective amount of a therapeutic agent, such as an effective amount of sialic acid, or a pharmaceutically acceptable salt thereof.

DEFINITIONS

The terms "oral administration" and "oral ingestion" refer to all conventional forms for the oral delivery of a pharmaceutical composition to an individual and that result in the deposition of the pharmaceutical formulation into the gastrointestinal tract (including the gastro portion of the gastrointestinal tract, i.e., the stomach) of the patient. Accordingly, oral administration and oral ingestion include, by way of example, actual ingestion of a solid or liquid pharmaceutical composition, oral gavage, and the like.

The terms "treating" and "treatment" as used herein refer to an approach for obtaining beneficial or desired results including clinical results. For purposes of this invention, beneficial or desired clinical results include, but are not limited to, one or more of the following: decreasing the severity and/or frequency one or more symptoms resulting from the disease, diminishing the extent of the disease, stabilizing the disease (e.g., preventing or delaying the worsening of the disease), delay or slowing the progression of the disease, ameliorating the disease state, increasing production of sialic acid, the sialylation precursor CMP-sialic acid (e.g., increasing intracellular production of sialic acid) and restoring the level of sialylation in muscle and other proteins, decreasing the dose of one or more other medications required to treat the disease, and/or increasing the quality of life. "Treating" a patient with a formulation described herein includes management of an individual to inhibit or cause regression of a disease or condition.

"Prophylaxis" or "prophylactic treatment" "or preventive treatment" refers to prevention of the occurrence of symptoms and/or their underlying cause, for example, prevention of a disease or condition in a patient susceptible to developing a disease or condition (e.g., at a higher risk, as a result of genetic predisposition, environmental factors, predisposing diseases or disorders, or the like). Prophylaxis includes HIBM myopathy in which chronic disease changes in the muscles are irreversible and for which animal model data suggests treatment benefit in prophylaxis.

As used herein, "delaying" the progression of the disease means to defer, hinder, slow, retard, stabilize, and/or postpone development of the disease. This delay can be of varying lengths of time, depending on the history of the disease and/or individual being treated.

As used herein, an "at risk" individual is an individual who is at risk of developing a sialic acid deficiency. An individual "at risk" may or may not have detectable disease, and may or may not have displayed detectable disease prior to the treatment methods described herein. "At risk" denotes that an individual has one or more so-called risk factors, which are measurable parameters that correlate with development of a sialic acid deficiency, which are described herein. An individual having one or more of these risk factors has a higher probability of developing a sialic acid deficiency than an individual without these risk factor(s).

The term "effective amount" refers to the amount of one or more compounds in the sialic acid biosynthetic pathway in a sufficient amount to render a desired treatment outcome. An effective amount may be comprised within one or more doses, i.e., a single dose or multiple doses may be required to achieve the desired treatment endpoint.

A "therapeutically effective amount" refers to an amount of one or more compounds in the sialic acid biosynthetic pathway sufficient to produce a desired therapeutic outcome (e.g., reduction of severity of a disease or condition). In one embodiment, the therapeutically effective amount refers to a therapeutically effective plasma concentration of sialic acid. A "prophylactically effective amount" refers to an amount of a pharmaceutical formulation including one or more compounds in the sialic acid biosynthetic pathway sufficient to prevent or reduce severity of a future disease or condition when administered to an individual who is susceptible and/or who may develop a disease or condition.

The term "extended release" refers to a drug-containing formulation or fraction thereof, in which release of the drug is not immediate, i.e., with an "extended release" formulation, administration does not result in immediate release of the drug into an absorption pool. In general, the term "extended release" as used herein includes controlled release, sustained release, and delayed release formulations.

By "pharmaceutically acceptable" is meant a material that is not biologically or otherwise undesirable, i.e., the material may be incorporated into a pharmaceutical composition administered to a patient without causing any significant undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration.

The term "disorder" or "disease" used interchangeably herein, refers to any alteration in the state of the body or one of its organs and/or tissues, interrupting or disturbing the performance of organ function and/or tissue function (e.g., causes organ dysfunction) and/or causing a symptom such as discomfort, dysfunction, distress, or even death to a subject afflicted with the disease.

The term "individual" or "patient" refers to an animal, for example, a mammal and includes, but is not limited to, human, bovine, horse, feline, canine, rodent, or primate. Preferably, the individual is a human.

The term "derivative" as used herein includes derivatives, analogs, prodrugs, and unnatural precursors.

The term "pharmaceutically acceptable salt" refers to a salt which retains the biological effectiveness of the compound and which is not biologically or otherwise undesirable.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise. It is understood that embodiments, aspects and variations of the invention described herein include "comprising," "consisting" and/or "consisting essentially of" embodiments, aspects and variations.

Pharmacokinetic parameters describe the in vivo characteristics of the active agent, i.e., the free sialic acid over time, such as plasma concentration (C), $C_{max}$, $C_n$, $C_{24}$, $T_{max}$, and AUC. "$C_{max}$" is the measured concentration of the active agent in the plasma at the point of maximum concentration. "$C_n$" is the measured concentration of an active agent in the plasma at about n hours after administration. "$C_{24}$" is the measured concentration of an active agent in the plasma at about 24 hours after administration. The term "$T_{max}$" refers to the time at which the measured concentration of an active agent in the plasma is the highest after administration of the active agent. "AUC" is the area under the curve of a graph of the measured concentration of an active agent (typically plasma concentration) vs. time, measured from one time point to another time point. For example $AUC_{0-t}$ is the area under the curve of plasma concentration versus time from time 0 to time t. The $AUC_{0-\infty}$ or $AUC_{0-INF}$ is the calculated area under the curve of plasma concentration versus time from time 0 to time infinity.

Extended Release Formulations

Provided herein are extended release pharmaceutical formulations comprising as the therapeutic agent one or more compounds in the sialic acid biosynthetic pathway or a derivative thereof or a pharmaceutically acceptable salt of the foregoing. In one embodiment, the extended release pharmaceutical formulations comprise a therapeutic agent as detailed herein and a polymer. An extended release formulation comprising a therapeutic agent and a polymer may further comprise one or more additional components, such as any one or more of a diluent, an excipient, an antioxidant, a lubricant, a colorant, a binder, a disintegrant, and the like. It is understood that reference to and description of extended release pharmaceutical formulations comprising one or more compounds in the sialic acid biosynthetic pathway or a derivative thereof below is exemplary and that this description applies equally to and includes extended release pharmaceutical formulations comprising any one or more compounds in the sialic acid biosynthetic pathway. It is also understood that reference to and description of extended release pharmaceutical formulations comprising any one or more derivatives of compounds in the sialic acid biosynthetic pathway below is exemplary and that this description applies equally to and includes extended release pharmaceutical formulations comprising any one or more derivatives, analogs, prodrugs, and/or unnatural precursor compounds in the sialic acid biosynthetic pathway.

In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents. In another variation, the extended release formulation comprises a prodrug of one or more compounds in the sialic acid biosynthetic pathway such as a prodrug of sialic acid, or a pharmaceutically acceptable salt thereof, as the therapeutic agent. In another variation, the extended release formulation comprises sialic acid, or a pharmaceutically acceptable salt thereof, as the therapeutic agent and further comprises a hydrocolloid polymer, an anionic, pH-dependent gel forming co-polymer and a water swellable, pH independent polymer and optionally further comprises a lubricant and/or an excipient. In a particular variation, the extended release formulation comprises sialic acid, or a pharmaceutically acceptable salt thereof, carrageenan, sodium alginate and either hypromellose or polyethylene oxide. In a further variation, the extended release formulation comprises sialic acid, or a pharmaceutically acceptable salt thereof, carrageenan, sodium alginate, either hypromellose or polyethylene oxide, magnesium stearate and microcrystalline cellulose and colloidal silicon dioxide. In one aspect, the extended release formulation is a formulation of Table E. In yet another aspect, the extended release formulation is a formulation of Table 8. In yet another aspect, the extended release formulation is a formulation of Example 6. In yet another aspect, the extended release formulation is a formulation of Example 7.

Therapeutic Agent

It is believed that administration of sialic acid or a compound in the sialic acid biosynthetic pathway, or a derivative thereof, or a pharmaceutically acceptable salt of any of the foregoing, may be administered as a therapeutic agent (e.g., as substrate replacement) to an individual who has or is suspected of having a sialic acid deficiency disorder. Extended release formulations comprising such compounds, or pharmaceutically acceptable salts thereof, as the therapeutic agent are provided herein. In one aspect, the sialic acid or a compound in the sialic acid biosynthetic pathway, or a derivative thereof, or a pharmaceutically acceptable salt of any of the foregoing, is sialic acid or a pharmaceutically acceptable salt thereof. In one aspect, any of the extended release formulations detailed herein may comprise an effective amount of a therapeutic agent, such as an effective amount of sialic acid or a pharmaceutically acceptable salt thereof.

A compound in the sialic acid biosynthetic pathway or a derivative thereof in one variation is a compound, or pharmaceutically acceptable salt thereof, that is at or downstream from ManNAc in the sialic acid biosynthetic pathway. In a particular variation, the therapeutic agent is a compound, or pharmaceutically acceptable salt thereof, that is at or downstream from ManNAc in the sialic acid biosynthetic pathway and is depicted in FIG. 1.

A compound in the sialic acid biosynthetic pathway or a derivative thereof in another variation is a compound, or a pharmaceutically acceptable salt thereof, that is at or upstream from CMP-sialic acid in the sialic acid biosynthetic pathway. In a particular variation, the therapeutic agent is a compound, or a pharmaceutically acceptable salt thereof, that is at or upstream from CMP-sialic acid in the sialic acid biosynthetic pathway and is depicted in FIG. 1. In one such variation, the compound in the sialic acid biosynthetic pathway or a derivative thereof does not include glucose or a pharmaceutically acceptable salt thereof.

In a particular variation, the compound in the sialic acid biosynthetic pathway or a derivative thereof in one variation is a compound, or a pharmaceutically acceptable salt thereof, that is: (i) at or downstream from ManNAc in the sialic acid biosynthetic pathway, and (ii) is at or upstream from CMP-sialic acid in the sialic acid biosynthetic pathway. In one such variation, the compound is a compound depicted in FIG. 1, or a pharmaceutically acceptable salt thereof.

A compound in the sialic acid biosynthetic pathway or derivative thereof includes, but is not limited to, mannosamine, N-acetyl mannosamine (ManNAc), ManNac-6-phosphate (ManNAc-6-P), UDP-GlcNAc, N-acetylneuraminic acid (NeuAc), NeuAc-9-phosphate (NeuAc-9-P), sialic acid (i.e., 5-N-acetylneuraminic acid), CMP-sialic acid, and/or derivatives thereof or pharmaceutically acceptable salts of the foregoing.

In some embodiments, the one or more compounds in the sialic acid biosynthetic pathway or derivative thereof include N-acetylneuraminic acid (NeuAc) or a derivative thereof. Structures of such NeuAc or derivatives thereof include, but are not limited to, those defined by the formula below:

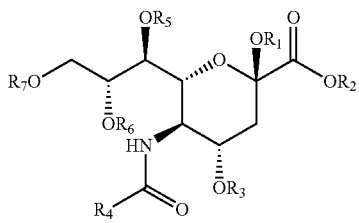

wherein each $R_1$, $R_2$, $R_3$, $R_5$, $R_6$, or $R_7$ is independently hydrogen, lower alkanoyl, carboxylate or lower alkyl; and $R_4$ is lower alkyl, lower alkanoylalkyl or lower alkyl alkanoyloxy.

In some embodiments, the one or more compounds in the sialic acid biosynthetic pathway or derivative thereof include ManNAc or a derivative thereof. Structures of such ManNAc and derivatives thereof include, but are not limited to, those defined by the formula below:

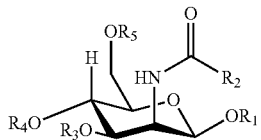

Wherein each $R_1$, $R_3$, $R_4$, or $R_5$ is independently hydrogen, lower alkanoyl, carboxylate or lower alkyl; and $R_2$ is lower alkyl, lower alkanoylalkyl or lower alkyl alkanoyloxy.

The term lower alkyl refers to $(C_1-C_6)$alkyl. A lower alkyl includes methyl, ethyl, propyl, isopropyl, butyl, iso-butyl, sec-butyl, pentyl, 3-pentyl, hexyl as well as $(C_3-C_6)$cycloalkyl moieties (e.g., cyclopropyl, cyclobutyl, cyclopentyl, or cyclohexyl), $(C_3-C_6)$cycloalkyl$(C_1-C_6)$alkyl (e.g., cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl), $(C_1-C_6)$alkoxy (e.g., methoxy, ethoxy, propoxy, isopropoxy, butoxy, isobutoxy, sec-butoxy, pentoxy, 3-pentoxy, or hexyloxy) $(C_2-C_6)$alkenyl (e.g., vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl), $(C_2-C_6)$alkynyl (e.g., ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl), $(C_1-C_6)$ alkanoyl (e.g., acetyl, propanoyl or butanoyl), halo$(C_1-C_6)$ alkyl (e.g., iodomethyl, bromomethyl, chloromethyl, fluoromethyl, trifluoromethyl, 2-chloroethyl, 2-fluoroethyl, 2,2,2-trifluoroethyl, or pentafluoroethyl), hydroxy$(C_1-C_6)$alkyl (e.g., hydroxymethyl, 1-hydroxyethyl, 2-hydroxyethyl, 1-hydroxypropyl, 2-hydroxypropyl, 3-hydroxypropyl, 1-hydroxy butyl, 4-hydroxybutyl, 1-hydroxypentyl, 5-hydroxypentyl, 1-hydroxyhexyl, or 6-hydroxyhexyl), $(C_1-C_6)$ alkoxycarbonyl (e.g., methoxycarbonyl, ethoxycarbonyl, propoxycarbonyl, isopropoxycarbonyl, butoxycarbonyl, pentoxycarbonyl, or hexyloxycarbonyl), $(C_1-C_6)$alkylthio (e.g., methylthio, ethylthio, propylthio, isopropylthio, butylthio, isobutylthio, pentylthio, or hexylthio), and/or $(C_2-C_6)$ alkanoyloxy (e.g., acetoxy, propanoyloxy, butanoyloxy, isobutanoyloxy, pentanoyloxy, or hexanoyloxy).

In some embodiments, $R_2$ is methyl, and each of $R_1$, $R_3$, $R_4$, and $R_5$ is hydrogen. In some embodiments, the ManNAc or derivative thereof is N-acetyl mannosamine (ManNAc). In some embodiments, the ManNAc or derivative thereof is N-levulinoylmannosamine (ManLev) or N-azidoacetylmannosamine (ManNAz).

In one variation, the one or more compounds in the sialic acid biosynthetic pathway or derivative thereof is an ester of a compound in the sialic acid biosynthetic pathway. In one aspect, the one or more compounds in the sialic acid biosynthetic pathway or derivative thereof is an ester of sialic acid or ManNAc. In a particular variation, the one or more compounds in the sialic acid biosynthetic pathway or derivative thereof is an ester of sialic acid. In one aspect, the one or more compounds in the sialic acid biosynthetic pathway or derivative thereof is a prodrug of sialic acid. See also WO 2010/131712, published Nov. 18, 2010, for derivatives of compounds in the sialic acid biosynthetic pathway, which is incorporated herein by reference in its entirety and specifically with respect to compounds (e.g., derivatives of compounds in the sialic acid biosynthetic pathway) detailed therein.

In one aspect, a derivative of one or more compounds in the sialic acid biosynthetic pathway (e.g., a derivative of sialic acid or ManNAc) is an effective substrate replacement for sialic acid, such as in an individual who has or is suspected of having a sialic acid deficiency disorder. A derivative of one or more compounds in the sialic acid biosynthetic pathway (e.g., a derivative of sialic acid or ManNAc), or an extended release formulation comprising a derivative of one or more compounds in the sialic acid biosynthetic pathway (e.g., a derivative of sialic acid or ManNAc) may exhibit any one or more of the following characteristics: (i) capable of delivering to an individual in need thereof a therapeutically effective amount of one or more compounds in the sialic acid pathway or derivatives thereof over a period of about or greater than about any of 8, 9, 10, 11, 12, 13, 14, 15, 16, 17, 18, 19, or 20 hours; (ii) capable of delivering to an individual in need thereof a substantially constant therapeutically effective amount of one or more compounds in the sialic acid pathway or derivatives thereof over a period of about or greater than about any of 8, 9, 10, 11, 12, 13, 14, 15, 16, 17, 18, 19, or 20 hours; (iii) capable of delivering to an individual in need thereof a therapeutically effective amount of one or more compounds in the sialic acid pathway or derivatives thereof with a $T_{max}$ of between about any of 2-6 hours, 2-5 hours, or 3-6 hours during each dosing interval; (iv) capable of delivering to an individual in need thereof a therapeutically effective amount of one or more compounds in the sialic acid pathway or derivatives thereof with a $C_{max}$ of about 0.1-0.9 μg/mL, 0.1-100 μg/mL, 0.2-0.3 μg/mL, or 0.5-100 μg/mL; (v) capable of delivering to an individual in need thereof a therapeutically effective amount of one or more compounds in the sialic acid pathway or derivatives thereof with a trough level of about 0.05-0.2 μg/mL, 0.05-0.3 μg/mL, 0.1-0.3 μg/mL, or 0.1-20 μg/mL; (vi) capable of delivering to an individual in need thereof a therapeutically effective amount of one or more compounds in the sialic acid pathway or derivatives thereof with less than about any of 10%, 20%, 30%, 40%, 50%, 60%, or 70% excreted after one hour; (vii) capable of delivering to an individual in need thereof between about any of 0.01-750 mg/kg/day, 0.5-500 mg/kg/ day, 1-250 mg/kg/day, 2.5-100 mg/kg/day, or 5-50 mg/kg/day of one or more compounds in the sialic acid pathway or derivatives thereof or a pharmaceutically acceptable salt of the foregoing; (viii) capable of delivering to an individual in need thereof between about any of 0.01-750 mg/kg/day, 0.5-500 mg/kg/day, 1-250 mg/kg/day, 2.5-100 mg/kg/day, or 5-50 mg/kg/day of one or more compounds in the sialic acid pathway or derivatives thereof or a pharmaceutically acceptable salt of the foregoing; (ix) has an absolute bioavailability of about 1 to about 50%; (x) has a bioavailability based on sialic acid levels in the urine of about 0.5 to about 100%; and (xi) has a mean residence time (MRT) of at least about 3.5 hours.

In some embodiments, the one or more compounds in the sialic acid biosynthetic pathway or derivative thereof include sialic acid or a derivative thereof. In some embodiments, the sialic acid or derivative thereof is sialic acid. In some embodiments, the sialic acid or derivative thereof is a sialic acid analog such as N-levulinoyl sialic acid (SiaLev) or N-azidoacetyl sialic acid (SiaNAz). In some embodiments, the sialic acid is bound as a glycoconjugate. In some embodiments, the sialic acid or derivative thereof is an unnatural precursor such as sialylactose.

In some embodiments, the extended release formulation comprises about any of one, two, three, or four compounds in the sialic acid biosynthetic pathway or a derivative thereof. In some embodiments, the extended release formulation comprises two compounds in the sialic acid biosynthetic pathway or a derivative thereof. Therefore, for example, the extended release formulation may include ManNAc or a derivative thereof and sialic acid or a derivative thereof. More particularly, the extended release formulation may include ManNAc and sialic acid.

In embodiments of any of the extended release formulations, the amount of one or more compounds in the sialic acid biosynthetic pathway or derivative thereof in the extended release formulation is an amount effective to increase sialic acid production and/or increase sialylation (e.g., maximal restoration of sialylation).

The ratio of the two or more compounds in the sialic acid biosynthetic pathway or derivative thereof, in some embodiments, is a ratio which minimizes feedback inhibition of the sialic acid biosynthetic pathway. In some embodiments, the ratio of the two or more compounds in the sialic acid biosynthetic pathway or derivative thereof is a ratio which allows efficient delivery of the two or more compounds in the sialic acid biosynthetic pathway or derivative thereof to muscle cells. In some embodiments, the ratio of the two or more compounds in the sialic acid biosynthetic pathway or derivative thereof is a ratio which minimizes feedback inhibition of the sialic acid biosynthetic pathway and allows efficient delivery of the two or more compounds in the sialic acid biosynthetic pathway or derivative thereof to muscle cells. In some embodiments, the two or more compounds in the sialic acid biosynthetic pathway or derivative there of are ManNAc or a derivative thereof and sialic acid or a derivative thereof. For example, in some embodiments, the ratio of ManNAc and sialic acid is a ratio which minimizes feedback inhibition of the sialic acid biosynthetic pathway and allows efficient delivery of ManNAc and/or sialic acid to muscle cells. The combination may optimally spread out the replacement of intermediates, enhancing optimal distribution to all cell types with different metabolisms. Methods of testing restoration of sialylation and determining the best ratio of the two or more compounds in the sialic acid biosynthetic pathway or derivative thereof using in vitro HIBM muscle cells are known in the art. See e.g., Noguchi S. et al., *J. Bio. Chem.* 279(12):11402-7 (2004). This may involve evaluating muscle derived proteins for optimal sialylation such as soluble forms of neural cell adhesion molecule (NCAM) (Ricci et al., *Neurology* 66:755-758 (2006), evaluating sialic metabolite or CMP-sialic acid levels in tissue samples, or assessing sialylated proteins on the surface of muscle or other cells. Noguchi S. et al., *J. Bio. Chem.* 279(12):11402-7 (2004).

In embodiments in which the extended release formulation comprises two compounds in the sialic acid biosynthetic pathway or a derivative thereof, the two compounds in the extended release formulation may be present in a weight to weight percentage of between about any of 5%-95%:95%-5%, 5%-50%:95%-50%, or 10%-40%:90%-60%. The two compounds in the extended release formulation may be present in a weight to weight percentage of about any of 90%:10%, 80%:20%, 70%:30%, 60%:40%, 50%:50%, 40%:60%, 30%:70%, 20%:80%, or 10%:90%. In some embodiments, the two compounds in the extended release formulation are in a weight to weight percent of about 50%:50%. In some embodiments, the one or more compounds in the sialic acid pathway or derivatives thereof include ManNAc or a derivative thereof and/or sialic acid or a derivative thereof. Therefore, for example, the extended release formulation may include ManNAc and sialic acid wherein the weight to weight percentage of ManNAc to sialic acid is about any of 90%:10%, 80%:20%, 70%:30%, 60%:40%, 50%:50%, 40%:60%, 30%:70%, 20%:80%, or 10%:90%.

Polymer

The extended release formulations comprising one or more compounds in the sialic acid biosynthetic pathway or a derivative thereof as described herein may include one or more polymers. The polymer may be a natural polymer (e.g., polysaccharide or protein), modified natural polymer, and/or synthetic polymer. The polymer may be, for example, a hydrophobic polymer, hydrophilic polymer, hydrogel, soluble polymer, biodegradable polymer, nonbiodegradable polymer, and/or mucoadhesive polymer.

In some embodiments, the polymer is a hydrophobic polymer. Examples of hydrophobic polymers include polyethylene, polyvinyl chloride, ethyl cellulose or acrylate polymers and their copolymers.

In some embodiments, the polymer is a hydrophilic polymer. Examples of hydrophilic polymers include a) cellulose derivatives such as methylcellulose (MC), hydroxyethyl-cellulose, hydroxypropylmethyl-cellulose (HPMC), or sodium carboxymethylcellulose, b) noncellulose natural or semisynthetic polymers such as agar-agar, carob gum, alginates, molasses, polysaccharides of mannose and galactose, or chitosan and modified starches and c) polymers of acrylic acid such as carbopol polymers.

In some embodiments, the polymer is a hydrogel. Examples of hydrogels include, but are not limited to, polyhydroxyethyle methylacrylate (PHEMA), polyvinyl alcohol (PVA), polyvinyl pyrrolidone (PVP), polyethylene oxide (PEO), or polyacrylamide (PA). In some embodiments, the hydrogel is polyethylene oxide (e.g., Polyox™ water soluble resin, Dow Chemical Company, Mich., USA).

In some embodiments, the polymer is a soluble polymer. Examples of soluble polymers include, but are not limited to, polyethylene glycol (PEG), PVA, PVP, or HPMC.

In some embodiments, the polymer is a biodegradable polymer. Examples of biodegradable polymers include, but are not limited to, polylactic acid (PLA), polyglycolic acid (PGA), poly(lactic/glycolic acid) (PLGA), polycaprolactone (PCL), polyanhydrides, or polyorthoesters.

In some embodiments, the polymer is a nonbiodegradable polymer. Examples of nonbiodegradable polymers include, but are not limited to, polyethylene vinyl acetate, polydimethyl siloxane (PDS), polyether urethane (PEU), polyvinyl chloride (PVC), cellulose acetate (CA), or ethyl cellulose (EC).

In some embodiments, the polymer is a mucoadhesive polymer. Examples of mucoadhesive polymers include, but are not limited to, polycarbophil, sodium carboxymethyl cellulose, polyacrylic acid, tragacanth, methyl cellulose, pectin, natural gums, xanthan gum, guar gum, or karaya gum.

In some embodiments, the extended release pharmaceutical formulation includes two polymers. In some embodiments, the polymer is not polylactide. In some embodiments, the polymer is not a polylactide copolymer such as PLGA.

In some embodiments, the extended release formulation comprises one or more polymers selected from the group consisting of a) a water-swellable, pH independent polymer, b) a anionic, pH-dependent, gel-forming copolymer, c) a cationic polymer, and d) a hydrocolloid polymer. In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents. In another variation, the extended release formulation comprises a prodrug of one or more compounds in the sialic acid biosynthetic pathway such as a prodrug of sialic acid, or a pharmaceutically acceptable salt thereof, as the therapeutic agent. In another variation, the extended release formulation comprises sialic acid, or a pharmaceutically acceptable salt thereof, as the therapeutic agent and further comprises a hydrocolloid polymer, an anionic, pH-dependent gel forming co-polymer and a water swellable, pH independent polymer and optionally further comprises a lubricant and/or an excipient. In a particular variation, the extended release formulation comprises sialic acid, or a pharmaceutically acceptable salt thereof, carrageenan, sodium alginate and either hypromellose or polyethylene oxide. In a further variation, the extended release formulation comprises sialic acid, or a pharmaceutically acceptable salt thereof, carrageenan, sodium alginate, either hypromellose or polyethylene oxide, magnesium stearate and microcrystalline cellulose and colloidal silicon dioxide. In one aspect, the extended release formulation is a formulation of Table E. In yet another aspect, the extended release formulation is a formulation of Table 8. In yet another aspect, the extended release formulation is a formulation of Example 6. In yet another aspect, the extended release formulation is a formulation of Example 7.

Examples of a water-swellable, pH independent polymer include, but are not limited to, carbohydrate-based polymers such as, for example, hypromellose (formerly known as the family of hydroxypropyl methylcellulose), hydroxypropyl ethyl celluloses, hydroxypropyl cellulose, hydroxyethyl cellulose, methyl cellulose or other constituents Grades of these hypromellose copolymers typically used with the present invention include the E and K series such as for example, Dow Chemical Company's (Midland, Mich. USA) or Aqualon's (with a North American presence in Wilmington, Del.) E4M, E10M, K100LV, K4M, K15M, K25M, K100M, K200M and mixtures of various molecular weights and grades. Grades of hydroxyethyl cellulose include, for example, Aqualon's Natrasol polymers HHX (mol. Wt. 1,300,000), HX (mol. wt. 1,000,000), H (mol. wt. 1,000, 000), M (mol. wt. 720,000 and G (mol. wt. 1,150,000), and mixtures thereof. Grades of hydroxypropyl cellulose include, for example, Aqualon's HPC polymers MF and MXF (mol. wt. 580,000) and KF and HXF (mol. wt. 1,150,000), and mixtures thereof. Grades and ethyl cellulose include, for example, Dow Chemical Company's Ethocel polymers 7FP, 10FP and 100FP and Aqualon's polymers T10EC, N7, N10, N17, N22, N50, N100 and N200, and mixtures thereof. In some embodiments, the water-swellable, pH independent polymer is hypromellose (e.g., hypromellose Type 2208). In some embodiments, the water-swellable, pH independent polymer is Methocel® (e.g., Methocel® K100MPremium CR, Colorcon).

Examples of anionic, pH-dependent, gel-forming copolymer include, but are not limited to, mono-valent alginate salt such as sodium, potassium or ammonium alginate salts, or combinations thereof, and sodium carboxymethyl cellulose and the like, or mixtures of one or more alginate salt and carboxymethyl cellulose and the like. In some embodiments, the anionic, pH-dependent, gel-forming copolymer is sodium alginate (e.g., Protanal®, FMC BioPolymer).

Examples of a cationic polymer include, for example, chitosan or a derivative thereof including, for example, trimethylchitosan and quartermised chitosan, and chitosan-derived materials including, for example, those taught in U.S. Pat. No. 5,747,475. Either high or low molecular weight chitosan products can be used in the pharmaceutical formulations of the present invention and are readily available in pharmaceutical grade from suppliers located worldwide.

The hydrocolloid polymer used in the formulations of the present invention can be carrageenan. Carrageenans are available as iota, kappa and lambda carrageenans, with iota being used most frequently used and lambda being used least frequently. Various salt forms of carrageenans are also available including, for example sodium carrageenan. Typically used grades of iota carrageenan include, without limitation, carrageenan NF AEP brand colloids (Hadley, N.Y. USA) FD433 (1% viscosity; 300-400 cps) and FD384 (1% viscosity; about 100 cps). Viscosity of other carrageenan products ranges from about 50 to about 4000 cps. In some embodiments, the carrageenan is lambda carrageenan (e.g., Viscarin GP-209, FMC BioPolymer). In some embodiments, the carrageenan has a viscosity of about 1500-2000 cPs. In some embodiments, the carrageenan has a viscosity of about 1600 cPs.

The formulation and polymers useful in the extended release formulation are further described in U.S. Patent Application 2010/0160363, published on Jun. 24, 2010, and U.S. Patent Application 2010/0159001, published Jun. 24, 2010, which are incorporated herein by reference in their entireties and specifically with respect to the polymers provided therein.

In some embodiments, the extended release formulation comprises a water-swellable, pH independent polymer (e.g., hypromellose). In some embodiments, the extended release formulation further comprises an anionic, pH-dependent, gel-forming copolymer (e.g., an alginate salt). In some embodiments, the extended release formulation further comprises a hydrocolloid polymer (e.g., carrageenan). In some embodiments, the extended release formulation comprises a water-swellable, pH independent polymer (e.g. hypromellose), an anionic, pH-dependent, gel-forming copolymer (e.g., an alginate salt) and a hydrocolloid polymer (e.g., a carrageenan). In some embodiments, the extended release formulation comprises hypromellose (e.g. hypromellose Type 2208 or Methocel K100M), sodium alginate (e.g. Protanal) and a lambda carrageenan (e.g. Viscarin GP-209). In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents. In another variation, the extended release formulation comprises a prodrug of one or more compounds in the sialic acid biosynthetic pathway such as a prodrug of sialic acid, or a pharmaceutically acceptable salt thereof, as the therapeutic agent. In another variation, the extended release formulation comprises sialic acid, or a pharmaceutically acceptable salt thereof, as the therapeutic agent and further comprises a hydrocolloid polymer, an anionic, pH-dependent gel forming co-polymer and a water swellable, pH independent polymer and optionally further comprises a lubricant and/or an excipient. In a particular variation, the extended release formulation comprises sialic acid, or a pharmaceutically acceptable salt thereof, carrageenan, sodium alginate and either hypromellose or polyethylene oxide. In a further variation, the extended release formulation comprises sialic acid, or a pharmaceutically acceptable salt thereof, carrageenan, sodium alginate, either hypromellose or polyethylene oxide, magnesium stearate and microcrystalline cellulose and colloidal silicon dioxide. In one aspect, the extended release formulation is a formulation of Table E. In yet another aspect, the extended release formulation is a formulation of Table 8. In yet another aspect, the extended release formulation is a formulation of Example 6. In yet another aspect, the extended release formulation is a formulation of Example 7.

In some embodiments, the extended release formulation comprises a hydrogel (e.g., a polyethylene oxide). In some embodiments, the extended release formulation further comprises an anionic, pH-dependent, gel-forming copolymer (e.g. an alginate salt). In some embodiments, the extended release formulation further comprises a hydrocolloid polymer (e.g., carrageenan). In some embodiments, the extended release formulation comprises a hydrogel (e.g., a polyethylene oxide), an anionic, pH-dependent, gel-forming copolymer (e.g., an alginate salt) and a hydrocolloid polymer (e.g., a carrageenan). In some embodiments, the extended release formulation comprises polyethylene oxide (e.g. Polyox WSR), sodium alginate (e.g. Protanal) and a lambda carrageenan (e.g. Viscarin GP-209). In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents. In another variation, the extended release formulation comprises a prodrug of one or more compounds in the sialic acid biosynthetic pathway such as a prodrug of sialic acid, or a pharmaceutically acceptable salt thereof, as the therapeutic agent. In another variation, the extended release formulation comprises sialic acid, or a pharmaceutically acceptable salt thereof, as the therapeutic agent and further comprises a hydrocolloid polymer, an anionic, pH-dependent gel forming co-polymer and a water swellable, pH independent polymer and optionally further comprises a lubricant and/or an excipient. In a particular variation, the extended release formulation comprises sialic acid, or a pharmaceutically acceptable salt thereof, carrageenan, sodium alginate and either hypromellose or polyethylene oxide. In a further variation, the extended release formulation comprises sialic acid, or a pharmaceutically acceptable salt thereof, carrageenan, sodium alginate, either hypromellose or polyethylene oxide, magnesium stearate and microcrystalline cellulose and colloidal silicon dioxide. In one aspect, the extended release formulation is a formulation of Table E. In yet another aspect, the extended release formulation is a formulation of Table 8. In yet another aspect, the extended release formulation is a formulation of Example 6. In yet another aspect, the extended release formulation is a formulation of Example 7.

In one variation, the extended release formulation comprises: (i) a hydrocolloid polymer; (ii) an anionic, pH-dependent, gel forming co-polymer, and (iii) either a water-swellable, pH independent polymer or a hydrogel. In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents. In another variation, the extended release formulation comprises a prodrug of one or more compounds in the sialic acid biosynthetic pathway such as a prodrug of sialic acid, or a pharmaceutically acceptable salt thereof, as the therapeutic agent. In another variation, the extended release formulation comprises sialic acid, or a pharmaceutically acceptable salt thereof, as the therapeutic agent and further comprises a hydrocolloid polymer, an anionic, pH-dependent gel forming co-polymer and a water swellable, pH independent polymer and optionally further comprises a lubricant and/or an excipient. In a particular variation, the extended release formulation comprises sialic acid, or a pharmaceutically acceptable salt thereof, carrageenan, sodium alginate and either hypromellose or polyethylene oxide. In a further variation, the extended release formulation comprises sialic acid, or a pharmaceutically acceptable salt thereof, carrageenan, sodium alginate, either hypromellose or polyethylene oxide, magnesium stearate and microcrystalline cellulose and colloidal silicon dioxide. In one aspect, the extended release formulation is a formulation of Table E. In yet another aspect, the extended release formulation is a formulation of Table 8. In yet another aspect, the extended release formulation is a formulation of Example 6. In yet another aspect, the extended release formulation is a formulation of Example 7. An extended release formulation in one variation comprises a therapeutic agent as detailed herein (e.g., sialic acid) and (i) a hydrocolloid polymer; (ii) an anionic, pH-dependent, gel forming co-polymer, and (iii) either a water-swellable, pH independent polymer or a hydrogel. Exemplary extended release formulations include those listed in Table A, where it is understood that an extended release formulation may comprise any of the listed therapeutic agents in combination with at least one of any of polymers 1, 2, 3A or 3B the same as if each and every combination of therapeutic agent and polymer or combination of polymers were specifically and individually listed.

Although particular formulations may comprise a therapeutic agent of Table A and any one or more of a polymer selected from Polymers 1, 2 and 3 (A and/or B) of Table A, in a particular variation, an extended release formulation comprises a therapeutic agent of Table A, a polymer 1 of Table A, a polymer 2 of Table A and either a polymer 3A of Table A or a polymer 3B of Table A the same as if each and every combination of therapeutic agent and polymer combination were specifically and individually listed. For example, it is understood that in one aspect, an extended release formulation comprises sialic acid, carrageenan (e.g., a lambda carrageenan such as Viscarin GP-209), an alginate salt (e.g., sodium alginate such as Protanal® LF 120M), and either (i) hypromellose (e.g., hypromellose Type 2208) or (ii) polyethylene oxide (e.g., Polyox), or a pharmaceutically acceptable salt of any of the foregoing.

TABLE A

Exemplary Components for use in Extended Release Formulations.

| Formulation Component | Weight Percent of Component in Formulation |
| --- | --- |
| Therapeutic Agent (A compound in the sialic acid biosynthetic pathway or derivative thereof or salt of any of the foregoing) | mannosamine, N-acetyl mannosamine (ManNAc), ManNac-6-phosphate (ManNAc-6-P), UDP-GlcNAc, N-acetylneuraminic acid (NeuAc), NeuAc-9-phosphate (NeuAc-9-P), sialic acid (i.e., 5-N-acetylneuraminic acid), CMP-sialic acid, and/or derivatives thereof or pharmaceutically acceptable salts of the foregoing. |
| Polymer 1 (Hydrocolloid Polymer) | Carrageenan (e.g., iota, kappa or lambda carrageenan, or a salt thereof, such as Viscarin GP-209, FMC BioPolymer) |
| Polymer 2 (Anionic, pH-dependent, gel forming polymer) | Alginate or salt thereof (e.g., sodium, potassium or ammonium alginate salt such as Protanal ®, FMC BioPolymer), carboxymethyl cellulose or salt thereof (e.g., sodium carboxymethyl cellulose). |
| Polymer 3A (Water-swellable, pH independent polymer) | Hypromellose (e.g., hypromellose Type 2208, E and K series such as for example, Dow Chemical Company's (Midland, Mich. USA) or Aqualon's (with a North American presence in Wilmington, Del.) E4M, E10M, K100LV, K4M, K15M, K25M, K100M, K200M and mixtures of various molecular weights and grades); hydroxypropyl ethyl cellulose (Ethocel polymers 7FP, 10FP and 100FP and Aqualon's polymers T10EC, N7, N10, N17, N22, N50, N100 and N200, and mixtures thereof), hydroxypropyl cellulose (Aqualon's HPC polymers MF and MXF (mol. wt. 580,000) and KF and HXF (mol. wt. 1,150,000), and mixtures thereof); hydroxyethyl cellulose (e.g., Aqualon's Natrasol polymers HHX (mol. Wt. 1,300,000), HX (mol. wt. 1,000,000), H (mol. wt. 1,000,000), M (mol. wt. 720,000 and G (mol. wt. 1,150,000), and mixtures thereof); methyl cellulose.. |
| Polymer 3B (Hydrogel-forming polymer) | Polyhydroxyethyle methylacrylate (PHEMA), polyvinyl alcohol (PVA), polyvinyl pyrrolidone (PVP), polyethylene oxide (PEO), polyacrylamide (PA), polyethylene oxide (e.g., Polyox™ water soluble resin, Dow Chemical Company, Mich., USA). |

In one variation, an extended release formulation comprises a therapeutic agent of Table A, a polymer 1 of Table A, a polymer 2 of Table A and either a polymer 3A or a polymer 3B of Table A, wherein the composition comprises the therapeutic agent and polymers in any one of the weight percent ranges depicted in Table B.

TABLE B

Exemplary Weight Percent of Certain Components for Use in Extended Release Formulations.

| Formulation Component | Weight Percent of Component in Formulation |
| --- | --- |
| Therapeutic Agent (A compound in the sialic acid biosynthetic pathway or derivative thereof or salt of any of the foregoing) | From about 20 to about 80; from about 20 to about 60; from about 20 to about 50; from about 20 to about 40; from about 20 to about 30; from about 15 to about 60; from about 15 to about 50; from about 15 to about 40; from about 25 to about 60; from about 25 to about 50; from about 25 to about 40; from about 25 to about 30; from about 30 to about 60; from about 30 to about 50; from about 30 to about 45; from about 30 to about 40; from about 35 to about 60; from about 35 to about 50; from about 35 to about 45; from about 40 to about 45; about any of 35, 36, 37, 38, 39, 40, 41, 42, 43, 44, 45, 46, 47, 48, 49 and 50. |
| Polymer 1 (Hydrocolloid Polymer) | From about 1 to about 10; from about 1 to about 5; from about 3 to about 8; from about 4 to about 6; about any of 1, 2, 3, 4, 5, 6, 7, 8, 9 and 10. |
| Polymer 2 (Anionic, pH-dependent, gel forming polymer) | From about 15 to about 30; from about 15 to about 25; from about 15 to about 20; from about 20 to about 30; from about 20 to about 25; from about 2o to about 23; about any of 15, 16, 17, 18, 19, 20, 21, 22, 23, 24 and 25. |

TABLE B-continued

Exemplary Weight Percent of Certain Components for Use in Extended Release Formulations.

| Formulation Component | Weight Percent of Component in Formulation |
|---|---|
| Polymer 3A. (Water-swellable, pH independent polymer) Or Polymer 3B. (Hydrogel-forming polymer) | From about 20 to about 50; from about 20 to about 40, from about 20 to about 30; from about 20 to about 25; from about 25 to about 30; from about 22 to about 27; about any of 20, 21, 22, 23, 24, 25, 26, 27, 28, 29 and 30. |

In another variation, the extended release formulation comprises a therapeutic agent (a compound in the sialic acid biosynthetic pathway or derivative thereof or salt of any of the foregoing, such as any of the compounds detailed herein, including in Table A) and a polymer, wherein the polymer comprises: (i) a hydrocolloid polymer; (ii) an anionic, pH-dependent, gel forming co-polymer, and (iii) either a water-swellable, pH independent polymer or a hydrogel, and wherein the weight percent ratio of polymers (i):(ii):(iii) is about 1:5:5 or about 1:5:6.

The combination of (i) a hydrocolloid polymer; (ii) an anionic, pH-dependent, gel forming co-polymer, and (iii) either a water-swellable, pH independent polymer or a hydrogel is believed to provide a unique combination that is particularly advantageous for the preparation of oral dosage forms in that the combination results in any one or more of the following features: (i) provides a robust formulation (e.g., for tablet formulation); (i) is pH independent; and (iii) lends itself to granulation without affecting dissolution profile.

Further descriptions of extended release formulations and formulation components are found throughout and below.

It is understood that reference to relative weight percentages assumes that the combined total weight percentages of all components in the formulation add up to 100. It is further understood that relative weight percentages of one or more components may be adjusted upwards or downwards such that the weight percent of the components in the composition combine to a total of 100. In one aspect, the weight percentages detailed herein refer to the weight percentages of a formulation blend (e.g., prior to formulation into a unit dosage amount such as a tablet, which may be further modified, e.g., by the addition of a tablet coating). In another aspect, the weight percentages detailed herein refer to the weight percentages of a unit dosage of a formulation, in which the formulation is in a form and/or packaged for administration to an individual (e.g., a tablet that has a coating).

The polymer may be present in the extended release formulation in an amount ranging from 5 to 40 parts by weight, from 10 to 20 parts by weight, relative to 100 parts by weight of the one or more compounds in the sialic acid pathway or derivatives thereof. In some embodiments, the one or more compounds in the sialic acid pathway or derivatives thereof in such formulations includes from about 0.1 to 99.9% by weight of the formulation. In some embodiments, the one or more compounds in the sialic acid pathway or derivatives thereof in such formulations includes about any of between 20%-30%, 30%-40%, 40%-50%, or 20%-50%. In some embodiments, the extend release formulation includes about any of between 40%-50%, 50%-60%, 60%-70%, or 50% to 70% by weight of polymer.

In some embodiments, the drug load of the one or more compounds in the sialic acid pathway or derivatives thereof in the extended release formulation comprises about 20% to 80% w/w. In some embodiments, the drug load of the one or more compounds in the sialic acid pathway or derivatives thereof in the extended release formulation comprises about any one of 20% to 60% w/w, 20%-50% w/w, 20%-40% w/w, 15%-60% w/w, 15%-50% w/w, 15%-40% w/w, 25%-0.60% w/w, 25%-50% w/w, 25%-40% w/w, 30%-60% w/w, 30%-50% w/w, 30%-45% w/w, 35%-60% w/w, 35%-50% w/w, or 35%-45% w/w. In some embodiments, the drug load of the one or more compounds in the sialic acid pathway or derivatives thereof in the extended release formulation comprises at least about any one of 25% w/w, 30% w/w, 35% w/w, 40% w/w, 45% w/w, or 50% w/w. In some embodiments, the drug load of the one or more compounds in the sialic acid pathway or derivatives thereof in the extended release formulation comprises about 33% w/w. In some embodiments, the drug load of the one or more compounds in the sialic acid pathway or derivatives thereof in the extended release formulation comprises about 43% w/w In some embodiments, the extended release formulation comprises about 20 to about 50 or about 20 to about 40 or about 20 to about 30% w/w of a water-swellable, pH independent polymer (e.g., hypromellose). In some embodiments, the extended release formulation comprises about 25% w/w of a water-swellable, pH independent polymer (e.g., hypromellose). In some embodiments, the extended release formulation further comprises about 20-25% w/w of an anionic, pH-dependent, gel-forming copolymer (e.g., an alginate salt). In some embodiments, the extended release formulation further comprises about 21% w/w of an anionic, pH-dependent, gel-forming copolymer (e.g., an alginate salt). In some embodiments, the extended release formulation further comprises about 1-5% w/w of a hydrocolloid polymer (e.g., carrageenan). In some embodiments, the extended release formulation further comprises about 4% w/w of a hydrocolloid polymer (e.g., carrageenan). In some embodiments, the extended release formulation comprises about 20-30% w/w of a water-swellable, pH independent polymer (e.g. hypromellose), about 20-25% w/w of an anionic, pH-dependent, gel-forming copolymer (e.g., an alginate salt) and about 1-5 w/w of a hydrocolloid polymer (e.g., a carrageenan). In some embodiments, the extended release formulation comprises about 20-30% w/w hypromellose (e.g. hypromellose Type 2208 or Methocel K100M), about 20-25% w/w sodium alginate (e.g. Protanal) and about 1-5% w/w lambda carrageenan (e.g. Viscarin GP-209). In some embodiments, the extended release formulation comprises about 25% w/w of a water-swellable, pH independent polymer (e.g. hypromellose), about 21% w/w of an anionic, pH-dependent, gel-forming copolymer (e.g., an alginate salt) and about 4% w/w of a hydrocolloid polymer (e.g., a carrageenan). In some embodiments, the extended release formulation comprises about 25% w/w hypromellose (e.g. hypromellose Type 2208 or Methocel K100M), about 21% w/w sodium alginate (e.g. Protanal) and about 4% w/w lambda carrageenan (e.g. Viscarin GP-209).

In some embodiments, the extended release formulation comprises about 20 to about 50 or about 20 to about 40 or about 20 to about 20-30% w/w of a hydrogel (e.g., a polyethylene oxide, Polyox WSR). In some embodiments, the extended release formulation comprises about 25% w/w of a hydrogel (e.g., a polyethylene oxide, Polyox WSR). In some embodiments, the extended release formulation further comprises about 20-25% w/w of an anionic, pH-dependent, gel-forming copolymer (e.g., an alginate salt). In some embodiments, the extended release formulation further comprises about 21% w/w of an anionic, pH-dependent, gel-forming copolymer (e.g., an alginate salt). In some embodiments, the extended release formulation further comprises about 1-5% w/w of a hydrocolloid polymer (e.g., carrageenan). In some embodiments, the extended release formulation further comprises about 4% w/w of a hydrocolloid polymer (e.g., carrageenan). In some embodiments, the extended release formulation comprises about 20-30% w/w of a hydrogel (e.g., a polyethylene oxide), about 20-25% w/w of an anionic, pH-dependent, gel-forming copolymer (e.g., an alginate salt) and about 1-5% w/w of a hydrocolloid polymer (e.g., a carrageenan). In some embodiments, the extended release formulation comprises about 20-30% w/w polyethylene oxide (e.g. Polyox WSR), about 20-25% w/w sodium alginate (e.g. Protanal) and about 1-5% w/w lambda carrageenan (e.g. Viscarin GP-209). In some embodiments, the extended release formulation comprises about 25% w/w of a hydrogel (e.g., a polyethylene oxide), about 21% w/w of an anionic, pH-dependent, gel-forming copolymer (e.g., an alginate salt) and about 4% w/w of a hydrocolloid polymer (e.g., a carrageenan). In some embodiments, the extended release formulation comprises about 25% w/w polyethylene oxide (e.g. Polyox WSR), about 21% w/w sodium alginate (e.g. Protanal) and about 4% w/w lambda carrageenan (e.g. Viscarin GP-209).

Additional Formulation Components

The extended release pharmaceutical formulations comprising one or more compounds in the sialic acid biosynthetic pathway or derivative thereof as described herein may further comprise a diluent, an excipient, an antioxidant, a lubricant, a colorant, a binder, a disintegrant, and the like. It is understood that any of the extended release formulations detailed herein, including but not limited to those listed under the heading "Extended Release Formulations" (e.g., any formulation of Tables A or B) may further comprise a diluent, an excipient, an antioxidant, a lubricant, a colorant, a binder, a disintegrant, and the like as detailed herein the same as if each and every extended release formulation further comprising such a component were specifically and individually listed. In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents. In another variation, the extended release formulation comprises a prodrug of one or more compounds in the sialic acid biosynthetic pathway such as a prodrug of sialic acid, or a pharmaceutically acceptable salt thereof, as the therapeutic agent. In another variation, the extended release formulation comprises sialic acid, or a pharmaceutically acceptable salt thereof, as the therapeutic agent and further comprises a hydrocolloid polymer, an anionic, pH-dependent gel forming co-polymer and a water swellable, pH independent polymer and optionally further comprises a lubricant and/or an excipient. In a particular variation, the extended release formulation comprises sialic acid, or a pharmaceutically acceptable salt thereof, carrageenan, sodium alginate and either hypromellose or polyethylene oxide. In a further variation, the extended release formulation comprises sialic acid, or a pharmaceutically acceptable salt thereof, carrageenan, sodium alginate, either hypromellose or polyethylene oxide, magnesium stearate and microcrystalline cellulose and colloidal silicon dioxide. In one aspect, the extended release formulation is a formulation of Table E. In yet another aspect, the extended release formulation is a formulation of Table 8. In yet another aspect, the extended release formulation is a formulation of Example 6. In yet another aspect, the extended release formulation is a formulation of Example 7.

The diluent is selected so as not to affect the biological activity of the combination. Examples of such diluents are distilled water, buffered water, physiological saline, PBS, Ringer's solution, dextrose solution, and Hank's solution. The pharmaceutical formulations can also include additional substances to approximate physiological conditions, such as pH adjusting and buffering agents, toxicity adjusting agents, wetting agents and detergents. The pharmaceutical formulations can also include any of a variety of stabilizing agents. Further guidance regarding pharmaceutical formulations that are suitable for various types of administration can be found in Remington: The Science and Practice of Pharmacy, 20th Edition. Baltimore, Md.: Lippincott Williams & Wilkins, 2000.

The excipient may be selected from the group consisting of lactose, microcrystalline cellulose, corn starch, potato starch, wheat starch, sucrose, D-mannitol, precipitated calcium carbonate, dextrin, pre-gelatinized starch, and combinations thereof. The excipient, if present, may be contained in an amount of about 10 to about 90 parts by weight based on the total weight of the tablet. In some embodiments, the extend release formulation includes about any of between 40%-50%, 50%-60%, 60%-70%, or 50% to 70% by weight of excipient. In some embodiments, the excipient is microcrystalline cellulose. In some embodiments, the excipient is microcrystalline cellulose and colloidal silicon dioxide (e.g., ProSolv® SMCC HD90). In some embodiments, the extended release formulation comprises about 1-10% w/w of microcrystalline cellulose and colloidal silicon dioxide (e.g., ProSolv® SMCC HD90). In some embodiments, the extended release formulation comprises about 5% w/w of microcrystalline cellulose and colloidal silicon dioxide (e.g., ProSolv® SMCC HD90).

The binder may be selected from the group consisting of hydroxypropylcellulose, direct tabletted microcrystalline cellulose, HPMC, MC, hydroxyethylcellulose, hydroxymethylcellulose, carboxymethyl cellulose, and other cellulose derivative, PVP, PVA, paste, arabic gum, dextrin, gelatin, alginates, and combinations thereof. The binder, if present, may be used in an amount of about 2 to about 60 parts by weight based on the total weight of the tablet.

The disintegrant may be selected from the group consisting of sodium starch glycolate, crosspovidone, cross carmellose sodium, low-substituted hydroxypropylcellulose, starch, carboxymethylcellulose calcium, calcium carbonate, sodium bicarbonate, and combinations thereof. The disintegrant, if present, may be contained in an amount of about 0.1 to about 32 parts by weight based on the total weight of the tablet composition.

The lubricant may be selected from the group consisting of magnesium stearate, calcium stearate, talc, light anhydrous silicic acid, and solid polyethyl glycols and combinations thereof. The lubricant, if present, may be contained in an amount of about 0.1 to about 20 parts by weight based on the total weight of the tablet. In some embodiments, the lubricant is magnesium stearate (e.g., HyQual®). In some embodiments, the extended release formulation comprises about 0.1-1% w/w magnesium stearate (e.g., HyQual®). In some embodiments, the extended release formulation comprises about 0.5% w/w magnesium stearate (e.g., HyQual®).

For the colorant, at least one species which can be selected from titanium dioxide, iron oxide, magnesium carbonate, calcium sulfate, magnesium oxide, magnesium hydroxide, aluminum lakes, for example, Blue No. 1 Aluminum Lake, Red No. 40 Aluminum Lake, and the like can be contained in the tablet.

In another variation, an extended release formulation detailed herein (including but not limited to those listed under the heading "Extended Release Formulations" (e.g., any formulation of Tables A and B) further comprises an excipient. In a particular variation, the excipient comprises microcrystalline cellulose. In a further variation, the excipient comprises microcrystalline cellulose and colloidal silicon dioxide. In any such variations, the extended release formulation further comprising an excipient (e.g., an excipient comprising microcrystalline cellulose and colloidal silicon dioxide) comprises the excipient in about 1 to about 20 or about 1 to about 15 or about 1 to about 10 or about 1 to about 5 or about 5 to about 20 or about 5 to about 15 or about 5 to about 10 or about any one of 1, 2, 3, 4, 5, 6, 7, 8, 9 or 10 weight percent. In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents. In another variation, the extended release formulation comprises a prodrug of one or more compounds in the sialic acid biosynthetic pathway such as a prodrug of sialic acid, or a pharmaceutically acceptable salt thereof, as the therapeutic agent. In another variation, the extended release formulation comprises sialic acid, or a pharmaceutically acceptable salt thereof, as the therapeutic agent and further comprises a hydrocolloid polymer, an anionic, pH-dependent gel forming co-polymer and a water swellable, pH independent polymer and optionally further comprises a lubricant and/or an excipient. In a particular variation, the extended release formulation comprises sialic acid, or a pharmaceutically acceptable salt thereof, carrageenan, sodium alginate and either hypromellose or polyethylene oxide. In a further variation, the extended release formulation comprises sialic acid, or a pharmaceutically acceptable salt thereof, carrageenan, sodium alginate, either hypromellose or polyethylene oxide, magnesium stearate and microcrystalline cellulose and colloidal silicon dioxide. In one aspect, the extended release formulation is a formulation of Table E. In yet another aspect, the extended release formulation is a formulation of Table 8. In yet another aspect, the extended release formulation is a formulation of Example 6. In yet another aspect, the extended release formulation is a formulation of Example 7.

In another variation, an extended release formulation detailed herein (including but not limited to those listed under the heading "Extended Release Formulations" (e.g., any formulation of Tables A and B) further comprises a lubricant. In a particular variation, the lubricant comprises a stearate salt, such as magnesium stearate. In any such variations, the extended release formulation further comprising a lubricant (e.g., a stearate salt such as magnesium stearate) comprises the lubricant in about 0.1 to about 2 or about 0.1 to about 1.5 or about 0.1 to about 1.0 or about 0.01 to about 0.09-5 or about 0.1 to about 0.8 or about 0.1 to about 0.7 or about 0.1 to about 0.6 or about 0.1 to about 0.5 or about 0.2 to about 0.8 or about 0.3 to about 0.7 or about 0.4 to about 0.6 or about any one of 0.1, 0.2, 0.3, 0.4, 0.5, 0.6, 0.7, 0.8, 0.9 or 1.0 weight percent. In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents. In another variation, the extended release formulation comprises a prodrug of one or more compounds in the sialic acid biosynthetic pathway such as a prodrug of sialic acid, or a pharmaceutically acceptable salt thereof, as the therapeutic agent. In another variation, the extended release formulation comprises sialic acid, or a pharmaceutically acceptable salt thereof, as the therapeutic agent and further comprises a hydrocolloid polymer, an anionic, pH-dependent gel forming co-polymer and a water swellable, pH independent polymer and optionally further comprises a lubricant and/or an excipient. In a particular variation, the extended release formulation comprises sialic acid, or a pharmaceutically acceptable salt thereof, carrageenan, sodium alginate and either hypromellose or polyethylene oxide. In a further variation, the extended release formulation comprises sialic acid, or a pharmaceutically acceptable salt thereof, carrageenan, sodium alginate, either hypromellose or polyethylene oxide, magnesium stearate and microcrystalline cellulose and colloidal silicon dioxide. In one aspect, the extended release formulation is a formulation of Table E. In yet another aspect, the extended release formulation is a formulation of Table 8. In yet another aspect, the extended release formulation is a formulation of Example 6. In yet another aspect, the extended release formulation is a formulation of Example 7.

In a further variation, an extended release formulation detailed herein (including but not limited to those listed under the heading "Extended Release Formulations" (e.g., any formulation of Tables A and B) further comprises both an excipient and a lubricant. In any such variation, the formulation further comprising both an excipient and a lubricant comprises the excipient (e.g., an excipient comprising microcrystalline cellulose and colloidal silicon dioxide) in about 1 to about 20 or about 1 to about 15 or about 1 to about 10 or about 1 to about 5 or about 5 to about 20 or about 5 to about 15 or about 5 to about 10 or about any one of 1, 2, 3, 4, 5, 6, 7, 8, 9 or 10 weight percent and comprises the lubricant (e.g., a stearate salt such as magnesium stearate) in about 0.1 to about 2 or about 0.1 to about 1.5 or about 0.1 to about 1.0 or about 0.01 to about 0.09-5 or about 0.1 to about 0.8 or about 0.1 to about 0.7 or about 0.1 to about 0.6 or about 0.1 to about 0.5 or about 0.2 to about 0.8 or about 0.3 to about 0.7 or about 0.4 to about 0.6 or about any one of 0.1, 0.2, 0.3, 0.4, 0.5, 0.6, 0.7, 0.8, 0.9 or 1.0 weight percent. In a further variation, the formulation further comprising both an excipient and a lubricant comprises the excipient (e.g., an excipient comprising microcrystalline cellulose and colloidal silicon dioxide) in a weight percent ratio to lubricant (e.g., a stearate salt such as magnesium stearate) of about any of 1:10 or 1:11 or 1:9 or 1:10.5. In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents. In another variation, the extended release formulation comprises a prodrug of one or more compounds in the sialic acid biosynthetic pathway such as a prodrug of sialic acid, or a pharmaceutically acceptable salt thereof, as the therapeutic agent. In another variation, the extended release formulation comprises sialic acid, or a pharmaceutically acceptable salt thereof, as the therapeutic agent and further comprises a hydrocolloid polymer, an anionic, pH-dependent gel forming co-polymer and a water swellable, pH independent polymer and optionally further comprises a lubricant and/or an excipient. In a particular variation, the extended release formulation comprises sialic acid, or a pharmaceutically acceptable salt thereof, carrageenan, sodium alginate and either hypromellose or polyethylene oxide. In a further variation, the extended release formulation comprises sialic acid, or a pharmaceutically acceptable salt thereof, carrageenan, sodium alginate, either hypromellose or polyethylene oxide, magnesium stearate and microcrystalline cellulose and colloidal silicon dioxide. In one aspect, the extended release formulation is a formulation of Table E. In yet another aspect, the extended release formulation is a formulation of Table 8. In yet another aspect, the extended release formulation is a formulation of Example 6. In yet another aspect, the extended release formulation is a formulation of Example 7.

Particular extended release formulations include those listed in Table C, where the compositions comprise a therapeutic agent, a polymer 1, a polymer 2, either a polymer 3A or a polymer 3B, an excipient and a lubricant, and it is understood that each and every combination of such components is intended the same as if each and every combination were specifically and individually listed.

TABLE C

Exemplary Extended Release Formulation Compositions.

| Formulation Component | Exemplary Specific Components |
| --- | --- |
| Therapeutic Agent (A compound in the sialic acid biosynthetic pathway or derivative thereof or salt of any of the foregoing) | mannosamine, N-acetyl mannosamine (ManNAc), ManNac-6-phosphate (ManNAc-6-P), UDP-GlcNAc, N-acetylneuraminic acid (NeuAc), NeuAc-9-phosphate (NeuAc-9-P), sialic acid (i.e., 5-N-acetylneuraminic acid), CMP-sialic acid, and/or derivatives thereof or pharmaceutically acceptable salts of the foregoing. |
| Polymer 1 (Hydrocolloid Polymer) | Carrageenan (e.g., iota, kappa or lambda carrageenan, or a salt thereof, such as Viscarin GP-209, FMC BioPolymer) |
| Polymer 2 (Anionic, pH-dependent, gel forming polymer) | Alginate or salt thereof (e.g., sodium, potassium or ammonium alginate salt such as Protanal ®, FMC BioPolymer), carboxymethyl cellulose or salt thereof (e.g., sodium carboxymethyl cellulose). |
| Polymer 3A (Water-swellable, pH independent polymer) | Hypromellose (e.g., hypromellose Type 2208, E and K series such as for example, Dow Chemical Company's (Midland, Mich. USA) or Aqualon's (with a North American presence in Wilmington, Del.) E4M, E10M, K100LV, K4M, K15M, K25M, K100M, K200M and mixtures of various molecular weights and grades); hydroxypropyl ethyl cellulose (Ethocel polymers 7FP, 10FP and 100FP and Aqualon's polymers T10EC, N7, N10, N17, N22, N50, N100 and N200, and mixtures thereof), hydroxypropyl cellulose (Aqualon's HPC polymers MF and MXF (mol. wt. 580,000) and KF and HXF (mol. wt. 1,150,000, and mixtures thereof); hydroxyethyl cellulose (e.g., Aqualon's Natrasol polymers HHX (mol. Wt. 1,300,000), HX (mol. wt. 1,000,000), H (mol. wt. 1,000,000), M (mol. wt. 720,000 and G (mol. wt. 1,150,000), and mixtures thereof); methyl cellulose.. |
| Polymer 3B (Hydrogel-forming polymer) | Polyhydroxyethyle methylacrylate (PHEMA), polyvinyl alcohol (PVA), polyvinyl pyrrolidone (PVP), polyethylene oxide (PEO), polyacrylamide (PA), polyethylene oxide (e.g., Polyox ™ water soluble resin, Dow Chemical Company, Mich., USA). |
| Excipient | lactose, microcrystalline cellulose, corn starch, potato starch, wheat starch, sucrose, D-mannitol, precipitated calcium carbonate, dextrin, pre-gelatinized starch, microcrystalline cellulose and colloidal silicon dioxide (e.g., ProSolv ® SMCC HD90) and combinations thereof. |
| Lubricant | Stearate salt (such as magnesium stearate (e.g., HyQual ®) and calcium stearate), talc, light anhydrous silicic acid, and solid polyethyl glycols and combinations thereof. |

In one variation, an extended release formulation is a composition as detailed in Table C, wherein the composition comprises the formulation components in any one of the weight percent ranges depicted in Table D. It is understood that each and every combination of such components and weight percentages is intended the same as if each and every combination of component and weight percentage were specifically and individually listed.

TABLE D

Exemplary Weight Percent of Certain Components for Use in Extended Release Formulations

| Formulation Component | Exemplary Specific Components | Exemplary w/w % |
|---|---|---|
| Therapeutic Agent (A compound in the sialic acid biosynthetic pathway or derivative thereof or salt of any of the foregoing) | mannosamine, N-acetyl mannosamine (ManNAc), ManNac-6-phosphate (ManNAc-6-P), UDP-GlcNAc, N-acetylneuraminic acid (NeuAc), NeuAc-9-phosphate (NeuAc-9-P), sialic acid (i.e., 5-N-acetylneuraminic acid), CMP-sialic acid, and/or derivatives thereof or pharmaceutically acceptable salts of the foregoing. | From about 20 to about 80; from about 20 to about 60; from about 20 to about 50; from about 20 to about 40; from about 20 to about 30; from about 15 to about 60; from about 15 to about 50; from about 15 to about 40; from about 25 to about 60; from about 25 to about 50; from 25 to about 40; from about 25 to about 30; from about 30 to about 60; from about 30 to about 50; from about 30 to about 45; from about 30 to about 40; from about 35 to about 60; from about 35 to about 50; from about 35 to about 45; from about 40 to about 45; about any of 35, 36, 37, 38, 39, 40, 41, 42, 43, 44, 45, 46, 47, 48, 49 and 50. |
| Polymer 1 (Hydrocolloid Polymer) | Carrageenan (e.g., iota, kappa or lambda carrageenan, or a salt thereof, such as Viscarin GP-209, FMC BioPolymer) | From about 1 to about 10; from about 1 to about 5; from about 3 to about 8; from about 4 to about 6; about any of 1, 2, 3, 4, 5, 6, 7, 8, 9 and 10. |
| Polymer 2 (Anionic, pH-dependent, gel forming co-polymer) | Alginate or salt thereof (e.g., sodium, potassium or ammonium alginate salt such as Protanal ®, FMC BioPolymer), carboxymethyl cellulose or salt thereof (e.g., sodium carboxymethyl cellulose). | From about 15 to about 30; from about 15 to about 25; from about 15 to about 20; from about 20 to about 30; from about 20 to about 25; from about 2o to about 23; about any of 15, 16, 17, 18, 19, 20, 21, 22, 23, 24 and 25. |
| Polymer 3A (Water-swellable, pH independent polymer) | Hypromellose (e.g., hypromellose Type 2208, E and K series such as for example, Dow Chemical Company's (Midland, Mich. USA) or Aqualon's (with a North American presence in Wilmington, Del.) E4M, E10M, K100LV, K4M, K15M, K25M, K100M, K200M and mixtures of various molecular weights and grades); hydroxypropyl ethyl cellulose (Ethocel polymers 7FP, 10FP and 100FP and Aqualon's polymers T10EC, N7, N10, N17, N22, N50, N100 and N200, and mixtures thereof), hydroxypropyl cellulose (Aqualon's HPC polymers MF and MXF (mol. wt. 580,000) and KF and HXF (mol. wt. 1,150,000), and mixtures thereof); hydroxyethyl cellulose (e.g., Aqualon's Natrasol polymers HHX (mol. Wt. 1,300,000), HX (mol. wt. 1,000,000), H (mol. wt. 1,000,000), M (mol. wt. 720,000 and G (mol. wt. 1,150,000), and mixtures thereof); methyl cellulose.. | From about 20 to about 50; from about 20 to about 40, from about 20 to about 30; from about 20 to about 25; from about 25 to about 30; from about 22 to about 27; about any of 20, 21, 22, 23, 24, 25, 26, 27, 28, 29 and 30. |
| Polymer 3B (Hydrogel-forming polymer) | Polyhydroxyethyle methylacrylate (PHEMA), polyvinyl alcohol (PVA), polyvinyl pyrrolidone (PVP), polyethylene oxide (PEO), polyacrylamide (PA), polyethylene oxide (e.g., Polyox ™ water soluble resin, Dow Chemical Company, Mich., USA). | From about 20 to about 30; from about 20 to about 25; from about 25 to about 30; from about 22 to about 27; about any of 20, 21, 22, 23, 24, 25, 26, 27, 28, 29 and 30. |
| Excipient | lactose, microcrystalline cellulose, corn starch, potato starch, wheat starch, sucrose, D-mannitol, precipitated calcium carbonate, dextrin, pre-gelatinized starch, microcrystalline cellulose and colloidal silicon dioxide (e.g., ProSolv ® SMCC HD90) and combinations thereof. | From about 1 to about 20 or about 1 to about 15 or about 1 to about 10 or about 1 to about 5 or about 5 to about 20 or about 5 to about 15 or about 5 to about 10 or about any one of 1, 2, 3, 4, 5, 6, 7, 8, 9 or 10 weight percent. |
| Lubricant | Stearate salt (such as magnesium stearate (e.g., HyQual ®) and calcium stearate), talc, light anhydrous silicic acid, and solid polyethyl glycols and combinations thereof. | From about 0.1 to about 2 or about 0.1 to about 1.5 or about 0.1 to about 1.0 or about .01 to about .09-5 or about 0.1 to about 0.8 or about 0.1 to about 0.7 or about 0.1 to about 0.6 or about 0.1 to about 0.5 or about 0.2 to |

TABLE D-continued

Exemplary Weight Percent of Certain Components for Use in Extended Release Formulations

| Formulation Component | Exemplary Specific Components | Exemplary w/w % |
|---|---|---|
| | | about 0.8 or about 0.3 to about 0.7 or about 0.4 to about 0.6 or about any one of 0.1, 0.2, 0.3, 0.4, 0.5, 0.6, 0.7, 0.8, 0.9 or 1.0 weight percent. |

In another variation, extended release formulations are provided wherein the formulation comprises a therapeutic agent of Table C, a polymer 1 of Table C, a polymer 2 of Table C, a Polymer 3A or a polymer 3B of Table C, an excipient of Table C and a lubricant of Table C, wherein the components are present in the composition in the following weight percent ratios. In one aspect, the weight percent ratio of Lubricant:Polymer 1:Excipient:Polymer 2:Polymer 3A or 3B:Therapeutic Agent is about 1:8:10:40:50:85 or about 1:8.5:10.5:42.5:51:86.5 or about 1:8.4:10.6:42.4:51:86.6.

In any of the formulae detailed herein, including but not limited to the formulations in any of Tables A-D, in one aspect the therapeutic agent is sialic acid or ManNAc or a pharmaceutically acceptable salt thereof or a combination of sialic acid or ManNAc. In a particular aspect of any of the formulations detailed herein, including but not limited to the formulations in any of Tables A-D, the therapeutic agent is sialic acid, or a pharmaceutically acceptable salt thereof.

Particular extended release formulations of sialic acid are provided in Table E. In one variation, ManNAc may be used in place of sialic acid in the formulations of Table E.

TABLE E

Exemplary Extended Release Formulations of sialic acid.

| Formulation Component | Exemplary w/w % |
|---|---|
| Sialic acid, or pharmaceutically acceptable salt thereof | From about 20 to about 80; from about 20 to about 60; from about 20 to about 50; from about 20 to about 40; from about 20 to about 30; from about 15 to about 60; from about 15 to about 50; from about 15 to about 40; from about 25 to about 60; from about 25 to about 50; from 25 to about 40; from about 25 to about 30; from about 30 to about 60; from about 30 to about 50; from about 30 to about 45; from about 30 to about 40; from about 35 to about 60; from about 35 to about 50; from about 35 to about 45; from about 40 to about 45; about any of 35, 36, 37, 38, 39, 40, 41, 42, 43, 44, 45, 46, 47, 48, 49 and 50. |
| Carrageenan (e.g., lambda carrageenan such as Viscarin GP-209, FMC BioPolymer) | From about 1 to about 10; from about 1 to about 5; from about 3 to about 8; from about 4 to about 6; about any of 1, 2, 3, 4, 5, 6, 7, 8, 9 and 10. |
| Alginate or a salt thereof (e.g., sodium, potassium or ammonium alginate salt such as Protanal ® LF 120M) | From about 15 to about 30; from about 15 to about 25; from about 15 to about 20; from about 20 to about 30; from about 20 to about 25; from about 2o to about 23; about any of 15, 16, 17, 18, 19, 20, 21, 22, 23, 24 and 25. |
| Hypromellose (such as hypromellose Type 2208, e.g., Methocel ® K100 M Premium CR) | From about 20 to about 50; from about 20 to about 40, from about 20 to about 30; from about 20 to about 25; from about 25 to about 30; from about 22 to about 27; about any of 20, 21, 22, 23, 24, 25, 26, 27, 28, 29 and 30. |
| Polyethylene oxide (such as Polyethylene Oxide WSR, e.g., Polyox ™ water soluble resin, Dow Chemical Company, Mich., USA) | From about 20 to about 30; from about 20 to about 25; from about 25 to about 30; from about 22 to about 27; about any of 20, 21, 22, 23, 24, 25, 26, 27, 28, 29 and 30. |
| Microcrystalline cellulose and colloidal silicon dioxide (e.g., ProSolv ® SMCC HD90) | From about 1 to about 20 or about 1 to about 15 or about 1 to about 10 or about 1 to about 5 or about 5 to about 20 or about 5 to about 15 or about 5 to about 10 or about any one of 1, 2, 3, 4, 5, 6, 7, 8, 9 or 10 weight percent. |
| Stearate salt (such as magnesium stearate (e.g., HyQual ®) | From about 0.1 to about 2 or about 0.1 to about 1.5 or about 0.1 to about 1.0 or about .01 to about .09-5 or about 0.1 to about 0.8 or about 0.1 to about 0.7 or about 0.1 to about 0.6 or about 0.1 to about 0.5 or about 0.2 to about 0.8 or about 0.3 to about 0.7 or about 0.4 to about 0.6 or about any one of 0.1, 0.2, 0.3, 0.4, 0.5, 0.6, 0.7, 0.8, 0.9 or 1.0 weight percent. |

The components used to formulate the extended release pharmaceutical formulations are preferably of high purity and are substantially free of potentially harmful contaminants (e.g., at least National Food (NF) grade, generally at least analytical grade, and more typically at least pharmaceutical grade). Moreover, pharmaceutical formulations intended for in vivo use are usually sterile. To the extent that a given compound must be synthesized prior to use, the resulting product is typically substantially free of any potentially toxic agents which may be present during the synthesis or purification process. Compositions for parental administration are also sterile, substantially isotonic and made under GMP conditions.

The blends of the extended release formulation may have a particle size with a majority of particles being retained by a sieve size of 45 µm. In some embodiments, the blends of the extended release formulation have a particle size with at least any one of 10%, 30%, 40%, 50% of particles retained by a sieve size of 45 µm.

The extended release pharmaceutical formulations as described herein may be formulated into preparations in solid, semi-solid, liquid or gaseous forms, such as tablets, capsules, powders, granules, ointments, solutions, suppositories, injections, inhalants, gels, microspheres, and aerosols. In some embodiments of any of the extended release pharmaceutical formulations described herein, the extended release pharmaceutical formulations is formulated for administration by a variety of routes including oral, parenteral (including subcutaneous, intravenous, intramuscular and intraperitoneal), rectal, dermal, transdermal, intrathoracic, intrapulmonary and intranasal (respiratory) routes. In some embodiments, the extended release pharmaceutical formulation is formulated for oral administration.

Any of the extended release formulations detailed herein may in one variation be formulated for oral administration. For example, any of the formulations provided under the heading "Extended Release Formulations," including but not limited to any of the formulations set forth in Tables A-E, Example 6, or Example 7 may in one variation be a formulation that is suitable for oral administration. A formulation that is suitable for oral administration may be formulated as a solid oral dosage form, such as a tablet or a capsule comprising the formulation as a powder. In one aspect, a solid oral dosage form of an extended release formulation is provided wherein the solid oral dosage form comprises any formulation provided herein (including but not limited to the formulations set forth in any one of Tables A-E, Example 6, or Example 7) in tablet form, wherein the tablet further comprises a coating (e.g., Opadry-II White). In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents. In another variation, the extended release formulation comprises a prodrug of one or more compounds in the sialic acid biosynthetic pathway such as a prodrug of sialic acid, or a pharmaceutically acceptable salt thereof, as the therapeutic agent. In another variation, the extended release formulation comprises sialic acid, or a pharmaceutically acceptable salt thereof, as the therapeutic agent and further comprises a hydrocolloid polymer, an anionic, pH-dependent gel forming co-polymer and a water swellable, pH independent polymer and optionally further comprises a lubricant and/or an excipient. In a particular variation, the extended release formulation comprises sialic acid, or a pharmaceutically acceptable salt thereof, carrageenan, sodium alginate and either hypromellose or polyethylene oxide. In a further variation, the extended release formulation comprises sialic acid, or a pharmaceutically acceptable salt thereof, carrageenan, sodium alginate, either hypromellose or polyethylene oxide, magnesium stearate and microcrystalline cellulose and colloidal silicon dioxide. In one aspect, the extended release formulation is a formulation of Table E. In yet another aspect, the extended release formulation is a formulation of Table 8. In yet another aspect, the extended release formulation is a formulation of Example 6. In yet another aspect, the extended release formulation is a formulation of Example 7.

For oral administration, the sialic acid biosynthetic pathway or derivative thereof as described herein can be administered in solid dosage forms, such as capsules, tablets, and powders, or in liquid dosage forms, such as elixirs, syrups, and suspensions.

In some embodiments, the pharmaceutical formulations comprise an enteric-coating. Numerous types of acid-resistant enteric coatings are available. Examples of the acid-resistant coatings include cellulose acetate phthalate, polyvinyl acetate phthalate, shellac, an acrylic acid homopolymer or copolymer, a methacrylic acid homopolymer or copolymer, cellulose acetate trimellitate, hydroxypropyl methylcellulose phthalate or a combination of thereof. A number of copolymers of methacrylic acid are known in the art and are commercially available. Examples of such polymers are copolymers of methylmethacrylate and methacrylic acid and copolymers of ethylacrylate and methacrylic acid, and sold under the tradename Eudragit (Rohm GmbH & Co. KG): examples include Eudragit® L 100-55, Eudragit® L 30D-55, Eudragit® 100, Eudragit® S 100-55 and Eudragit® FS 30D. In some embodiments, the enteric coating comprises one or more of titanium dioxide, polydextrose, hypromellose, triacetin and macrogol/PEG. In some embodiments, the enteric coating is Opadry® II White. In some embodiments, the enteric coating (e.g., Opadry® II White) comprises about 1-5% w/w of the extended release formulation. In some embodiments, the enteric coating (e.g., Opadry® II White) comprises about 1-5% w/w of the extended release formulation.

An enteric coating can also be a time-release coating. The time-release coatings are degraded away at a relatively constant rate until the coatings dissolve sufficiently for the time-release coatings to rupture. Thus, the time required for the rupture of the enteric coatings is largely time-dependent (i.e., thickness), and largely pH independent. Examples of time-release coating materials include cellulose acetate, cellulose acetate butyrate, cellulose acetate propionate, EC, and copolymers of acrylate and methacrylates with quaternary ammonium groups such as Eudragit® RL and Eudragit® RS and Eudragit® NE30-D.

The extended release pharmaceutical formulations can be further subjected to a process of film coating. For the film coating agent, an enteric or non-enteric film coating agent may be used, and the enteric film coating agent can be cellulose acetate phthalate (CAP), polyvinyl acetate phthalate (PVAP), a methacrylate polymer (Eudragit L, S), or the like, while the non-enteric film coating agent can be hydroxypropylcellulose (HPC), MC, EC, HPMC, povidone, PVA, CA, shellac, or the like. The process of coating can be performed by, for example, a pan coating method, a fluidized bed coating method, a compression coating method, or the like.

Coated tablets of the extended release formulation may be prepared in various sizes. For example, the coated tablets may have a length of about 16-20 mm, a width of about 7-12 mm and a thickness of about 5-8 mm. In some embodiments, the coated tablets have a length of about 17.7 mm, a width of about 9.1 mm and a thickness of about 6.7 mm. In some embodiments, the coated tablets have a length of about 19.3 mm, a width of about 9.7 mm and a thickness of about 8.0 mm.

In embodiments of any of the methods, the extended release formulation comprises a drug load of about 30-60% (e.g., sialic acid and/or ManNAc), about 20-30% w/w of a water-swellable, pH independent polymer (e.g. hypromellose), about 20-25% w/w of an anionic, pH-dependent, gel-forming copolymer (e.g., an alginate salt), about 1-5% w/w of a hydrocolloid polymer (e.g., a carrageenan), about 1-10% w/w of microcrystalline cellulose and colloidal silicon dioxide (e.g., Prosolv® SMCC HD90), about 0.1-1% w/w/magnesium stearate (e.g. HyQual®), and about 1-5% of an enteric coating (e.g. Opadry® II White). In some embodiments, the extended release formulation comprises a drug load of about 30-60% (e.g., sialic acid and/or ManNAc), about 20-30% w/w hypromellose (e.g. hypromellose Type 2208 or Methocel K100M), about 20-25% w/w sodium alginate (e.g. Protanal), about 1-5% w/w lambda carrageenan (e.g. Viscarin GP-209), about 1-10% w/w of microcrystalline cellulose and colloidal silicon dioxide (e.g., Prosolv® SMCC HD90), about 0.1-1% w/w/magnesium stearate (e.g. HyQual®), and about 1-5% of an enteric coating (e.g. Opadry® II White). In some embodiments, the extended release formulation comprises a drug load of about 30-60% (e.g., sialic acid and/or ManNAc), about 25% w/w of a water-swellable, pH independent polymer (e.g. hypromellose), about 21% w/w of an anionic, pH-dependent, gel-forming copolymer (e.g., an alginate salt), about 4% w/w of a hydrocolloid polymer (e.g., a carrageenan), about 5% w/w of microcrystalline cellulose and colloidal silicon dioxide (e.g., Prosolv® SMCC HD90), about 0.5% w/w/magnesium stearate (e.g., HyQual®), and about 3.5% of an enteric coating (e.g., Opadry® II White). In some embodiments, the extended release formulation comprises a drug load of about 30-60% (e.g., sialic acid and/or ManNAc), about 25% w/w hypromellose (e.g., hypromellose Type 2208 or Methocel K100M), about 21% w/w sodium alginate (e.g. Protanal), about 4% w/w lambda carrageenan (e.g. Viscarin GP-209), about 5% w/w of microcrystalline cellulose and colloidal silicon dioxide (e.g., Prosolv® SMCC HD90), about 0.5% w/w/magnesium stearate (e.g. HyQual®), and about 3.5% of an enteric coating (e.g. Opadry® II White).

In embodiments of any of the methods, the extended release formulation comprises a drug load of about 30-60% (e.g., sialic acid and/or ManNAc), about 20-30% w/w of a hydrogel (e.g. polyethylene oxide), about 20-25% w/w of an anionic, pH-dependent, gel-forming copolymer (e.g., an alginate salt), about 1-5 w/w of a hydrocolloid polymer (e.g., a carrageenan), about 1-10% w/w of microcrystalline cellulose and colloidal silicon dioxide (e.g., Prosolv® SMCC HD90), about 0.1-1% w/w/magnesium stearate (e.g. HyQual®), and about 1-5% of an enteric coating (e.g. Opadry® II White). In some embodiments, the extended release formulation comprises a drug load of about 30-60% (e.g., sialic acid and/or ManNAc), about 20-30% w/w polyethylene oxide (e.g. Polyox WSR), about 20-25% w/w sodium alginate (e.g. Protanal), about 1-5% w/w lambda carrageenan (e.g. Viscarin GP-209), about 1-10% w/w of microcrystalline cellulose and colloidal silicon dioxide (e.g., Prosolv® SMCC HD90), about 0.1-1% w/w/magnesium stearate (e.g. HyQual®), and about 1-5% of an enteric coating (e.g. Opadry® II White). In some embodiments, the extended release formulation comprises a drug load of about 30-60% (e.g., sialic acid and/or ManNAc), about 25% w/w of a hydrogel (e.g. polyethylene oxide), about 21% w/w of an anionic, pH-dependent, gel-forming copolymer (e.g., an alginate salt), about 4% w/w of a hydrocolloid polymer (e.g., a carrageenan), about 5% w/w of microcrystalline cellulose and colloidal silicon dioxide (e.g., Prosolv® SMCC HD90), about 0.5% w/w/magnesium stearate (e.g. HyQual®), and about 3.5% of an enteric coating (e.g. Opadry® II White). In some embodiments, the extended release formulation comprises a drug load of about 30-60% (e.g., sialic acid and/or ManNAc), about 25% w/w polyethylene oxide (e.g. Polyos WSR), about 21% w/w sodium alginate (e.g. Protanal), about 4% w/w lambda carrageenan (e.g. Viscarin GP-209), about 5% w/w of microcrystalline cellulose and colloidal silicon dioxide (e.g., Prosolv® SMCC HD90), about 0.5% w/w/magnesium stearate (e.g. HyQual®), and about 3.5% of an enteric coating (e.g. Opadry® II White).

Embodiments of Formulations

In one embodiment, the extended release formulation comprises about 25% to about 50% w/w of a sialic acid, or a pharmaceutically acceptable salt, solvate, or ester thereof; about 20% to about 40% w/w of one or more water-swellable, pH independent polymers or one or more hydrogel-forming polymers; about 15% to about 30% w/w of one or more anionic, pH-dependent, gel-forming polymers; and about 3% to about 8% w/w of one or more hydrocolloid polymers or one or more cationic polymers.

In one embodiment, the extended release formulation comprises about 25% to about 50% w/w of a sialic acid, or a pharmaceutically acceptable salt, solvate, or ester thereof; about 20% to about 30% w/w hypromellose; about 3% to about 8% w/w carrageenan; and about 20% to about 25% w/w sodium alginate. In one embodiment, the extended release formulation comprises about 30% to about 45% w/w of a sialic acid. In one embodiment, the extended release formulation comprises about 22% to about 27% w/w hypromellose. In one embodiment, the extended release formulation comprises about 4% to about 6% w/w carrageenan. In one embodiment, the extended release formulation comprises about 20% to about 23% w/w carrageenan. In one embodiment, the extended release formulation further comprises about 1% to about 10% w/w of the mixture of microcrystalline cellulose and colloidal silicon dioxide; and about 0.1% to about 1% w/w magnesium stearate.

In one embodiment, the extended release formulation comprises about 25% to about 50% w/w of a sialic acid, or a pharmaceutically acceptable salt, solvate, or ester thereof; about 20% to about 30% w/w at least one of polyethylene glycol and polyethylene oxide; about 3% to about 8% w/w carrageenan; and about 20% to about 25% w/w sodium alginate. In one embodiment, the extended release formulation comprises about 30% to about 45% w/w of a sialic acid. In one embodiment, the extended release formulation comprises about 22% to about 27% w/w at least one of polyethylene glycol and polyethylene oxide. In one embodiment, the extended release formulation comprises about 4% to about 6% w/w carrageenan. In one embodiment, the extended release formulation comprises about 20% to about 23% w/w carrageenan. In one embodiment, the extended release formulation further comprises about 1% to about 10% w/w of the mixture of microcrystalline cellulose and colloidal silicon dioxide; and about 0.1% to about 1% w/w magnesium stearate.

In one specific embodiment, the extended release formulation comprises about 43.3% of a sialic acid, or a pharmaceutically acceptable salt, solvate, or ester thereof; about 25.5% w/w hypromellose; about 4.2% w/w carrageenan; about 21.1% w/w sodium alginate; about 5.3% microcrystalline cellulose and colloidal silicon dioxide; and about 0.5% magnesium stearate. In another embodiment, the extended release formulation is in 325 mg and 500 mg dosage form.

Therapeutic Utilities

The present invention provides a method for treating a sialic acid deficiency in an individual in need thereof. The method comprises orally administering a sialic acid, or a pharmaceutically acceptable salt, solvate, or ester thereof, and provides a therapeutically effective amount of sialic acid over a period of greater than about four hours.

In one embodiment, the sialic acid, or a pharmaceutically acceptable salt, solvate, or ester thereof, is in an extended release formulation, such as the ones described herein. In another embodiment, the sialic acid, or a pharmaceutically acceptable salt, solvate, or ester thereof, is in both an extended release formulation, such as the ones described herein, and an immediate release formulation. The extended release formulation and the immediate release formulation can be in separate dosage forms and be administered in a coordinated fashion. For example, an individual can take a dosage form of the extended release formation and a dosage form of the immediate release formulation concomitantly. Alternatively, extended release formulation and the immediate release formulation can be formulated in a single dosage form. For example, a single dosage form of a sialic acid, or a pharmaceutically acceptable salt, solvate, or ester thereof, can comprise an extended release component and an immediate relapse component.

In one embodiment of the present method, the sialic acid, or a pharmaceutically acceptable salt, solvate, or ester thereof, is administered on a regular dosing schedule having one or more dosing intervals per day. For example, the sialic acid, or a pharmaceutically acceptable salt, solvate, or ester thereof, can be administered once, twice, three or four times per day. In one embodiment, sialic acid, or a pharmaceutically acceptable salt, solvate, or ester thereof, is administered three times per day (TID).

In one embodiment, the present method provides a therapeutically effective amount of sialic acid over a period of greater than about eight hours per day. In some embodiments, the present method provides a therapeutically effective amount of sialic acid over a period of greater than about ten, twelve, fourteen, sixteen, or eighteen hours per day. For example, the present method provides a therapeutically effective amount of sialic acid over a period of about eight to about ten, about eight to about twelve, about eight to about fourteen, about eight to about sixteen, about ten to about fourteen, about twelve to about sixteen, or about sixteen to about twenty hours per day.

In one embodiment, the present method provides a mean $C_{min}$ sialic acid of at least about 0.11 mcg/ml at steady state during the dosing intervals. In some embodiments, the present method provides a mean $C_{min}$ sialic acid of at least about 0.12 mcg/ml, about 0.13 mcg/ml, about 0.14 mcg/ml, about 0.15 mcg/ml, about 0.16 mcg/ml, about 0.17 mcg/ml at steady state during the dosing intervals.

In one embodiment, the present method provides a mean plasma concentration of sialic acid of at least about 0.16 mcg/ml at steady state during the dosing intervals. In some embodiments, the present method provides a mean plasma concentration of sialic acid of at least about 0.17 mcg/ml, about 0.18 mcg/ml, about 0.19 mcg/ml, about 0.20 mcg/ml, about 0.21 mcg/ml, about 0.22 mcg/ml, about 0.23 mcg/ml, about 0.24 mcg/ml at steady state during the dosing intervals.

In one embodiment, the present method provides a mean plasma concentration of sialic acid at steady state during the dosing intervals that is at least about 50% higher than the mean plasma concentration of sialic acid in the individual before the administration of the sialic acid, or a pharmaceutically acceptable salt, solvate, or ester thereof. In some embodiments, the present method provides a mean plasma concentration of sialic acid at steady state during the dosing intervals that is at least about 60%, 70%, 80%, 90%, 100%, 110%, 120%, 130%, 140%, 150%, 160%, 170%, 180%, 190%, or 200% higher than the mean plasma concentration of sialic acid in the individual before the administration of the sialic acid, or a pharmaceutically acceptable salt, solvate, or ester thereof.

In one embodiment, the present method provides a plasma concentration profile of sialic acid at steady state such that the minimum plasma concentration of sialic acid during the dosing interval is at least about 35% of the maximum plasma concentration during the dosing interval. In some embodiments, the present method provides a plasma concentration profile of sialic acid at steady state such that the minimum plasma concentration of sialic acid during the dosing interval is at least about 40%, 45%, 50%, 55%, or 60% of the maximum plasma concentration during the dosing interval.

In one embodiment, the present method provides an improved absorption profile when the extended release formulation is administered under fed conditions than being administered under fasting conditions. In one embodiment, the improved absorption profile includes that the mean $C_{max}$ determined at a fasted state is higher than the mean $C_{max}$ determined at a fed state. For example, the mean $C_{max}$ determined at a fasted state is about 10%, 15%, 20%, 25%, 30%, or 35% higher than the mean $C_{max}$ determined at a fed state. In one embodiment, the improved absorption profile includes that the mean $T_{max}$ determined at a fed state is higher than the mean $T_{max}$ determined at a fasted state. For example, the ratio of the mean $T_{max}$ determined at a fed state and the mean $T_{max}$ determined at a fasted state is about 1.2:1; 1.3:1; 1.4:1; 1.5:1; 1.6:1; 1.7:1; 1.8:1; 1.9:1; or 2:1.

In one embodiment of the present invention, the extended release formulations detailed herein, including but not limited to those detailed under the heading "Extended Release Formulation" and "Additional Formulation Components" (e.g., any of the formulations of Tables A-E, Example 6 or Example 7) may exhibit any of the characteristics detailed herein and below. In a particular variation, any of the extended release formulations detailed herein may exhibit any one or more of the following characteristics: (i) capable of delivering to an individual in need thereof a therapeutically effective amount of one or more compounds in the sialic acid pathway or derivatives thereof over a period of about or greater than about any of 8, 9, 10, 11, 12, 13, 14, 15, 16, 17, 18, 19, or 20 hours; (ii) capable of delivering to an individual in need thereof a substantially constant therapeutically effective amount of one or more compounds in the sialic acid pathway or derivatives thereof over a period of about or greater than about any of 8, 9, 10, 11, 12, 13, 14, 15, 16, 17, 18, 19, or 20 hours; (iii) capable of delivering to an individual in need thereof a therapeutically effective amount of one or more compounds in the sialic acid pathway or derivatives thereof with a $T_{max}$ of between about any of 2-6 hours, 2-5 hours, or 3-6 hours during each dosing interval; (iv) capable of delivering to an individual in need thereof a therapeutically effective amount of one or more compounds in the sialic acid pathway or derivatives thereof with a $C_{max}$ of about 0.1-0.9 µg/mL, 0.1-100 µg/mL, 0.2-0.3 µg/mL, or 0.5-100 µg/mL; (v) capable of delivering to an individual in need thereof a therapeutically effective amount of one or more compounds in the sialic acid pathway or derivatives thereof with a trough level of about 0.05-0.2 µg/mL, 0.05-0.3 µg/mL, 0.1-0.3 µg/mL, or 0.1-20 µg/mL; (vi) capable of delivering to an individual in need thereof a therapeutically effective amount of one or more compounds in the sialic acid pathway or derivatives thereof with less than about any of 10%, 20%, 30%, 40%, 50%, 60%, or 70% excreted after one hour; (vii) capable of delivering to an individual in need thereof between about any of 0.01-750 mg/kg/day, 0.5-500 mg/kg/day, 1-250 mg/kg/day, 2.5-100 mg/kg/day, or 5-50 mg/kg/day of one or more compounds in the sialic acid pathway or derivatives thereof or a pharmaceutically acceptable salt of the foregoing; (viii) capable of delivering to an individual in need thereof between about any of 0.01-750 mg/kg/day, 0.5-500 mg/kg/day, 1-250 mg/kg/day, 2.5-100 mg/kg/day, or 5-50 mg/kg/day of one or more compounds in the sialic acid pathway or derivatives thereof or a pharmaceutically acceptable salt of the foregoing; (ix) has an absolute bioavailability of about 1 to about 50%; (x) has a bioavailability based on sialic acid levels in the urine of about 0.5 to about 100%; (xi) has a mean residence time (MRT) of at least about 3.5 hours. In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents. In another variation, the extended release formulation comprises a prodrug of one or more compounds in the sialic acid biosynthetic pathway such as a prodrug of sialic acid, or a pharmaceutically acceptable salt thereof, as the therapeutic agent. In another variation, the extended release formulation comprises sialic acid, or a pharmaceutically acceptable salt thereof, as the therapeutic agent and further comprises a hydrocolloid polymer, an anionic, pH-dependent gel forming co-polymer and a water swellable, pH independent polymer and optionally further comprises a lubricant and/or an excipient. In a particular variation, the extended release formulation comprises sialic acid, or a pharmaceutically acceptable salt thereof, carrageenan, sodium alginate and either hypromellose or polyethylene oxide. In a further variation, the extended release formulation comprises sialic acid, or a pharmaceutically acceptable salt thereof, carrageenan, sodium alginate, either hypromellose or polyethylene oxide, magnesium stearate and microcrystalline cellulose and colloidal silicon dioxide. In one aspect, the extended release formulation is a formulation of Table E. In yet another aspect, the extended release formulation is a formulation of Table 8. In yet another aspect, the extended release formulation is a formulation of Example 6. In yet another aspect, the extended release formulation is a formulation of Example 7.

In embodiments of any of the extended release formulations, the extended release formulation is capable of delivering to an individual in need thereof a therapeutically effective amount of one or more compounds in the sialic acid pathway or derivatives thereof over a period of greater than about any of 8, 9, 10, 11, 12, 13, 14, 15, 16, 17, 18, 19, or 20 hours. In some embodiments, the extended release formulation is capable of delivering to an individual in need thereof a therapeutically effective amount of one or more compounds in the sialic acid pathway or derivatives thereof over a period of greater than about 12 hours or greater than about 24 hours. In embodiments of any of the extended release formulations, the extended release formulation is capable of delivering to an individual in need thereof a therapeutically effective amount of one or more compounds in the sialic acid pathway or derivatives thereof over a period of between about any of 6-10 hours, 8-12 hours, 10-16, or 12-20 hours. In embodiments of any of the extended release formulations, the extended release formulation is capable of delivering to an individual in need thereof a therapeutically effective amount of one or more compounds in the sialic acid pathway or derivatives thereof over a period of about any of 8, 9, 10, 11, 12, 13, 14, 15, 16, 17, 18, 19, or 20 hours. In some embodiments, the extended release formulation is capable of delivering to an individual in need thereof a therapeutically effective amount of one or more compounds in the sialic acid pathway or derivatives thereof over a period of about 12 hours or about 24 hours. In some embodiments, the therapeutically effective amount is delivered to the bloodstream of the individual. In some embodiments, the therapeutically effective amount is delivered to muscle tissue of the individual. In some embodiments, the one or more compounds in the sialic acid pathway or derivatives thereof include ManNAc or a derivative thereof and/or sialic acid or a derivative thereof. For example, in some embodiments, the extended release formulation is capable of delivering to an individual in need thereof a therapeutically effective amount of ManNAc and/or sialic acid to muscle tissue of the individual over a period of between about any of 6-10 hours, 8-12 hours, 10-16, or 12-20 hours. In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents.

In embodiments of any of the extended release formulations, the extended release formulation is capable of delivering to an individual in need thereof a substantially constant (i.e., without large burst of drug availability and deficiencies in drug availability to the blood and/or tissues of interest (e.g., muscle tissue)) therapeutically effective amount of one or more compounds in the sialic acid pathway or derivatives thereof over a period of greater than about any of 8, 9, 10, 11, 12, 13, 14, 15, 16, 17, 18, 19, or 20 hours. In embodiments of any of the extended release formulations, the extended release formulation is capable of delivering to an individual in need thereof a substantially constant therapeutically effective amount of one or more compounds in the sialic acid pathway or derivatives thereof over a period of between about any of 6-10 hours, 8-12 hours, or 10-16, or 12-20 hours. In embodiments of any of the extended release formulations, the extended release formulation is capable of delivering to an individual in need thereof a substantially constant therapeutically effective amount of one or more compounds in the sialic acid pathway or derivatives thereof over a period of about any of 8, 9, 10, 11, 12, 13, 14, 15, 16, 17, 18, 19, or 20 hours. In some embodiments, the one or more compounds in the sialic acid pathway or derivatives thereof include ManNAc or a derivative thereof and/or sialic acid or a derivative thereof. For example, in some embodiments, the extended release formulation is capable of delivering to an individual in need thereof a substantially constant therapeutically effective amount of ManNAc and/or sialic acid to muscle tissue of the individual over a period of between about any of 6-10 hours, 8-12 hours, or 10-16, 12-20 hours. In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents.

In embodiments of any of the extended release formulations, the extended release formulation is capable of delivering to an individual in need thereof a therapeutically effective amount of one or more compounds in the sialic acid pathway or derivatives thereof with a $C_{max}$ of about 0.1-0.9 μg/mL, 0.1-100 μg/mL, 0.2-0.3 μg/mL, or 0.5-100 μg/mL. In some embodiments, the extended release formulation is capable of delivering to an individual in need thereof a therapeutically effective amount of one or more compounds in the sialic acid pathway or derivatives thereof with a $C_{max}$ of about any one 0.5-80 μg/mL, 0.5-60 μg/mL, 0.5-40 μg/mL or 0.5-20 μg/mL. In some embodiments, the extended release formulation is capable of delivering to an individual in need thereof a therapeutically effective amount of one or more compounds in the sialic acid pathway or derivatives thereof with a $C_{max}$ of about 0.5-40 μg/mL. In some embodiments, the extended release formulation is capable of delivering to an individual in need thereof a therapeutically effective amount of one or more compounds in the sialic acid pathway or derivatives thereof with a $C_{max}$ of about any one of 0.5-35 μg/mL, 0.5-30 μg/mL, 0.5-25 μg/mL, 1-40 μg/mL, 2.5-40 μg/mL, 5-40 μg/mL, 0.5-35 μg/mL, 1-35 μg/mL, 2.5-35 μg/mL, 5-35 μg/mL, 0.5-30 μg/mL, 1-30 μg/mL, 2.5-30 μg/mL, 5-30 μg/mL, 0.5-25 μg/mL, 0.1-0.3 μg/mL, 0.1-0.8 μg/mL, 0.2-0.4 μg/mL, 0.2-0.5 μg/mL, 0.2-0.8 μg/mL, 0.1-1 μg/mL, 1-25 μg/mL, 2.5-25 μg/mL, or 5-25 μg/mL. In some embodiments, the extended release formulation is capable of delivering to an individual in need thereof a therapeutically effective amount of one or more compounds in the sialic acid pathway or derivatives thereof with a $C_{max}$ of about 0.5-20 μg/mL. In some embodiments, the extended release formulation is capable of delivering to an individual in need thereof a therapeutically effective amount of one or more compounds in the sialic acid pathway or derivatives thereof with a $C_{max}$ of about 0.1-1 μg/mL. In some embodiments, the extended release formulation is capable of delivering to an individual in need thereof a therapeutically effective amount of one or more compounds in the sialic acid pathway or derivatives thereof with a $C_{max}$ of about any one of 0.5-15 μg/mL, 0.5-10 μg/mL, 1-20 μg/mL, 2.5-20 μg/mL, 5-20 μg/mL, 0.5-15 μg/mL, 1-15 μg/mL, 2.5-15 μg/mL, 5-15 μg/mL, 0.5-10 μg/mL, 1-10 μg/mL, 2.5-10 μg/mL, or 5-10 μg/mL. In some embodiments, the one or more compounds in the sialic acid pathway or derivatives thereof include ManNAc and/or sialic acid. In some embodiments, the one or more compounds in the sialic acid pathway or derivatives thereof include sialic acid. In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents.

In embodiments of any of the extended release formulations, the extended release formulation is capable of delivering to an individual in need thereof a therapeutically effective amount of one or more compounds in the sialic acid pathway or derivatives thereof with a trough level of about 0.05-0.2 μg/mL, 0.05-0.3 μg/mL, 0.1-0.3 μg/mL, or 0.1-20 μg/mL. In embodiments of any of the extended release formulations, the extended release formulation is capable of delivering to an individual in need thereof a therapeutically effective amount of one or more compounds in the sialic acid pathway or derivatives thereof with a trough level of about any one of 0.05-0.2 μg/mL, 0.05-0.3 μg/mL, 0.1-0.2 μg/mL, 0.1-0.3 μg/mL, 0.2-0.3 μg/mL, 0.1-15 μg/mL, 0.1-10 μg/mL, 0.1-5 μg/mL, 0.5-20 μg/mL, 0.5-15 μg/mL, 0.5-μg/mL, 0.5-5 μg/mL, 1-20 μg/mL, 1-15 μg/mL, 1-10 μg/mL, or 1-5 μg/mL or about any one of 0.1, 0.5, 1, 1.5, 2, 2.5, 3, 3.5, 4, 4.5, 5, 5.5, 6, 7, 8, 9, 10, 11, 12, 13, 14 or 15 μg/mL. In embodiments of any of the extended release formulations, the extended release formulation is capable of delivering to an individual in need thereof a therapeutically effective amount of one or more compounds in the sialic acid pathway or derivatives thereof with a trough level of about 0.05-0.3 μg/mL. In some embodiments, the one or more compounds in the sialic acid pathway or derivatives thereof include ManNAc and/or sialic acid. In some embodiments, the one or more compounds in the sialic acid pathway or derivatives thereof include sialic acid. In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents.

In one embodiment of the present invention, the extended release formulation is administered three times a day (TID) to provide a therapeutic effect for throughout the day, i.e., about 24 hours. For example, the extended release formulation can be taken by a patient approximately every 8 hours on a daily basis. In one embodiment, the extended release formulation provides a mean maximum plasma concentration of sialic acid from about 0.1 to about 1 μg/mL from a mean of about 0.5 to about 6 hours after a first administration. In another embodiment, the extended release formulation provides a mean maximum plasma concentration of sialic acid from about 0.15 to about 0.85 μg/mL from a mean of about 1 to about 5.5 hours after a first administration. In another embodiment, the extended release formulation provides a mean maximum plasma concentration of sialic acid from about 0.2 to about 0.7 μg/mL from a mean of about 1.5 to about 5 hours after a first administration. In another embodiment, the extended release formulation provides a mean maximum plasma concentration of sialic acid from about 0.25 to about 0.55 μg/mL from a mean of about 2 to about 4.5 hours after a first administration. In another embodiment, the extended release formulation provides mean a maximum plasma concentration of sialic acid from about 0.3 to about 0.5 µg/mL from a mean of about 2.5 to about 4 hours after a first administration. In one embodiment, the extended release formulation provides a mean minimum plasma concentration of sialic acid from about 0.1 to about 0.5 µg/mL from a mean of about 6 to about 8 hours after repeated administration approximately every 8 hours through steady-state conditions. In another embodiment of the present invention, the extended release formulation provides a mean minimum plasma concentration of sialic acid from about 0.15 to about 0.45 µg/mL from a mean of about 6 to about 8 hours after repeated administration approximately every 8 hours through steady-state conditions. In one embodiment of the present invention, the extended release formulation provides a mean minimum plasma concentration of sialic acid from about 0.2 to about 0.4 µg/mL from a mean of about 6 to about 8 hours after repeated administration approximately every 8 hours through steady-state conditions. In one embodiment of the present invention, the extended release formulation provides a mean minimum plasma concentration of sialic acid from about 0.25 to about 0.35 µg/mL from a mean of about 6 to about 8 hours after repeated administration approximately every 8 hours through steady-state conditions.

In embodiments of the present invention, the extended release formulation, when administered to a patient on a regular dosing schedule, provides to the patient a therapeutic effect continuously over the period of the regular dosing schedule. That is, the therapeutic effect, once attained after the first administration, is constant during the period of the regular dosing schedule which includes multiple dosing intervals. The regular schedule can be a dosing regimen provided by instructions accompanying the extended release formulation product. For example, such dosing regimen can be fixed or variable amount of the extended release formulation taken once per day, twice per day, three times per day, or four times per day.

In one embodiment, a total amount of about 650 mg to about 6000 mg sialic acid, or a pharmaceutically acceptable salt, solvate, or ester thereof, is administered to a patient per day on a regular dosing schedule. In another embodiment, a total amount of about 1950 mg to about 6000 mg sialic acid, or a pharmaceutically acceptable salt, solvate, or ester thereof, is administered to a patient per day on a regular dosing schedule. In one embodiment, the regular dosing schedule refers to one or more administrations with approximately equal dosing intervals in each dosing cycle. For example, a three times per day (TID) dosing schedule denotes administration of the drug three times per day with approximately eight hours dosing intervals. In one embodiment, about 650 mg of sialic acid, or a pharmaceutically acceptable salt, solvate, or ester thereof, is administered to a patient once per day. In one embodiment, about 650 mg of sialic acid, or a pharmaceutically acceptable salt, solvate, or ester thereof, is administered to a patient on a three times per day dosing schedule. In one embodiment, about 650 mg of sialic acid, or a pharmaceutically acceptable salt, solvate, or ester thereof, is administered to a patient on a three times per day dosing schedule. In one embodiment, about 650 mg of sialic acid, or a pharmaceutically acceptable salt, solvate, or ester thereof, is administered to a patient on a three times per day dosing schedule (total amount of about 1950 mg per day). In one embodiment, about 975 mg of sialic acid, or a pharmaceutically acceptable salt, solvate, or ester thereof, is administered to a patient on a three times per day dosing schedule (total amount of about 2925 mg per day). In one embodiment, about 1000 mg of sialic acid, or a pharmaceutically acceptable salt, solvate, or ester thereof, is administered to a patient on a three times per day dosing schedule (total amount of about 3000 mg per day). In one embodiment, about 1500 mg of sialic acid, or a pharmaceutically acceptable salt, solvate, or ester thereof, is administered to a patient on a three times per day dosing schedule (total amount of about 4500 mg per day). In one embodiment, about 1625 mg of sialic acid, or a pharmaceutically acceptable salt, solvate, or ester thereof, is administered to a patient on a three times per day dosing schedule (total amount of about 4875 mg per day). In one embodiment, about 2000 mg of sialic acid, or a pharmaceutically acceptable salt, solvate, or ester thereof, is administered to a patient on a three times per day dosing schedule (total amount of about 6000 mg per day). In one embodiment, about 4000 mg of sialic acid, or a pharmaceutically acceptable salt, solvate, or ester thereof, is administered to a patient on a three times per day dosing schedule (total amount of about 12000 mg per day). In one embodiment, about 2000 mg of sialic acid, or a pharmaceutically acceptable salt, solvate, or ester thereof, in extended release formulation and about 2000 mg of sialic acid, or a pharmaceutically acceptable salt, solvate, or ester thereof, in immediate release formulation are administered to a patient in combination on a three times per day dosing schedule (total amount of about 12000 mg per day).

In embodiments of the present invention, the extended release formulation, when administered to a patient on a regular dosing schedule, provides a relatively flat plasma concentration profile of sialic acid at steady state, wherein there are no substantial peak or trough in the relatively flat plasma concentration profile and the minimum plasma concentration of sialic acid in the relatively flat plasma concentration profile is sufficient to provide a therapeutic effect to the patient.

In one embodiment of the present invention, the extended release formulation, when administered to a patient on a regular dosing schedule, provides a relatively flat plasma concentration profile of sialic acid at steady state such that a mean $C_{min}/C_{max}$ sialic acid ratio during the dosing interval is about 0.40 to about 1.0, about 0.45 to about 1.0, about 0.5 to about 1.0, about 0.55 to about 1.0, about 0.6 to about 1.0, or about 0.65 to about 1.0, or about 0.7 to about 1.0, or about 0.75 to about 1.0, or about 0.8 to about 1.0, or about 0.85 to about 1.0, or about 0.9 to about 1.0, or about 0.95 to about 1.0 and the $C_{min}$ is sufficient to provide a therapeutic effect.

In one embodiment of the present invention, the extended release formulation, when administered to a patient a three times a day (TID), provides a mean $C_8/C_{max}$ sialic acid ratio of about 0.40 to about 1.0, about 0.45 to about 1.0, about 0.5 to about 1.0, about 0.55 to about 1.0, about 0.6 to about 1.0, or about 0.65 to about 1.0, or about 0.7 to about 1.0, or about 0.75 to about 1.0, or about 0.8 to about 1.0, or about 0.85 to about 1.0, or about 0.9 to about 1.0, or about 0.95 to about 1.0 at steady state after administration to the patient.

In one embodiment of the present invention, the extended release formulation, which is in a three times a day (TID) dosage form, provides to a patient a therapeutic effect for about 8 hours and a relatively flat plasma concentration profile of sialic acid at steady state such that the minimum plasma concentration of sialic acid during the dosing interval is about 40%, 45%, 50%, 55%, 60%, 65%, 70%, 75%, 80%, 85%, 90%, or 95% of the maximum plasma concentration during the dosing interval.

In one embodiment of the present invention, the extended release formulation, which is in a three times a day (TID) dosage form, provides to a patient a therapeutic effect for about 8 hours and a relatively flat plasma concentration profile of sialic acid at steady state such that the maximum plasma concentration of sialic acid during the dosing interval is about 155%, 150%, 145%, 140%, 135%, 130%, 125%, 120%, 115%, 110%, or 105% of the minimum plasma concentration during the dosing interval.

In embodiments of any of the extended release formulations, the extended release formulation is capable of delivering to an individual in need thereof a therapeutically effective amount of one or more compounds in the sialic acid pathway or derivatives thereof with less than about any of 10%, 20%, 30%, 40%, 50%, 60%, or 70% excreted after one hour. In embodiments of any of the extended release formulations, the extended release formulation is capable of delivering to an individual in need thereof a therapeutically effective amount of one or more compounds in the sialic acid pathway or derivatives thereof with less than about any of 10%, 20%, 30%, 40%, 50%, 60%, 70%, 80%, or 90% excreted after four hours. In embodiments of any of the extended release formulations, the extended release formulation is capable of delivering to an individual in need thereof a therapeutically effective amount of one or more compounds in the sialic acid pathway or derivatives thereof with less than about any one of 2, 3, 4, or 5% excreted after 12 hours. In some embodiments, the one or more compounds in the sialic acid pathway or derivatives thereof include ManNAc or a derivative thereof and/or sialic acid or a derivative thereof. In some embodiments, the one or more compounds in the sialic acid pathway or derivatives thereof include ManNAc and/or sialic acid. In some embodiments, the one or more compounds in the sialic acid pathway or derivatives thereof include sialic acid. In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents.

In embodiments of any of the extended release formulations, the extended release formulation is capable of delivering to an individual in need thereof between about any of 0.1-50 g/day, 0.5-25 g/day, 1-15 g/day, 1-10 g/day, or 2-5 g/day of one or more compounds in the sialic acid pathway or derivatives thereof. In some embodiments, the extended release formulation is capable of delivering to an individual in need thereof between about 2 g/day and 5 g/day of one or more compounds in the sialic acid pathway or derivatives thereof. In embodiments of any of the extended release formulations, the extended release formulation is capable of delivering to an individual in need thereof between about any of 0.01-750 mg/kg, 0.5-500 mg/kg, 1-250 mg/kg, 2.5-100 mg/kg, or 5-50 mg/kg of one or more compounds in the sialic acid pathway or derivatives thereof. In some embodiments, the extended release formulation is capable of delivering to an individual in need thereof between about 5 mg/kg and 50 mg/kg of one or more compounds in the sialic acid pathway or derivatives thereof. In some embodiments, the one or more compounds in the sialic acid pathway or derivatives thereof include ManNAc or a derivative thereof and/or sialic acid or a derivative thereof. For example, in some embodiments, the extended release formulation is capable of delivering to an individual in need thereof between about 5 mg/kg and 50 mg/kg of ManNAc and/or sialic acid. In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents.

In embodiments of any of the extended release formulations, the extended release formulation is capable of delivering to an individual in need thereof between about any of 0.01-750 mg/kg/day, 0.5-500 mg/kg/day, 1-250 mg/kg/day, 2.5-100 mg/kg/day, or 5-50 mg/kg/day of one or more compounds in the sialic acid pathway or derivatives thereof. In some embodiments, the extended release formulation is capable of delivering to an individual in need thereof between about 5 mg/kg/day and 50 mg/kg/day of one or more compounds in the sialic acid pathway or derivatives thereof. In some embodiments, the one or more compounds in the sialic acid pathway or derivatives thereof include ManNAc or a derivative thereof and/or sialic acid or a derivative thereof. For example, in some embodiments, the extended release formulation is capable of delivering to an individual in need thereof between about 5 mg/kg/day and 50 mg/kg/day of ManNAc and/or sialic acid. In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents.

In embodiments of any of the extended release formulations, the extended release formulation has an absolute bioavailability of about 1-50%. In some embodiments, the extended release formulation has an absolute bioavailability of about any one of 1-45%, 1-40%, 1-35%, 1-30%, 1-20%, 1-10%. In some embodiments the extended release formulation has an absolute bioavailability of about 1-25%. In some embodiments, the extended release formulation has an absolute bioavailability of about any one of 5, 10, 15, 20, 25 or 50%. In some embodiments, the one or more compounds in the sialic acid pathway or derivatives thereof include ManNAc or a derivative thereof and/or sialic acid or a derivative thereof. In some embodiments, the one or more compounds in the sialic acid pathway or derivatives thereof include sialic acid or a derivative thereof. In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents.

In embodiments of any of the extended release formulations, the extended release formulation has a bioavailability based on sialic acid levels in the urine of about 0.5-100%. In some embodiments, the extended release formulation has a bioavailability based on sialic acid levels in the urine of about any one of 0.5-2.5%, 1-2.5%, 2-8%, 2-12%, 2.5-20%, 2.5-40%, 2.5-80%, 2.5-100%. In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents.

In embodiments of any of the extended release formulations, the extended release formulation has a mean residence time (MRT) of at least about 3.5 hours. In some embodiments, the extended release formulation has a MRT of at least about any one of 3, 4, 4.5, 5, 5.5 or 6 hours. In some embodiments, the one or more compounds in the sialic acid pathway or derivatives thereof include ManNAc or a derivative thereof and/or sialic acid or a derivative thereof. In some embodiments, the one or more compounds in the sialic acid pathway or derivatives thereof include sialic acid or a derivative thereof. In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents.

The extended release formulations and/or the combination of the extended release formulation and immediate release formulation as described herein can be a sialic acid Reference Drug. The term "Reference Drug" is defined in the U.S. Federal Food and Drug Administration's (FDA) Orange Book, Approved Drug Products with Therapeutic Equivalence Evaluations. The present invention includes any bioequivalence of the extended release formulations and/or the combination of the extended release formulation and immediate release formulation as a reference drug.

"Bioequivalence" denotes the absence of a significant difference in the rate and extent to which the active agent or surrogate marker for the active agent in pharmaceutical equivalents or pharmaceutical alternatives becomes available at the site of action when administered in an appropriately designed study. In one embodiment, bioequivalence is any definition thereof as promulgated by the U.S. Food and Drug Administration or any successor agency thereof. In a specific embodiment, bioequivalence is determined according to the Federal Drug Administration's guidelines and criteria, including "GUIDANCE FOR INDUSTRY BIO-AVAILABILITY AND BIOEQUVALENCE STUDIES FOR ORALLY ADMINISTERED DRUG PRODUCTS-GENERAL CONSIDERATIONS" available from the U.S. Department of Health and Human Services (DHHS), Food and Drug Administration (FDA), Center for Drug Evaluation and Research (CDER) March 2003 Revision 1; and "GUIDANCE FOR INDUSTRY STATISTICAL APPROACHES TO ESTABLISHING BIOEQUIVALENCE" DHHS, FDA, CDER, January 2001, both of which are incorporated herein in their entirety. In another embodiment, bioequivalence is determined according to the European Medicines Agency (EMEA) document "Note for Guidance on the Investigation of Bioavailability and Bioequivalence", issued Jul. 26, 2001, available from EMEA.

In one embodiment, the present invention provides a formulation of sialic acid, or a pharmaceutically acceptable salt, solvate, or ester thereof, wherein the formulation exhibits a ratio of a geometric mean of logarithmic transformed $AUC_{0-t}$ of the formulation to a geometric mean of logarithmic transformed $AUC_{0-t}$ of the sialic acid Reference Drug from about 0.80 to about 1.25.

In one embodiment, the present invention provides a formulation of sialic acid, or a pharmaceutically acceptable salt, solvate, or ester thereof, wherein the formulation exhibits a ratio of a geometric mean of logarithmic transformed $AUC_{0-t}$ of the formulation to a geometric mean of logarithmic transformed $AUC_{0-t}$ of the sialic acid Reference Drug from about 0.80 to about 1.25.

In one embodiment, the present invention provides a formulation of sialic acid, or a pharmaceutically acceptable salt, solvate, or ester thereof, wherein the formulation exhibits a ratio of a geometric mean of logarithmic transformed $C_{max}$ of the formulation to a geometric mean of logarithmic transformed $C_{max}$ of the sialic acid Reference Drug from about 0.80 to about 1.25.

The extended release pharmaceutical formulation may be formulated for parenteral administration (e.g., by injection, for example, bolus injection or continuous infusion) and may be presented in unit dose form in ampoules, pre-filled syringes, small volume infusion containers or in multi-dose containers. The extended release pharmaceutical formulation may be may form suspensions, solutions, or emulsions in oily or aqueous vehicles. Alternatively, the one or more compounds in the sialic acid biosynthetic pathway or derivative thereof and other ingredients may be in powder form, obtained by aseptic isolation of sterile solid or by lyophilization from solution, for constitution with a suitable vehicle, e.g., sterile, pyrogen-free water, before use.

For topical administration, the extended release pharmaceutical formulation may be formulated as is known in the art for direct application to a target area. Forms chiefly conditioned for topical application take the form, for example, of creams, milks, gels, dispersion or microemulsions, lotions thickened to a greater or lesser extent, impregnated pads, ointments or sticks, aerosol formulations (e.g., sprays or foams), soaps, detergents, lotions or cakes of soap. Other conventional forms for this purpose include wound dressings, coated bandages or other polymer coverings, ointments, creams, lotions, pastes, jellies, sprays, and aerosols. The extended release pharmaceutical formulation may be delivered via patches or bandages for dermal administration. Ointments and creams may, for example, be formulated with an aqueous or oily base with the addition of suitable thickening and/or gelling agents. Drops, such as eye drops or nose drops, may be formulated with the one or more compounds in the sialic acid biosynthetic pathway or derivative thereof in an aqueous or non-aqueous base. Liquid sprays are conveniently delivered from pressurized packs. Drops can be delivered via a simple eye dropper-capped bottle, or via a plastic bottle adapted to deliver liquid contents dropwise, via a specially shaped closure.

Further, in some embodiments, the extended release pharmaceutical formulation comprising one or more compounds in the sialic acid biosynthetic pathway or derivative thereof may also be used in combination with other therapeutic agents.

Methods of Making Extended Release Formulations

Methods of making extended release formulations detailed herein are also provided. In one aspect, the formulation components (which may optionally be delumped and sieved to a desired range of particle size) are combined and mixed to provide a uniform formulation blend, which may further be used to prepare particular dosage forms, such as tablets or capsules, e.g., for oral administration. Particular dosage forms, once prepared, may be further modified to provide the final drug product, such as, e.g., by administering a coating to a tablet formed from an extended release formulation blend. Preparation of the extended release formulations may be accomplished through known techniques, such as direct compression, dry granulation and wet granulation.

Direct compression may be accomplished by delumping the formulation components and sieving to a desired range of particle size, which may be the same or different size for individual formulation components. The components are then blended, which may be accomplished by one or a series of blending steps until all formulation components are blended. The blended formulation may, if desired, be direct compressed to provide the desired product, which may be in the form of a dosage suitable for oral administration, such as a tablet. The blended formulation may also be filled into capsules or other forms for solid-dosage administration, e.g., for oral administration.

Dry granulation may also be utilized to prepare the extended release formulations detailed herein, and may be used to improve the flow or other characteristic of a blend of formulation components to be formed into a final drug product. One example of dry granulation includes delumping and/or sieving the formulation components, blending the formulation components and feeding the blend through, e.g., a roller compactor that produces a ribbon of compressed product, then milling the resulting ribbon. The milled product may then be compressed as detailed above or further blended with additional formulation components and compressed.

Wet granulation may also be utilized to prepare the extended release formulations. For example, the formulation components may be delumped and sieved to the desired size, and blended. The resulting blend may be added to an appropriate fluid bed processor equipped with a spray gun for fluidizing the blended formulation components using standard practices. The resulting granulation is dried (e.g., in the fluid bed) and milled to a desired range of particle sized and may be used for preparation of a final formulation. Wet granulation may also utilize high shear wet granulation (blended components are mixed, and frequently chopped while the solvent, typically water or other aqueous-based solvent, is sprayed over the mass during granulation).

Extended release formulations that are in tablet form preferably are compressed to a sufficient hardness to prevent premature ingress of a medium (e.g., aqueous medium) and to prevent surface pitting and breakage during coating, when applicable.

It is understood that extended release formulation blends are provided, such as a final formulation blend comprising a therapeutic agent and all formulation components in a final product (e.g., a blend comprising a therapeutic agent, a polymer, an excipient and a lubricant) as well as intermediate formulation blends that contain a portion of all formulation components in a final product (e.g., a blend comprising a therapeutic agent and a polymer but not an excipient or a lubricant, where the final product contains an excipient and a lubricant).

Methods of Treating and Preventing Sialic Acid Deficiencies

Provided herein are also methods of treating and/or preventing sialic acid deficiencies in an individual in need thereof by administering an effective amount of one or more compounds in the sialic acid pathway or derivatives thereof in any extended release formulation described herein. The methods may comprise administration of an effective amount of any of the formulations detailed herein, including any of the formulations under the heading "Extended Release Formulations," including but not limited to any of the formulations of Tables A-E as well as those formulations of Examples 12 and 13. Thus, although certain formulations are detailed below, it is understood that any extended release formulations described herein may be employed in any of the methods provided herein. In one variation, the extended release formulation comprises sialic acid, or a pharmaceutically acceptable salt thereof, as the therapeutic agent. In another variation, the extended release formulation comprises MaNAc, or a pharmaceutically acceptable salt thereof, as the therapeutic agent. In another variation, the extended release formulation comprises sialic acid, or a pharmaceutically acceptable salt thereof and MaNAc, or a pharmaceutically acceptable salt thereof, as the therapeutic agents. In another variation, the extended release formulation comprises a prodrug of one or more compounds in the sialic acid biosynthetic pathway such as a prodrug of sialic acid, or a pharmaceutically acceptable salt thereof, as the therapeutic agent. In another variation, the extended release formulation comprises sialic acid, or a pharmaceutically acceptable salt thereof, as the therapeutic agent and further comprises a hydrocolloid polymer, an anionic, pH-dependent gel forming co-polymer and a water swellable, pH independent polymer and optionally further comprises a lubricant and/or an excipient. In a particular variation, the extended release formulation comprises sialic acid, or a pharmaceutically acceptable salt thereof, carrageenan, sodium alginate and either hypromellose or polyethylene oxide. In a further variation, the extended release formulation comprises sialic acid, or a pharmaceutically acceptable salt thereof, carrageenan, sodium alginate, either hypromellose or polyethylene oxide, magnesium stearate and microcrystalline cellulose and colloidal silicon dioxide. In one aspect, the extended release formulation is a formulation of Table E. In yet another aspect, the extended release formulation is a formulation of Table 8. In another aspect, the extended release formulation is a formulation of Example 6. In another aspect, the extended release formulation is a formulation of Example 7. In some embodiments, the one or more compounds in the sialic acid pathway or derivatives thereof include ManNAc or a derivative thereof and/or sialic acid or a derivative thereof. For example, provided herein are methods of treating and/or preventing sialic acid deficiencies in an individual in need thereof by administering an effective amount of ManNAc and sialic acid in any extended release formulation described herein. In some embodiments, the methods of treating and/or preventing sialic acid deficiencies increase sialic acid production. In some embodiments, the methods of treating and/or preventing sialic acid deficiencies increase sialylation of affected tissue. In some embodiments, the method of treating and/or preventing sialic acid deficiencies comprises administering an extended release formulation comprising a drug load of about 30-60% (e.g., sialic acid and/or ManNAc), about 20-30% w/w hypromellose (e.g. hypromellose Type 2208 or Methocel K100M), about 20-25% w/w sodium alginate (e.g. Protanal), about 1-5% w/w lambda carrageenan (e.g. Viscarin GP-209), about 1-10% w/w of microcrystalline cellulose and colloidal silicon dioxide (e.g., Prosolv® SMCC HD90), about 0.1-1% w/w/magnesium stearate (e.g. HyQual®), and about 1-5% of an enteric coating (e.g. Opadry® II White). In some embodiments, the method of treating or preventing sialic acid deficiencies comprises administering an extended release formulation comprising a drug load of about 30-60% (e.g., sialic acid and/or ManNAc), about 20-30% w/w polyethylene oxide (e.g. Polyox WSR), about 20-25% w/w sodium alginate (e.g. Protanal), about 1-5% w/w lambda carrageenan (e.g. Viscarin GP-209), about 1-10% w/w of microcrystalline cellulose and colloidal silicon dioxide (e.g., Prosolv® SMCC HD90), about 0.1-1% w/w/magnesium stearate (e.g. HyQual®), and about 1-5% of an enteric coating (e.g. Opadry® II White).

Provided herein are also methods of increasing production of sialic acid (e.g., increasing production of sialic acid in muscle tissue) and the proximate substrate for glycosylation, CMP-sialic acid in an individual in need thereof by administering an effective amount of one or more compounds in the sialic acid pathway or derivatives thereof in any extended release formulation described herein. In some embodiments, the one or more compounds in the sialic acid pathway or derivatives thereof include ManNAc or a derivative thereof and/or sialic acid or a derivative thereof. For example, provided herein are methods of increasing production of sialic acid (e.g., increasing production of sialic acid in muscle tissue) in an individual in need thereof by administering an effective amount of ManNAc and sialic acid in any extended release formulation described herein.

Provided herein are also methods of increasing sialylation of muscle tissue in an individual in need thereof by administering an effective amount of one or more compounds in the sialic acid pathway or derivatives thereof in any extended release formulation described herein. In some embodiments, the one or more compounds in the sialic acid pathway or derivatives thereof include ManNAc or a derivative thereof and/or sialic acid or a derivative thereof. For example, provided herein are methods of increasing sialylation of muscle tissue in an individual in need thereof by administering an effective amount of ManNAc and sialic acid in any extended release formulation described herein.

Provided herein are also methods of improving muscle function in an individual in need thereof by administering an effective amount of one or more compounds in the sialic acid pathway or derivatives thereof in any extended release formulation described herein. In some embodiments, the one or more compounds in the sialic acid pathway or derivatives thereof include ManNAc or a derivative thereof and/or sialic acid or a derivative thereof. For example, provided herein are methods of improving muscle function in an individual in need thereof by administering an effective amount of ManNAc and sialic acid in any extended release formulation described herein.

In some embodiments, conditions associated with one or more genetic defects in the sialic acid pathway can also be addressed by treatment with one or more compounds in the sialic acid biosynthetic pathway or derivative thereof in any extended release formulation described herein, whether presently known or to be discovered. As depicted in FIG. 1, uridine diphospho-N-acetylglucosamine-2-epimerase (UDP-GlcNAc-2-epimerase) converts UDP-GlcNAc to N-acetylmannosamine (ManNAc), which is phosphorylated by ManNAc kinase in the presence of ATP to produce N-acetylmannosamine-6-phosphate (ManNAc-6-P). ManNAc-6-P is converted to N-acetylneuraminic acid-9-phosphate (NeuAc-9-P) via Neu5Ac-9-phosphate synthetase, followed by dephosphorylation of NeuAc-9-P by Neu5Ac-9-phosphate phosphatase to yield Neu5Ac (sialic acid). Sialic acid then enters the nucleus and is converted to cytidine monophosphate-sialic acid (CMP-sialic acid) via CMP-Neu5Ac synthetase. In some embodiments, any genetic deficiency regarding ManNAc kinase, Neu5Ac-9-phosphate synthetase, or Neu5Ac-9-phosphate phosphatase, or combination thereof, or condition related thereto, can be treated with an effective amount of one or more compounds in the sialic acid biosynthetic pathway or a derivative thereof in any extended release formulation described herein. For example, in some embodiments, administration of such a compound to block a particular enzymatic step in the pathway yields treatment of a condition associated with a defect regarding that particular enzyme. Accordingly, provided herein are methods of treating a subject having a condition associated with a genetic defect regarding an enzyme in the sialic acid pathway, such as ManNAc kinase, Neu5Ac-9-phosphate synthetase, or Neu5Ac-9-phosphate phosphatase or a combination thereof, comprising administering to the subject an effective amount of compound in the sialic acid biosynthetic pathway or a derivative thereof in any extended release formulation described herein.

In some embodiments, conditions associated with defects in the sialic acid biosynthetic pathway that may be treated with a compound in the sialic acid biosynthetic pathway or a derivative thereof in any extended release formulation described herein include, but are not limited to, sialuria, glomerular hyposialylation, glomerular hematuria, proteinuria podocytopathy, renal disorders involving proteinuria and hematuria due to podocytopathy and/or segmental splitting of the glomerular basement membrane, minimal change nephrosis, focal and segmental glomerulosclerosis, membranous glomerulonephritis, idiopathic nephrotic syndrome, and glycosylation deficiencies (e.g., congenital disorders of glycosylation or muscular dystrophies). In some embodiments, a condition associated with a ManNac kinase defect is selected from sialuria, glomerular hyposialylation, glomerular hematuria, proteinuria podocytopathy, renal disorders involving proteinuria and hematuria due to podocytopathy and/or segmental splitting of the glomerular basement membrane, minimal change nephrosis, focal and segmental glomerulosclerosis, membranous glomerulonephritis, and idiopathic nephrotic syndrome. In some embodiments, a condition associated with a Neu5Ac-9-phosphate phosphatase defect is a glycosylation deficiency (e.g., congenital disorders of glycosylation or muscular dystrophies).

In some embodiments, a cause of sialic acid deficiency, reduced sialic acid production, or reduced sialylation is a genetic defect that affects regulation of the sialic acid pathway: that is, genetic defects that affect sialic acid productivity or sialylation need not be constrained to genetic defects of enzymes directly in the sialic acid pathway. As such, in some embodiments, any underlying genetic defect involved in regulation of the sialic acid pathway that affects sialic acid production (e.g., where the defect causes a decrease in sialic acid production or otherwise causes sialic acid deficiency) or sialylation (e.g., where the defect causes decreased sialylation) can be treated with an effective amount of a compound in the sialic acid biosynthetic pathway or a derivative thereof in any extended release formulation described herein. In some embodiments, a genetic defect that reduces sialic acid productivity or reduces sialylation, such as by affecting regulation of GNE/MNK or other aspects of the sialic acid pathway, can be treated with a compound in the sialic acid biosynthetic pathway or a derivative thereof in any extended release formulation described herein. Accordingly, provided herein are methods of treating a subject having a condition associated with a genetic defect that reduces sialic acid productivity or reduces sialylation, such as wherein the defect affects regulation of GNE/MNK or another aspect of the sialic acid pathway, comprising administering to the subject an effective amount of a compound in the sialic acid biosynthetic pathway or a derivative thereof in any extended release formulation described herein.

Sialic acids are important for proper development and functioning of many organs and tissues, and a deficiency of sialic acid can give rise to many different types of diseases and conditions. Other types of muscle diseases have also shown that glycosylation is important for muscle function.

Nishino and Ozawa, *Curr. Opin. Neurol.* 15:539-544 (2002). In some embodiments, the sialic acid deficiency is a myopathy, muscular atrophy and/or muscular dystrophy. Myopathies that can be treated with the present compositions and methods also include distal myopathy with rimmed vacuoles (Nonaka myopathy) and the muscular dystrophy hereditary inclusion body myopathy (HIBM). In some embodiments, the methods of treating and/or preventing increase sialylation of muscle tissue. In some embodiments, the methods of treating and/or preventing improve muscle function and reduce muscle injury from physical activity, as measures by creatine kinase plasma levels after exercise. In some embodiments, the methods of treating or preventing muscle dysfunction will improve independent ambulation, stair climbing, foot drop, getting up from a chair and walking, hand grip and manipulation and pulmonary function. In some embodiments, the method further comprises identifying an individual in need thereof by determining genotype or expression levels of the gene GNE.

In some embodiments, the sialic acid deficiency is a kidney condition and diseases (e.g., those involving proteinuria and hematuria). Proteinuria involves leakage of protein from the blood into the urine. If the amount of protein in the urine is very high, this condition is often called nephrotic syndrome. Several types of diseases exhibit the symptoms of proteinuria, including high blood pressure, infections, reflux nephropathy, diabetes, and various types of glomerulonephritis, including minimal change nephrosis. Hematuria simply means blood in the urine (e.g., gross hematuria or microscopic hematuria). In some embodiments, the methods of treating and/or preventing increase sialylation of kidney tissue.

In embodiments of any of the methods, a therapeutically effective amount of one or more compounds in the sialic acid pathway or derivatives thereof is provided over a period of greater than about any of 8, 9, 10, 11, 12, 13, 14, 15, 16, 17, 18, 19, 20 hours. In some embodiments, a therapeutically effective amount of one or more compounds in the sialic acid pathway or derivatives thereof is provided over a period of greater than about 12 hours or greater than about 24 hours. In embodiments of any of the methods, a therapeutically effective amount of one or more compounds in the sialic acid pathway or derivatives thereof is provided over a period of between about any of 6-10 hours, 8-12 hours, 10-16, or 12-20 hours. In embodiments of any of the methods, a therapeutically effective amount of one or more compounds in the sialic acid pathway or derivatives thereof is provided over a period of about any of 8, 9, 10, 11, 12, 13, 14, 15, 16, 17, 18, 19, or 20 hours. In some embodiments, a therapeutically effective amount of one or more compounds in the sialic acid pathway or derivatives thereof is provided over a period of about 12 hours or about 24 hours. In some embodiments, the therapeutically effective amount is provided to the bloodstream of the individual. In some embodiments, the therapeutically effective amount is provided to muscle tissue of the individual. In some embodiments, the one or more compounds in the sialic acid pathway or derivatives thereof include ManNAc or a derivative thereof and/or sialic acid or a derivative thereof. For example, in some embodiments, a therapeutically effective amount of ManNAc and/or sialic acid is provided to muscle tissue of the individual over a period of between about any of 6-10 hours, 8-12 hours, 10-16, or 12-20 hours.

In embodiments of any of the methods, the individual in need thereof is provided a substantially constant (i.e., without large burst of drug availability and deficiencies in drug availability to the blood and/or tissues of interest (e.g., muscle tissue)) therapeutically effective amount of one or more compounds in the sialic acid pathway or derivatives thereof over a period of greater than about any of 8, 9, 10, 11, 12, 13, 14, 15, 16, 17, 18, 19, or 20 hours. In embodiments of any of the methods, the individual in need thereof is provided a substantially constant therapeutically effective amount of one or more compounds in the sialic acid pathway or derivatives thereof over a period of between about any of 1-24 hours, 4-24 hours, 6-24 hours, 8-24 hours, or 12-24 hours. In embodiments of any of the methods, the individual in need thereof is provided a substantially constant therapeutically effective amount of one or more compounds in the sialic acid pathway or derivatives thereof over a period of about any of 8, 9, 10, 11, 12, 13, 14, 15, 16, 17, 18, 19, or 20 hours. In some embodiments, the one or more compounds in the sialic acid pathway or derivatives thereof include ManNAc or a derivative thereof and/or sialic acid or a derivative thereof. For example, in some embodiments, the individual in need thereof is provided a substantially constant therapeutically effective amount of ManNAc and/or sialic acid to muscle tissue of the individual over a period of between about any of 6-10 hours, 8-12 hours, 10-16, or 12-20 hours.

In embodiments of any of the methods, less than about any of 10%, 20%, 30%, 40%, 50%, 60%, or 70% of one or more compounds in the sialic acid pathway or derivatives thereof is excreted from the individual after one hour. In embodiments of any of the methods, less than about any of 10%, 20%, 30%, 40%, 50%, 60%, 70%, 80%, or 90% of one or more compounds in the sialic acid pathway or derivatives thereof is excreted from the individual after four hours. In some embodiments, the one or more compounds in the sialic acid pathway or derivatives thereof include ManNAc or a derivative thereof and/or sialic acid or a derivative thereof. In some embodiments, the one or more compounds in the sialic acid pathway or derivatives thereof include ManNAc and/or sialic acid.

In embodiments of any of the methods, the one or more compounds in the sialic acid pathway or derivatives thereof are administered to an individual in need thereof between about any of 0.1-50 g/day, 0.5-25 g/day, 1-15 g/day, 1-10 g/day, 2-5 g/day, 0.2-25 g/day, 0.3-12 g/day, 0.4-10 g/day, 0.5-8 g/day, and 0.7-6 g/day. In some embodiments, the one or more compounds in the sialic acid pathway or derivatives thereof are administered between about 2 g/day and 5 g/day. In embodiments of any of the methods, the one or more compounds in the sialic acid pathway or derivatives thereof are administered to an individual in need thereof between about any of 0.01-750 mg/kg, 0.5-500 mg/kg, 1-250 mg/kg, 2.5-100 mg/kg, or 5-50 mg/kg. In some embodiments, the one or more compounds in the sialic acid pathway or derivatives thereof are administered to an individual in need thereof between about 5 mg/kg and 50 mg/kg. In some embodiments, the one or more compounds in the sialic acid pathway or derivatives thereof include ManNAc or a derivative thereof and/or sialic acid or a derivative thereof. For example, in some embodiments, ManNAc and/or sialic acid are administered to an individual in need thereof between about 5 mg/kg and 50 mg/kg.

In embodiments of any of the methods, the one or more compounds in the sialic acid pathway or derivatives thereof are administered to an individual in need thereof between about any of 0.01-750 mg/kg/day, 0.5-500 mg/kg/day, 1-250 mg/kg/day, 2.5-100 mg/kg/day, or 5-50 mg/kg/day. In some embodiments, the one or more compounds in the sialic acid pathway or derivatives thereof are administered to an individual in need thereof between about 5 mg/kg/day and 50 mg/kg/day. In some embodiments, the one or more compounds in the sialic acid pathway or derivatives thereof include ManNAc or a derivative thereof and/or sialic acid or a derivative thereof. For example, in some embodiments, ManNAc and/or sialic acid are administered to an individual in need thereof between about 5 mg/kg/day and 50 mg/kg/day.

In some embodiments, the effective amount of one or more compounds in the sialic acid pathway or derivatives thereof in any extended release formulation is administered once a day, twice a day, three times a day, or four times a day.

The amount of the extended release formulation according to an embodiment of the invention to be administered to a human body may be appropriately selected in accordance with the absorption rate in the body, rate of inactivation, rate of excretion, the age, gender and condition of the patient, severity of the disease, or the like. Such factors can be readily determined by the clinician employing animal models or other test systems that are available in the art.

Administration of the therapeutic agents in accordance with the present invention may be in a single dose, in multiple doses, in a continuous or intermittent manner, depending, for example, upon the recipient's physiological condition, whether the purpose of the administration is therapeutic or prophylactic, and other factors known to skilled practitioners. The administration of one or more compounds in the sialic acid pathway or derivatives thereof may be essentially continuous over a pre-selected period of time or may be in a series of spaced doses. Both local and systemic administration is contemplated.

In one embodiment, the present invention provides a method for treating a sialic acid deficiency in an individual in need thereof comprising administering to a patient under fed conditions the present extended release formulation, wherein the extended release formulation provides an improved absorption profile when administered under fed conditions than being administered under fasting conditions. In some embodiments, the absorption profile is described by the area under the plasma concentration-time curve (AUC) over a 8, 12, or 24 hours period of time (correlating to the amount of drug absorbed or bioavailability), $C_{max}$ (maximum concentration of the drug in the blood), and $T_{max}$ (time to reach $C_{max}$). In one embodiment, the improved absorption profile denotes a less sharp and more flat shape of the concentration-time curve. For example, the improved absorption profile can denote an AUC with somewhat lower, somewhat higher, or substantially the same value but a lower $C_{max}$ and higher $T_{max}$. In one embodiment, the mean AUC determined at a fed state is substantially similar to or higher than the mean AUC determined at a fasted state. the mean $C_{max}$ determined at a fed state is lower than the mean AUC determined at a fasted state. In another embodiment, the mean $C_{max}$ determined at a fed state is lower than the mean AUC determined at a fasted state. In another embodiment, the mean $T_{max}$ determined at a fed state is higher than the mean AUC determined at a fasted state.

Unit Dosages and Articles of Manufacture

Also provided herein are articles of manufacture and unit dosages which include the extended release formulations comprising one or more compounds in the sialic acid pathway or derivatives thereof described herein.

Provided herein are articles of manufacture or kits comprising: (a) a container comprising the extended release pharmaceutical formulation comprising one or more compounds in the sialic acid biosynthetic pathway or derivative thereof described herein; and (b) a package insert with instructions for treating and/or preventing a sialic acid deficiency in a patient. In some embodiments, the one or more compounds in the sialic acid pathway or derivatives thereof include ManNAc or a derivative thereof and/or sialic acid or a derivative thereof.

The article of manufacture comprises a container and a label or package insert on or associated with the container. Suitable containers include, for example, bottles, vials, syringes, etc. The containers may be formed from a variety of materials such as glass or plastic. The container holds or contains a formulation and may have a sterile access port (for example the container may be an intravenous solution bag or a vial having a stopper pierceable by a hypodermic injection needle). At least one active agent in the composition is the polypeptide. The label or package insert indicates that the composition's use in a subject with specific guidance regarding dosing amounts and intervals of polypeptide and any other drug being provided. The article of manufacture may further include other materials desirable from a commercial and user standpoint, including other buffers, diluents, filters, needles, and syringes. In some embodiments, the container is a syringe. In some embodiments, the syringe is further contained within an injection device. In some embodiments, the injection device is an auto injector.

A "package insert" is used to refer to instructions customarily included in commercial packages of therapeutic products, that contain information about the indications, usage, dosage, administration, contraindications, other therapeutic products to be combined with the packaged product, and/or warnings concerning the use of such therapeutic products.

Provided herein are also unit dosages which include the extended release formulations comprising one or more compounds in the sialic acid pathway or derivatives thereof. In some embodiments, the one or more compounds in the sialic acid pathway or derivatives thereof include ManNAc or a derivative thereof and/or sialic acid or a derivative thereof.

Unit dosage forms comprising any of the extended release formulations described herein, including but not limited to those formulations detailed under the heading "Extended Release Formulations," such as any of the formulations of Tables A-E, Example 6, or Example 7, are described. These unit dosage forms can be stored in a suitable packaging in single or multiple unit dosages and may also be further sterilized and sealed. For convenience and ease of patient compliance, the extended release formulations may be delivered in the form of unit dosage forms, which may be administered to an individual. In one variation, the extended release formulation is a solid substance and unit dosage forms thereof may be prepared in the form of tablets, capsules, sachets and chewable tablets or tablets not intended to be chewed. In one aspect, the dosage form is in the form of a capsule or tablet, preferably in the form of a tablet. In some embodiments, the dosage form is in the form of a tablet not intended to be chewed. In some embodiments, the dosage form is in the form of a tablet not intended to be crushed. In some embodiments, the dosage form is in the form of a tablet not intended to be chewed or crushed.

The preparation of the unit forms generally involves a step of preparing a blend filling, either by volume or weight. For example, in production of tablets and capsules, the extended release formulation blend is volume filled into a die or capsule, respectively. In one aspect, a batch of unit dosage forms has the same potency (amount of drug per unit dosage form) within an allowable margin, which in one variation is a relative standard deviation (RSD) of less than 6% and in another variation is less than 8.0 or 7.8%.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed.

Example 1

Preparation of Sialic Acid 250 mg Strength Tablets Using Dry Blend Method of Manufacture Experimental/Materials Sialic Acid (Food & Bio Research center, Inc. Kyoto Japan) was stored in aluminum foil bags at −20° C. However, handling and processing of prototypes were all under ambient room temperature. In-process materials and bulk tablets were stored in double polyethylene bags with desiccant. The sialic acid was evaluated for physical properties consisting of morphology, particle size by sieve analysis, bulk and tap density.

50 gram lab-scale batches were prepared using bag-blending, manual filling and hand turning of the tablet press to compress tablets to evaluate dissolution as the first level of screening. Tablets were manufactured using the ProCR platform. Their formulas are listed below in Table 1 and 2.

TABLE 1

Quantitative Formula for Sialic Acid, ProCR Hypromellose 250 mg Tablets:

| Ingredient | Vendor | mg/Tablet | % w/w | g/batch |
|---|---|---|---|---|
| Sialic Acid (N-Acetylneuraminic acid) | Food and BioResearch Center, Inc | 249.75 | 33.3 | 16.65 |
| Hypromellose, Type 2208 (Methocel ® K100 M Premium CR) | Colorcon | 225.0 | 30.0 | 15.0 |
| Sodium Alginate (Protanal ® LF 120M) | FMC Biopolymer | 187.5 | 25.0 | 12.5 |
| Carrageenan (Viscarin GP-209) | FMC Biopolymer | 37.5 | 5.0 | 2.5 |
| Microcrystallline Cellulose and Colloidal Sillicon Dioxide (ProSolv ® SMCC HD 90) | JRS Pharma | 46.5 | 6.2 | 3.1 |
| Magnesium Stearate (HyQual ®), Vegatable Source Product Code 2257 | Mallinckrodt | 3.75 | 0.5 | 0.25 |
| Total |  | 750 | 100% | 50 |

TABLE 2

Quantitative Formula for Sialic Acid ProCR Polyox, 250 mg Tablets:

| Ingredient | Vendor | mg/Tablet | % w/w | g/batch |
|---|---|---|---|---|
| Sialic Acid (N-Acetylneuraminic acid) | Food and BioResearch Center, Inc | 249.75 | 33.3 | 16.65 |
| Polyethylene Oxide WSR (Polyox) | Dow Chemical Company | 225.0 | 30.0 | 15.0 |
| Sodium Alginate (Protanal ® LF 120M) | FMC Biopolymer | 187.5 | 25.0 | 12.5 |
| Carrageenan (Viscarin GP-209) | FMC Biopolymer | 37.5 | 5.0 | 2.5 |
| Microcrystallline Cellulose and Colloidal Silicon Dioxide (ProSolv ® SMCC HD 90) | JRS Pharma | 46.5 | 6.2 | 3.1 |
| Magnesium Stearate (HyQual ®), Vegatable Source Product Code 2257 | Mallinckrodt | 3.75 | 0.5 | 0.25 |
| Total |  | 750 | 100 | 50 |

Sialic Acid, hypromellose Type 2208, sodium alginate, carrageenan and microcrystalline cellulose with colloidal silicon dioxide were delumped using a #20 USA standard sieve and weighed per the quantitative formula. The ingredients were combined in a small ziplock bag and blended for 15 minutes. Magnesium stearate was delumped using a #40 USA standard screen, weighed per quantitative formula, and added to the blended ingredients in the bag. The ingredients were blended for an additional three minutes. The final blends, as well as the un-sieved sialic acid were characterized using bulk density, tap density, particle size sieve analysis, Carr's Compressibility Index, and minimum critical orifice. The final blend of each prototype was compressed on the Korsch PH100 tablet press. The resulting tablets were submitted to the analytical lab for dissolution testing.

Sialic Acid Characterization

Figure 2:
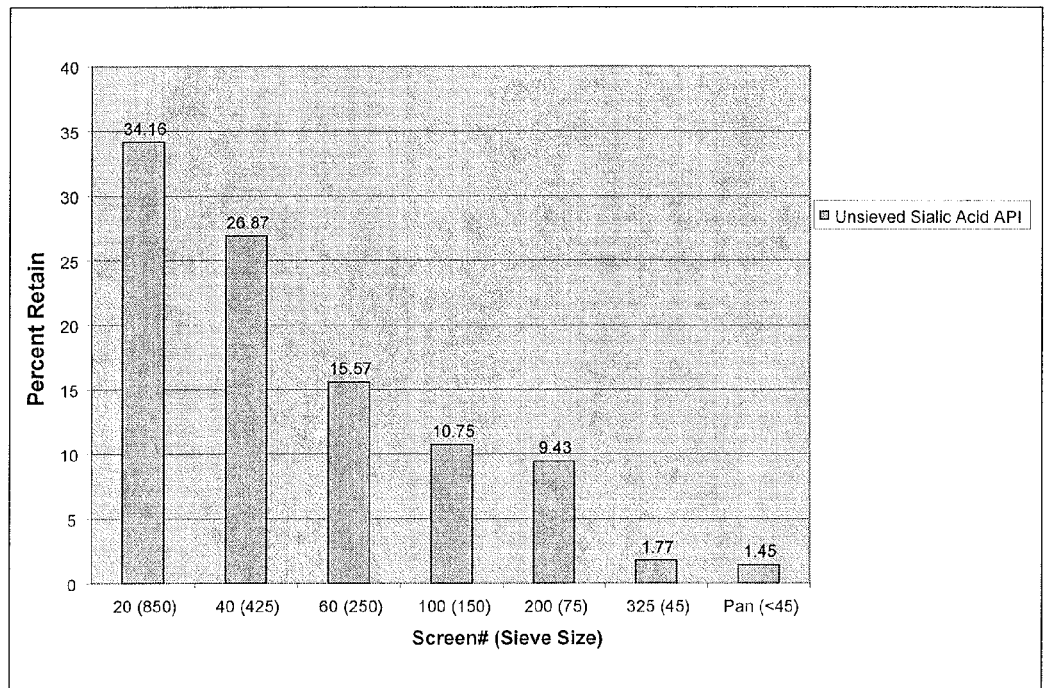
FIG. 2 shows the particle size distribution for sialic acid.

Sialic Acid was visually characterized as a white fluffy powdery substance. Its bulk density was 0.293 g/mL, and its tap density was 0.419 g/ml. The Carr's Compressibility Index was 30%, and the minimum critical orifice diameter was 18 mm. The particle size sieve analysis of Sialic Acid (Table 3) revealed a distribution of coarse and midsize particles as shown in FIG. 2. The sialic acid was sized prior to blending to facilitate blend homogeneity.

TABLE 3

Particle Size Distribution for Sialic Acid

| Sieve # (Mesh size (um)) | Unsieved Sialic Acid (N-Acetylneuraminic acid) |
|---|---|
| 20 (850) | 34.16 |
| 40 (425) | 26.87 |
| 60 (250) | 15.57 |
| 100 (150) | 10.75 |
| 200 (75) | 9.3 |
| 325 (45) | 1.77 |
| Pan (<45) | 1.45 |

ProCR Sialic Acid, 250 mg CR Tablets

Figure 3:
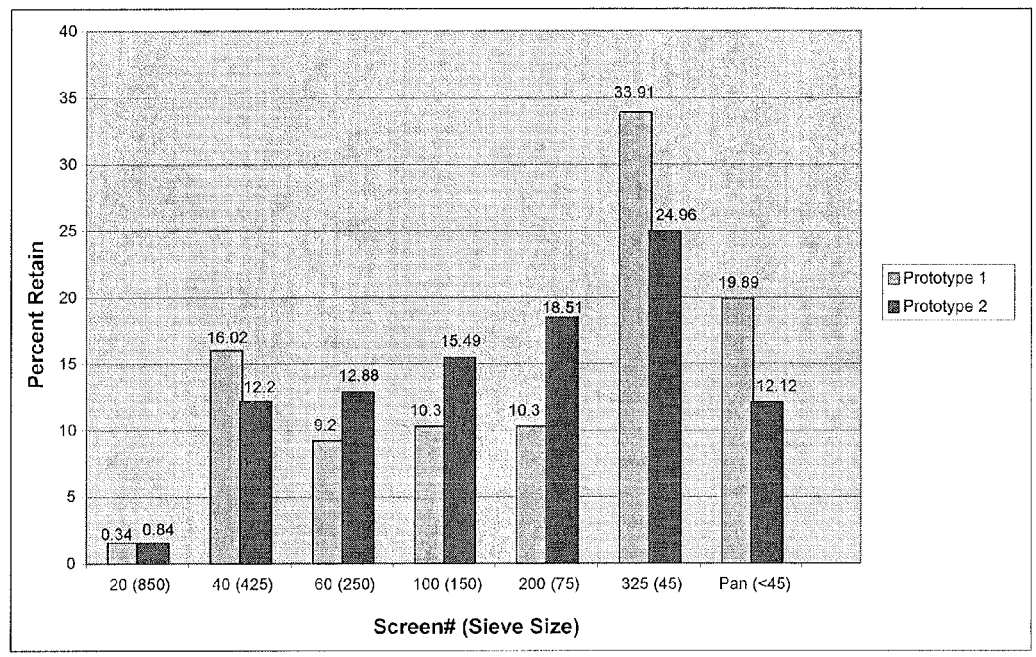
FIG. 3 shows the particle size distribution plot for ProCR sialic acid 250 mg final blends.

Both prototype blends, ProCR hypromellose and ProCR Polyox, were compressed into tablets using 0.3300×0.7100 inch modified oval tooling targeting a tablet weight of 750 mg and a hardness range of 17 to 20 Kp. During tableting, powder bridging in the die cavity was observed for ProCR hypromellose. This was an indication that the blend needed to be densified to improve flowability on the tablet press. ProCR Polyox appeared denser and seemed to flow better on the tablet press. However, its Carr's Compressibility Index and minimum critical orifice diameter results, as shown in Table 4, indicated that it also needed further processing such as, granulation. The particle size distribution of the Polyox prototype seemed to be more dispersed over various screen sizes than the hypromellose prototype shown in Table 5 and FIG. 3.

TABLE 4

Physical Characterization Results of Sialic Acid 250 mg

| Powder | Bulk Density (g/mL) | Tap Density (g/mL) | Carr's Compressibility Index (%) | Flodex Critical Orifice (mm) |
|---|---|---|---|---|
| Sialic Acid (N-Acetylneuraminic acid) | 0.293 | 0.419 | 30 (poor flow) | 18 |
| Prototype 1 (Hypromellose) | 0.359 | 0.543 | 33.8 (very poor flow) | 20 |
| Prototype 2 (Polyox) | 0.439 | 0.716 | 38.7 (very very poor flow) | 18 |

TABLE 5

Particle Size Distribution for ProCR Sialic Acid, 250 mg Tablets.

| Sieve # (Mesh size (um)) | Prototype 1 with Hypromellose % Retain | Prototype 2 with Polyethylene oxide % Retain |
|---|---|---|
| 20 (850) | 0.34 | 0.84 |
| 40 (425) | 16.02 | 15.20 |
| 60 (250) | 9.2 | 12.88 |
| 100 (150) | 10.3 | 15.49 |
| 200 (75) | 10.3 | 18.51 |
| 325 (45) | 33.91 | 24.96 |
| Pan (<45) | 19.89 | 12.12 |

Figure 4:
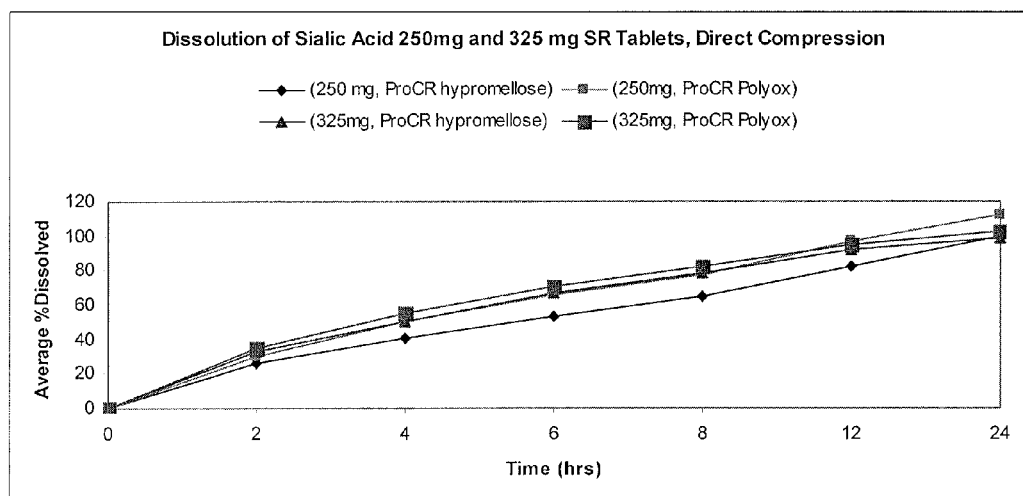
FIG. 4 shows the dissolution plot of sialic acid 250 and 325 mg sustained release (SR) tablets by direct compression.

The compression of the tablets resulted in a weight range of 3-5% of the target of 750 mg. The variability was primarily due to the manual filling and poor flow. Regardless of the weight variability, the tablet appearance and hardness was good, ranging from 13 to 18 Kp, as listed in Table 6. The dissolution results showed a first order sustained release profile over a 12 hour period, as shown in Table 7 and FIG. 4.

TABLE 6

Physical Data of Sialic Acid 250 and 325 mg Tablets

| Test | Hypromellose 250 mg Tablets | Polyox 250 mg Tablets | Hypromellose 325 mg Tablets | Polyox 325 mg Tablets |
|---|---|---|---|---|
| Tablet Weight (mg) | 744-787 | 746-751 | 747-766 | 745-771 |
| Tablet Thickness (in) | 0.268-0.271 | 0.261-0.263 | 0.291-0.295 | 0.283-0.286 |
| Tablet Hardness (kp) | 17.5 | 18.3 | 13.2 | 13.0 |
| Tablet Friability (%) | ND | ND | ND | ND |

ND: Not determined

TABLE 7

Dissolution Results of Direct Compression Prototypes

| Test | Hypromellose 250 mg Tablets | Polyox 250 mg Tablets | Hypromellose 325 mg Tablets | Polyox 325 mg Tablets |
|---|---|---|---|---|
| Dissolution (Average n = 3) % Release | | | | |
| 2 hr | 26 | 30 | 33 | 35 |
| 4 hr | 41 | 50 | 50 | 55 |
| 6 hr | 53 | 66 | 67 | 71 |
| 8 hr | 65 | 77 | 78 | 82 |
| 12 hr | 82 | 97 | 92 | 95 |
| 16 hr* | — | — | 99 | 103 |
| 24 hr | 100 | 112 | — | — |

*Represented as last time point in graph

Example 2

Preparation of Sialic Acid 325 and 500 mg Development Prototypes

Initially, two small 50 gram dry blend batches were manufactured with an increased drug load from 33% w/w to 43% w/w to verify that the drug release profile was acceptable. The two compositions are listed in Table 8 as hypromellose and Polyox. The tabletting was done as described before using a manual fill into the die cavity.

TABLE 8

Quantitative Formula for Sialic Acid 325 mg and 500 mg sustained release Tablets Prototypes:

| Ingredient | Vendor | mg/Tablet ProCR Hypromellose | mg/Tablet ProCR Polyox | % w/w | g/batch 50 g size | g/batch 1800 g size |
|---|---|---|---|---|---|---|
| Sialic Acid (N-Acetylneuraminic acid) | Food and BioResearch Center, Inc | 325.0 | 325.0 | 43.3 | 21.65 | 779.4 |
| Hypromellose, Type 2208 (Methocel ® K100 M Premium CR) | Colorcon | 191.3 | — | 25.5 | 12.75 | 459 |
| Polyethylene Oxide WSR (Polyox) | | — | 191.3 | 25.5 | 12.75 | 459 |
| Sodium Alginate (Protanal ® LF 120M) | FMC Biopolymer | 159.0 | 159.0 | 21.2 | 10.60 | 381.6 |

TABLE 8-continued

Quantitative Formula for Sialic Acid 325 mg and 500 mg sustained release Tablets Prototypes:

| Ingredient | Vendor | mg/Tablet ProCR Hypromellose | mg/Tablet ProCR Polyox | % w/w | g/batch 50 g size | g/batch 1800 g size |
|---|---|---|---|---|---|---|
| Carrageenan (Viscarin GP-209) | FMC Biopolymer | 31.5 | 31.5 | 4.2 | 2.10 | 75.6 |
| Microcrystallline Cellulose and Colloidal Sillicon Dioxide (ProSolv ® SMCC HD 90) | JRS Pharma | 39.8 | 39.8 | 5.3 | 2.65 | 95.4 |
| Magnesium Stearate (HyQual ®), Vegatable Source Product Code 2257 | Mallinckrodt | 3.8 | 3.8 | 0.5 | 0.25 | 9.0 |
| Total for 325 mg Strength | | 750.4 | 750.4 | 100 | 50 | 1800 |
| Total for 500 mg Strength | | 1154.5 | 1154.8 | 100 | — | — |

Wet Granulation Method of Manufacture

In order to avoid bridging and poor flow during compression batch sizes were scaled up from 50 grams to 1800 grams, and a high shear granulation method of manufacture was used to produce 325 and 500 mg dose strengths while maintaining good tablet compression properties. The 325 and 500 mg dose strengths shared a common blend that was divided prior to compression. Two tablet sizes were produced: A 325 mg dose strength tablet with a length of 17.7 mm, a width of 9.1 mm and a thickness of 6.7 mm; and a 500 mg dose strength tablet with a length of 19.3 mm, a width of 9.7 mm and a thickness of 8.0 mm). The following equipment and process were used to make these tables.

Experimental/Materials

All raw materials were used as received from vendors as listed in Table 8. The batch size was 1800 grams. The following equipment was used:

Fielder PPI High Shear Granulator

Niro-Aeromatic MP-1 Multi-processor

FitzMill JT Homoloid equipped with knives forward, 0.079" round hole screen

4 Qt PK Blender

Korsch PH100 tablet Press equipped with 0.350"× 0.6875" modified oval tooling for the 750 mg tablet and 0.374"×0.7480" modified oval tooling for the 1154 mg tablet Accela-cota model 24MK III (24" coating pan)

All the raw materials with exception of magnesium stearate were charged to the PP-1 granulator and premixed for 3 minutes at 300 rpm impeller speed, no chopper. A baseline loss on drying determination was performed and the ungranulated hypromellose formula was determined to be 3.4% water while the Polyox formulation was 2.9%. Water was sprayed at approximately 200 grams/minute while mixing at 300 rpm with a slow chopper speed. The hypromellose formulation used 43% water (778 g water sprayed) of the 1.8 kg batch size while the Polyox formulation sprayed 52% water (905 g water sprayed) with a 2 minute post spray mix. The granulation was transferred into the MP-1 fluid bed and dried with an inlet temperature of 75° C. until the loss on drying (LOD) was <3%; equal to or slightly lower than the baseline moisture of the un-granulated formulations. The dried granulation was passed through a #4 mesh hand screen. The large granules retained on the #4 mesh were segregated and discarded. The remaining granules were sized through the FitzMill at low speed, knives forward. The blend was then lubricated with the magnesium stearate for 3 minutes. The final blend was compressed into tablets using a Korsch rotary press. After dissolution results were obtained, the core tablets were coated with a non-functional, Opadry II, white to a weight gain of approximately 4.5% w/w.

Outline of Dissolution Conditions were as follows:

900 mL dissolution medium: 50 mM Phosphate, pH 6.8

100 RPM Baskets

37° C.

Time points: 2, 4, 6, 8, 12, 16 or 24 hours

The blending and granulation of the hypromellose based formulation proceeded smoothly. The hypromellose formulation processed well, producing a final blend with excellent flow that compressed well on the tablet press. The yield was excellent (96%) for a small scale batch size.

The Poly Ethylene Oxide (Polyox) based formulation did not granulate as easily. The Polyox formulation was over-granulated. The over-granulation can be alleviated in the future by spraying less granulation water at a slower rate. An appreciable amount of the granulation was lost when the partially dried granulation was screened through a 4 mesh sieved to remove large over-granulated agglomerates that resisted drying in the fluid bed. As a result, the batch yield was poor at 83%. The portion of the batch that was retained produced an excellent final blend, however. It flowed and compressed well on the tablet process and produced good quality tablets. Polyox is known for being difficult to granulate so this is not entirely unexpected. However, with the proper granulation parameters an excellent granulation can be attained.

Physical data for sialic acid 325 mg final blends, sialic acid 325 mg tablets, and sialic acid 500 mg tablets are shown in Tables 9, 10 and 11, respectively. Analytical results for sialic acid 325 and 500 mg tablets (uncoated) are shown in Table 12.

TABLE 9

Physical data for Sialic Acid, 325 mg Final Blends:

|  | (ProCR Hypomellose) | (ProCR Polyox) |
|---|---|---|
| Sieve # (% Retain) Mesh size (um) | | |
| 14 (1400) | 0.10 | 1.32 |
| 30 (600) | 42.89 | 45.4 |
| 40 (425) | 12.28 | 14.39 |
| 140 (106) | 33.98 | 29.89 |
| 200 (75) | 5.42 | 3.24 |
| 325 (45) | 4.61 | 4.86 |
| Pan (<45) | 0.72 | 0.91 |
| Blend Bulk Density (g/mL) | 0.54.9 | 0.54.5 |
| Tap Density (g/mL) | 0.646 | 0.619 |
| % Compressibility | 15 | 12 |
| Flowdex | 10 | 6 |

TABLE 10

Physical Data of Sialic Acid 325 mg Tablets at Various Hardnesses

| Test | Formulation A | Formulation B Hypromellose | Formulation C | Formulation D | Formulation E Polyox | Formulation F |
|---|---|---|---|---|---|---|
| Tablet Hardness Level | Low | Medium | High/max | Low | Medium | High/max |
| Ave. Weight (mg) | 759.5 | 754 | 754 | 739 | 745 | 750 |
| Ave. Thickness (in) | 0.279 | 0.270 | 0.259 | 0.260 | 0.247 | 0.253 |
| Ave. Hardness (kp) | 6.5 | 10.0 | 14.4 | 9.5 | 17.9 | 15.7 |
| Ave. Friability (%) | Failed | 0.2 | 0.1 | 0.1 | 0.0 | 0.2 |

Note:
Average of 10 tablets

TABLE 11

Physical Data of Sialic Acid 500 mg Final Blends and Tablets

| Test | Formulation G | Formulation H Hypromellose | Formulation I | Formulation J | Formulation K Polyox | Formulation L |
|---|---|---|---|---|---|---|
| Bulk Density (g/mL) | | 0.55 | | | 0.54 | |
| Tablet Hardness Level | Low | Medium* | High/max | Low | Medium | High/max |
| Ave. Weight (mg) | 1170 | ND | 1152 | 1158 | 1154 | 1160 |
| Ave. Thickness (in) | 0.324 | ND | 0.315 | 0.310 | 0.307 | 0.297 |
| Ave. Hardness (kp) | 11.3 | ND | 13.2 | 12.9 | 14.0 | 20.2 |
| Ave. Friability (%) | 0.2 | ND | 0.0 | 0.1 | 0.0 | 0.0 |

Note:
Average of 10 tablets
*ND: not determined

TABLE 12

Analytical Results or Sialic Acid 325 mg and 500 mg SR Tablets (Uncoated)

| Test | Formulation C Hypromellose | Formulation F Polyox | Formulation I Hypromellose | Formulation K Polyox |
|---|---|---|---|---|
| Tablet Strength (mg) | 325 | 325 | 500 | 500 |
| Assay (% LC) | 96.3 | 97.8 | | |
| Impurities (%) | Total: 0.2 | Total: 0.2 | | |
| Dissolution (Average n = 3) % Release | | | | |
| 2 hr | 34 | 34 | 29 | 29 |
| 4 hr | 53 | 55 | 46 | 47 |
| 6 hr | 67 | 72 | 59 | 62 |
| 8 hr | 78 | 85 | 69 | 74 |
| 12 hr | 91 | 96 | 84 | 89 |
| 24 hr | 100 | 99 | 101 | 100 |

The dissolution results (FIG. 5) showed a first order sustained release profile over a 12 hour period for both dose strengths and for both ProCR hypromellose and ProCR Polyox. Additionally, these results indicate that the dose proportional approach was successful in providing dose flexibility using a common blend at 750 and 1154 tablet final weights.

Example 3

Coating for Sialic Acid 325 and 500 mg SR Tablets ProCR Hypromellose and ProCR Polyox Method of Manufacture Eight kilograms of core tablets (approximately 1.5 kg of active tablets combined with 6.5 kg of "sham" placebos to provided volume) were charged into an Accela-Cota coating equipment equipped with a 24" coating pan and two spray guns. The non-functional film coat was Opadry-II White (Colorcon Corporation formula Y-22-7719) at a 20% solids concentration. The purpose of the film coat was to improve aesthetics and in the future facilitate patient compliance for swallowing of the tablet. The target end-point was 3-5% weight gain.

The coating process parameters were as follows:
Pan speed: Target 12-16 rpm
Inlet temperature: 70-85° C.
Outlet temperature: 39-42° C.
Bed temperature: 33-45° C.
Atomization pressure: 40 psi
Spray Rate: 50-60 g/min
Airflow: approximately 200 cfm
Gun to bed distance: 5"

The tablets coated well with no difficulties. Approximately 4% weight gain of coating was sufficient to provide good coverage of the tablet cores.

Prototype Stability

Figure 6:
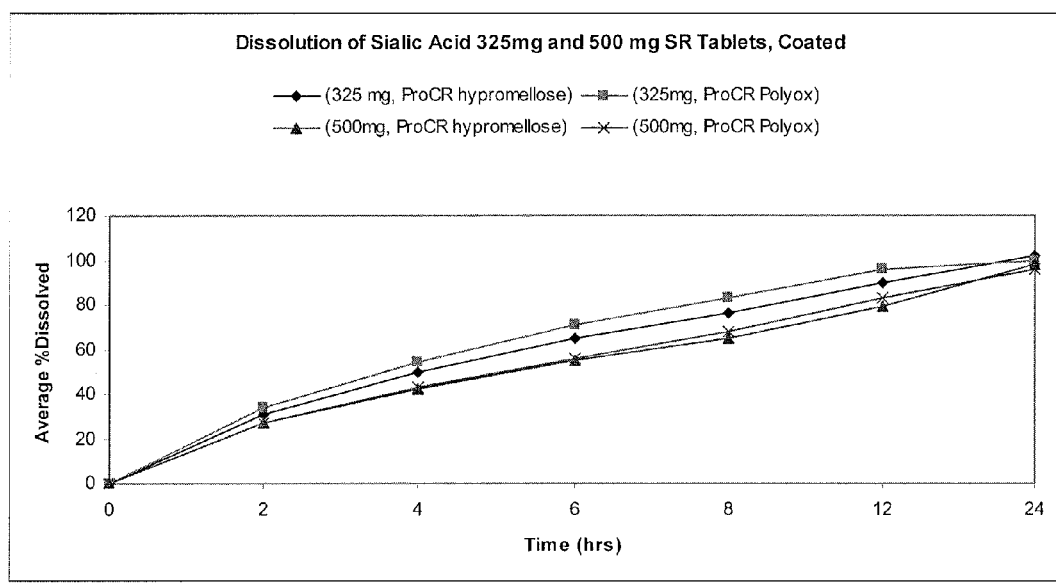
FIG. 6 shows the dissolution profile of sialic acid 325 and 500 mg sustained release (SR) coated tablets.

The white film coated tablets of Sialic Acid prepared using ProCR hypromellose and ProCR Polyox at 325 mg and 500 mg dose strengths were packaged in thirty (30) units per bottle, one MiniPax desiccant, no coil and induction sealed using a Lepak Jr™ induction cap sealing system. Table 13 lists the packaging components used. All the acceptable tablets were packaged and placed on a 12 month prototype stability program under ICH conditions testing the stability at both 25° C. and 60% relative humidity (RH) and 40° C. and 75% RH at 0, 1, 3, 6, and 12 months. The tablets have been tested and monitored with respect to appearance, dissolution, moisture, assay and related substances, and initial stability results are shown in Table 14. The dissolution profile for the coated 325 mg and 500 mg tablets is shown in FIG. 6.

TABLE 13

List of Packaging Components

| Component | Material Description | AAI RM # |
|---|---|---|
| Bottle | 100 cc Round White HDPE (38/400) | PC-3714 |
| Closure | 38 mm CRC w Foil Seal MI Liner | PC-3982 |
| Desiccant | MiniPax w 1.00 g Silica Gel-Packet | PC-2637 |

TABLE 14

Analytical Results of Sialic Acid 325 mg and 500 mg SR Tablets (Coated), Initial Stability

| Test | Formulation C Hypromellose | Formulation F Polyox | Formulation I Hypromellose | Formulation K Polyox |
|---|---|---|---|---|
| Tablet Strength (mg) | 325 | 325 | 500 | 500 |
| % Moisture by Karl Fischer | 1.0 | 3.3 | 2.0 | 3.7 |
| Content Uniformity | 100.0 | 95.6 | 99.8 | 98.6 |
| (Ave, n = 10) | | | | |
| % RSD | 1.5 | 2.5 | 1.5 | 2.6 |
| AV | 3.5 | 9.2 | 3.6 | 6.3 |
| Assay (% LC) | 100.6 | 97.8 | 98.8 | 96.9 |
| Impurities (%) | Total: <0.10 | Total: <0.10 | Total: <0.10 | Total: <0.10 |
| Dissolution (Ave. % Release, n = 6)) | | | | |
| 2 hr | 31 | 34 | 27 | 27 |
| 4 hr | 50 | 54 | 42 | 43 |
| 6 hr | 65 | 70 | 55 | 56 |
| 8 hr | 75 | 83 | 65 | 68 |
| 12 hr | 90 | 96 | 79 | 83 |
| 24 hr | 102 | 100 | 98 | 96 |

The formulation development activities successfully identified two distinct sustained release prototypes for Sialic Acid in 325 and 500 mg dose strengths. The in-vitro dissolution release profile exhibited a first order release over 12 hours in aqueous medium and pH of 6.8. The sustained release ProCR platform was employed. This unique combination of inert polymers provides a robust formulation that is pH independent and lends itself to granulation processes without affecting the dissolution release profile. This was the case for Sialic Acid 325 and 500 mg dose strength SR tablets where a wet granulation process was found necessary to achieve densification and good tablet compressibility.

With regard to chemical stability Sialic Acid 325 and 500 mg ProCR hypromellose and ProCR Polyox SR tablets showed acceptable assay, dissolution and content uniformity and easily passed USP testing criteria. These prototypes are monitored through a 12 month ICH stability study.

Figure 5:
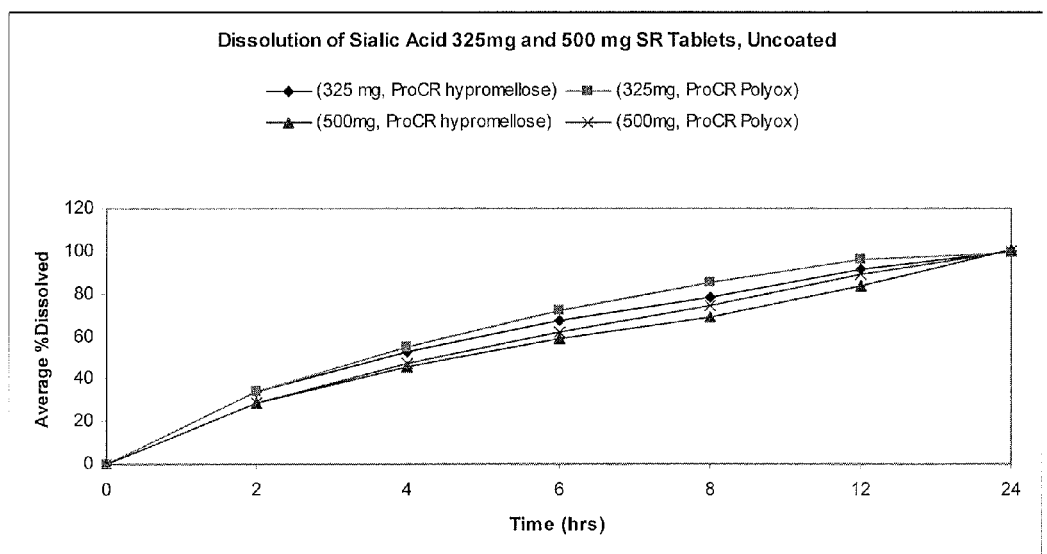
FIG. 5 shows the dissolution profile of sialic acid 325 and 500 mg sustained release (SR) uncoated tablets.

As shown in FIGS. 5 and 6, the dissolution profiles of Sialic Acid ProCR hypromellose and ProCR Polyox uncoated and coated tablets are consistent. There is no significant change in the sustained release profile over the 12 hour release with the application of Opdary® II White film coat. The analytical results for assay and related substances are acceptable which indicates that the wet granulation, drying and coating processes have no impact on the chemical integrity of the drug.

Example 4

Preparation of ManNAc 325 mg Development Prototypes

Figure 7:
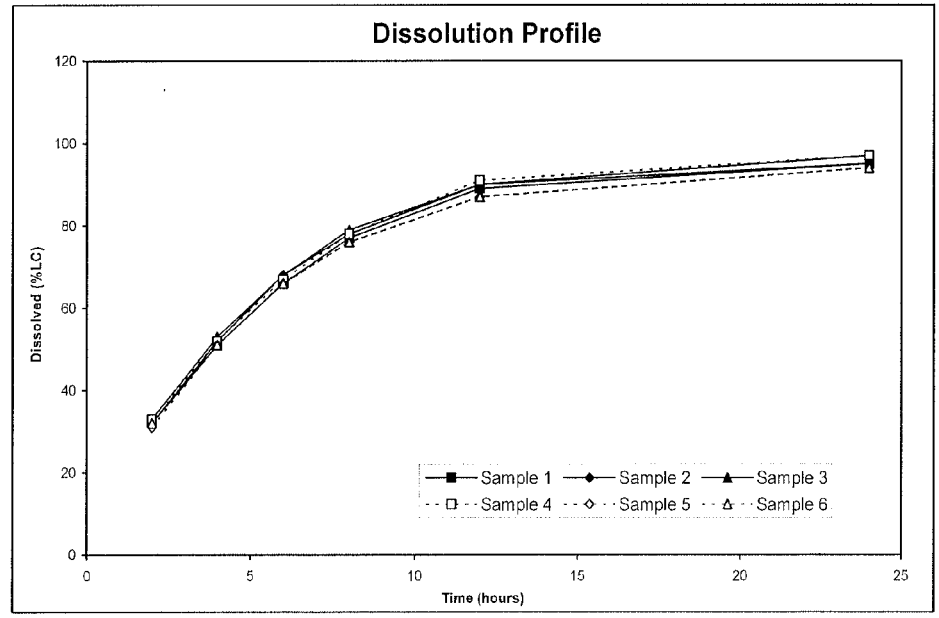
FIG. 7 shows the dissolution profile of ManNAc 325 mg tablets.
Figure 8A:
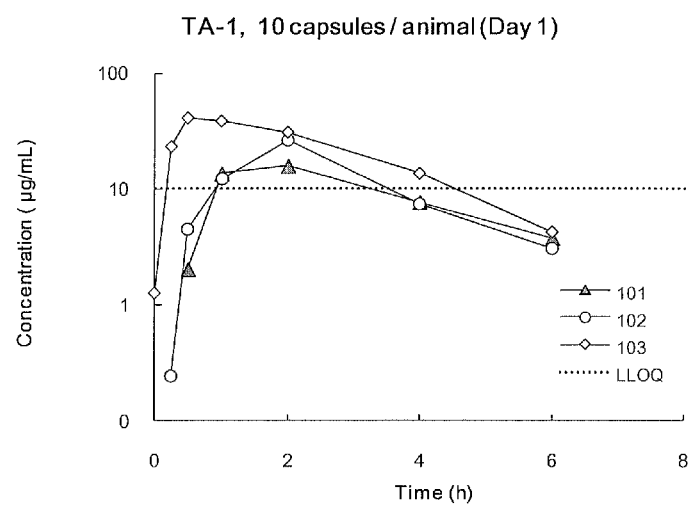
FIG. 8 shows the individual concentrations of sialic acid versus time in beagle dog serum following IV or oral administration. (A and B) concentration after administration of TA-1 capsules; (C) concentration after administration of TA-2 tablets; (D) concentration after administration of TA-3 tablet; (E) concentration after administration of TA-4 tablets; (F) concentration after administration of TA-5 tablets; (G and H) concentration after intravenous administration of TA-6.
Figure 8B:
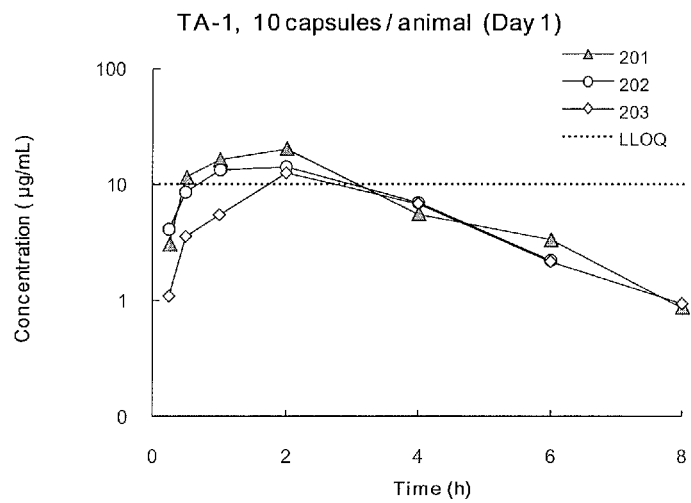
Figure 8C:
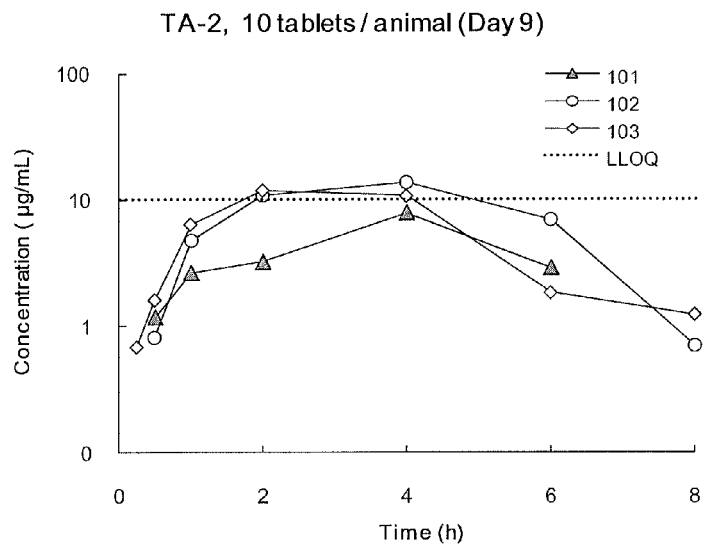
Figure 8D:
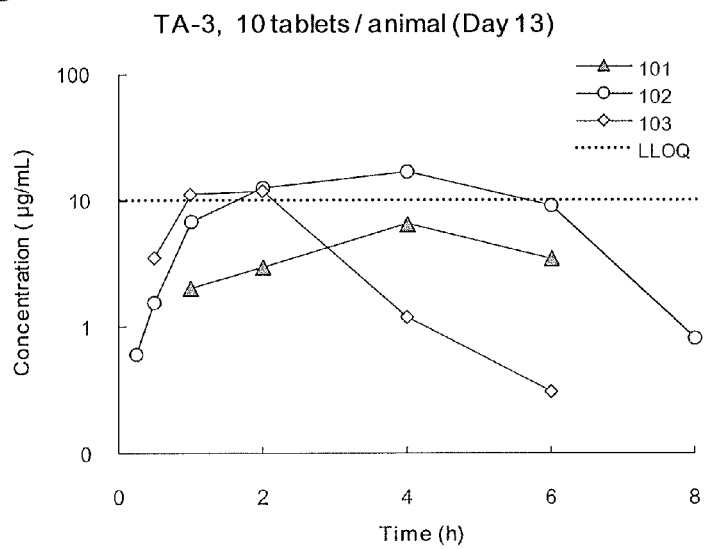
Figure 8E:
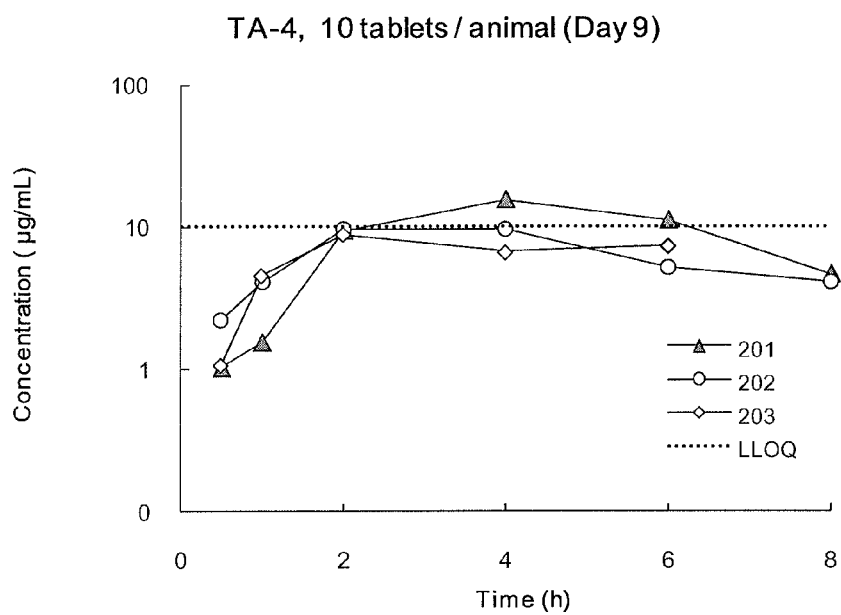
Figure 8F:
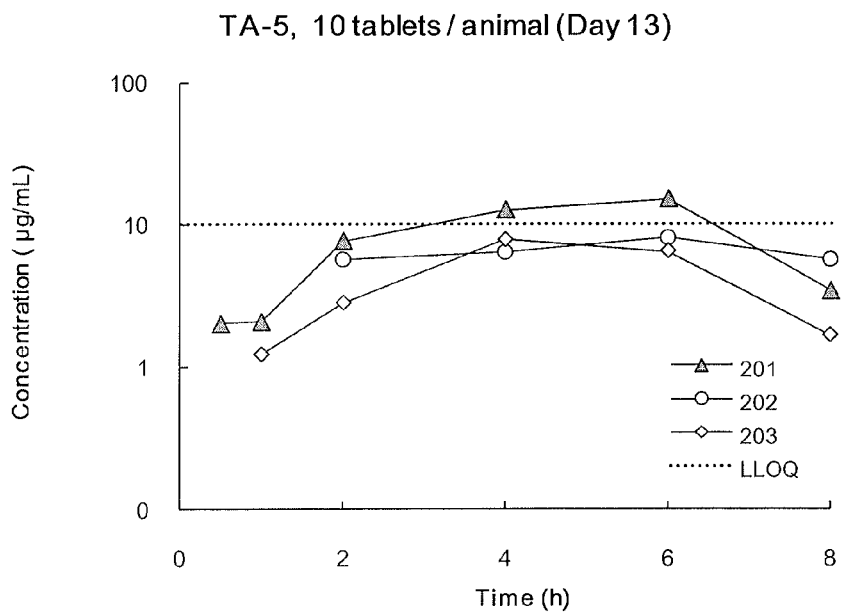
Figure 8G:
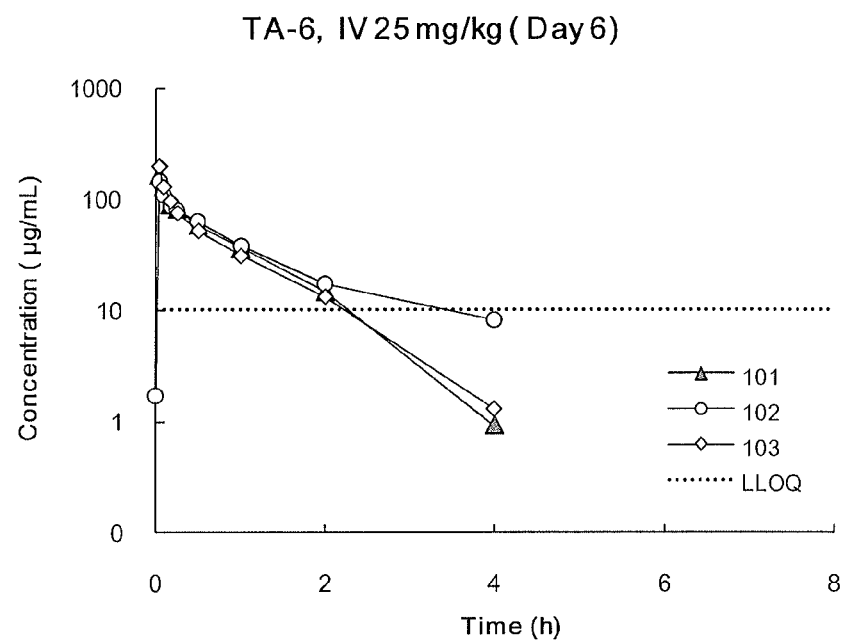
Figure 8H:
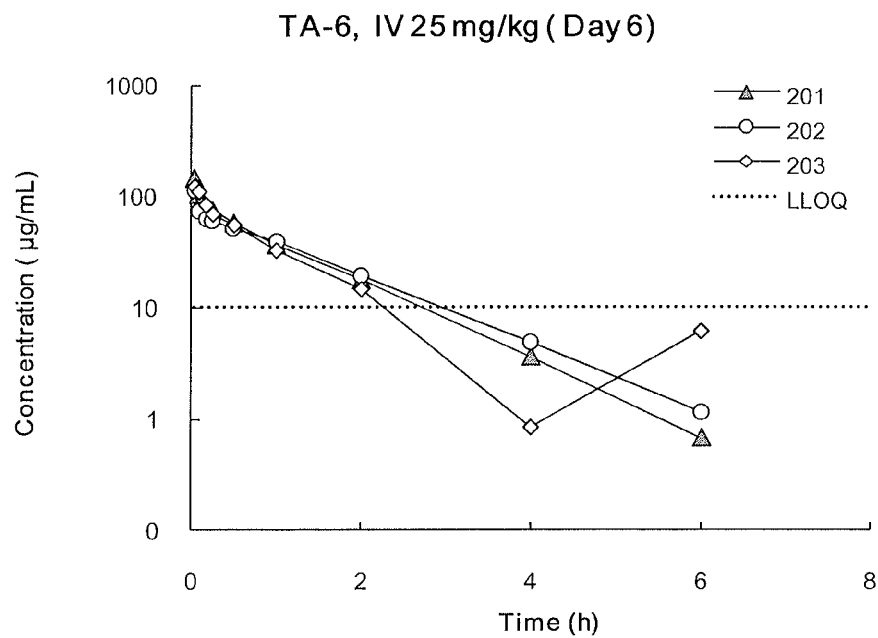
Figure 9:
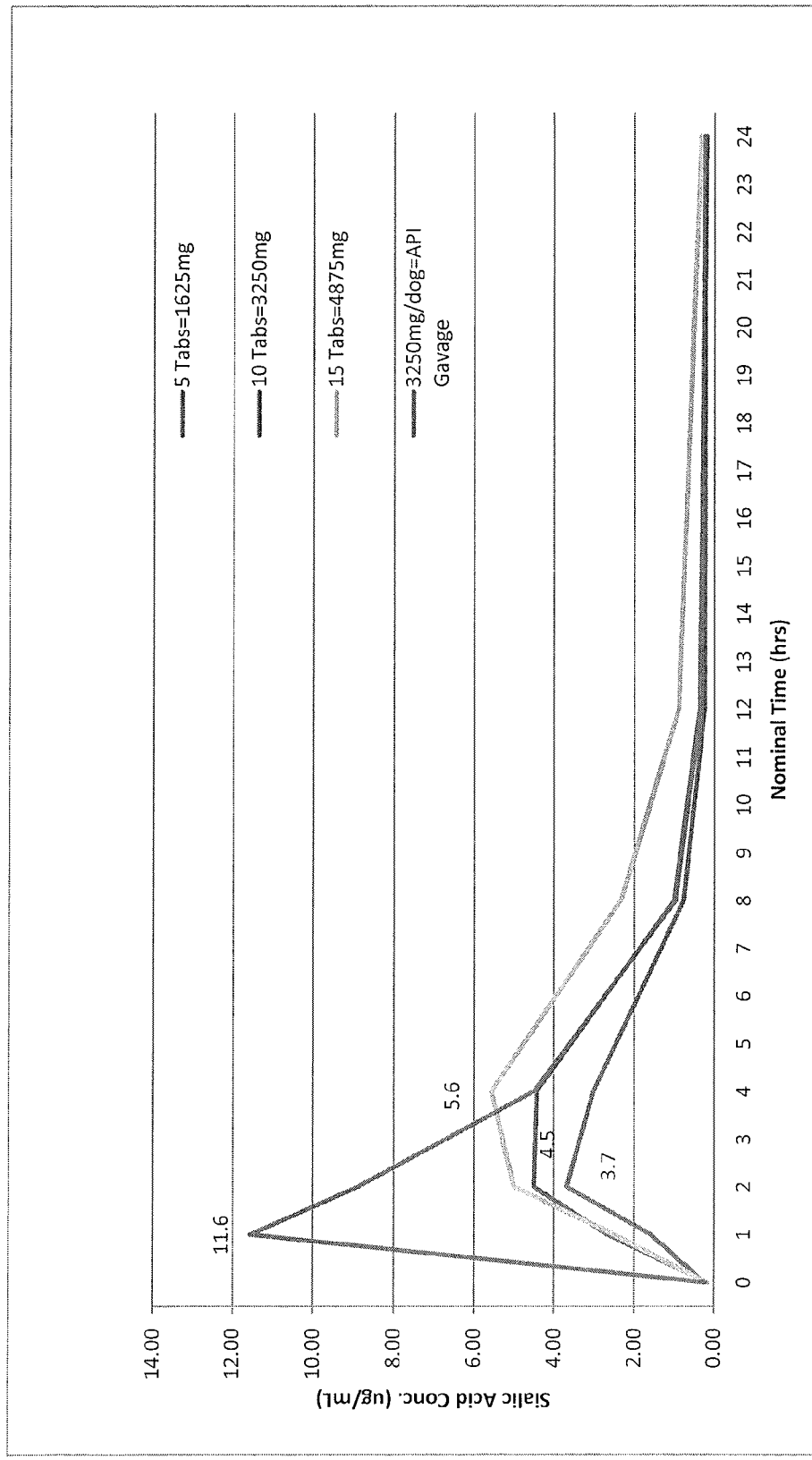
FIG. 9 shows pharmacokinetic data for single doses of SA-ER versus SA API in the canine-sialic acid in serum crossover study of orally administered SA-ER tablets.
Figure 10:
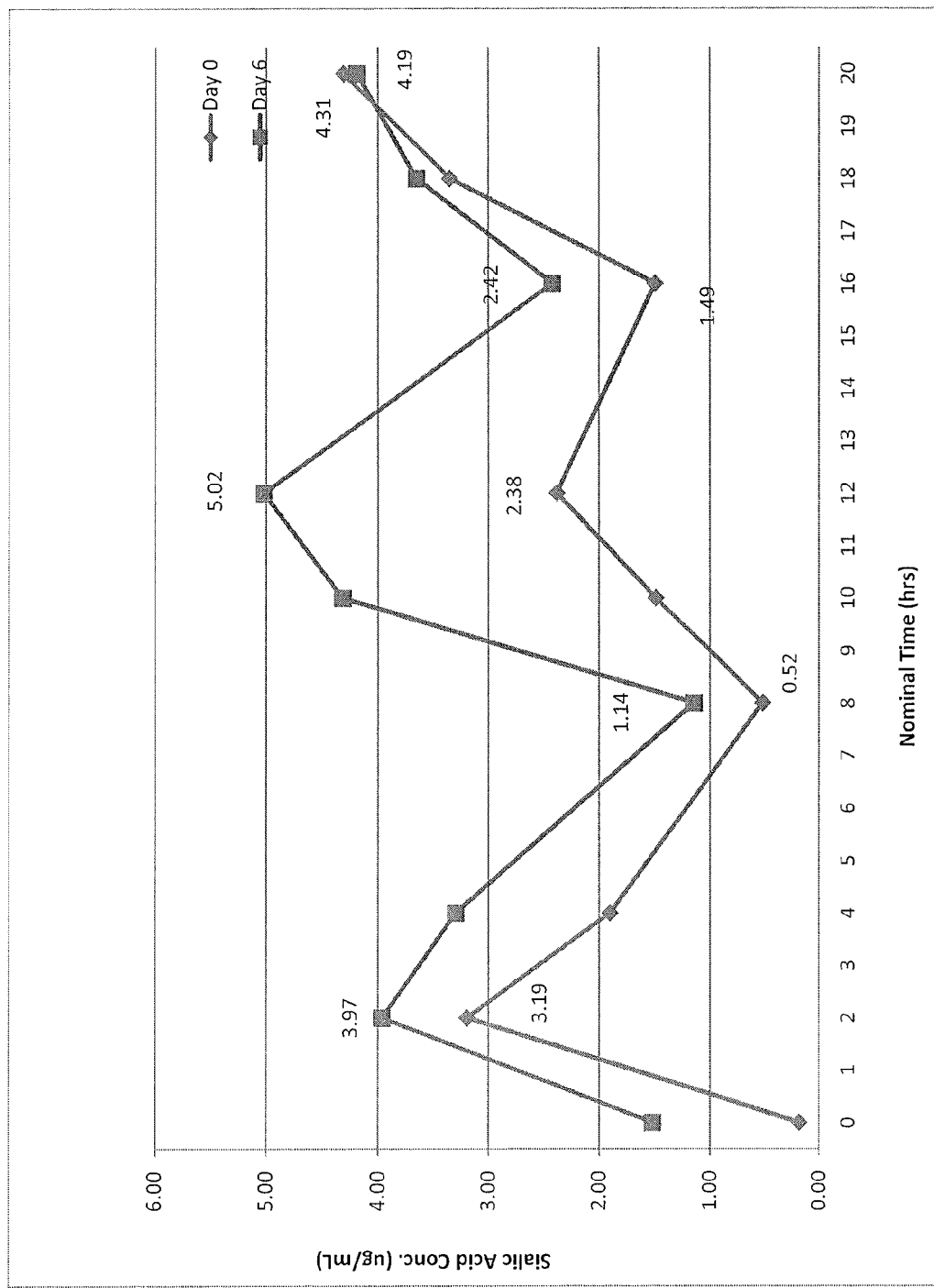
FIG. 10 shows results from repeated dosing of SA-ER in the dog: Day 0 to Day 7. Group average (Gp average) sialic acid concentration in serum orally administered SA-ER tablets (1625 mg TID). Some degree of accumulation occurred over the seven day period.
Figure 11:
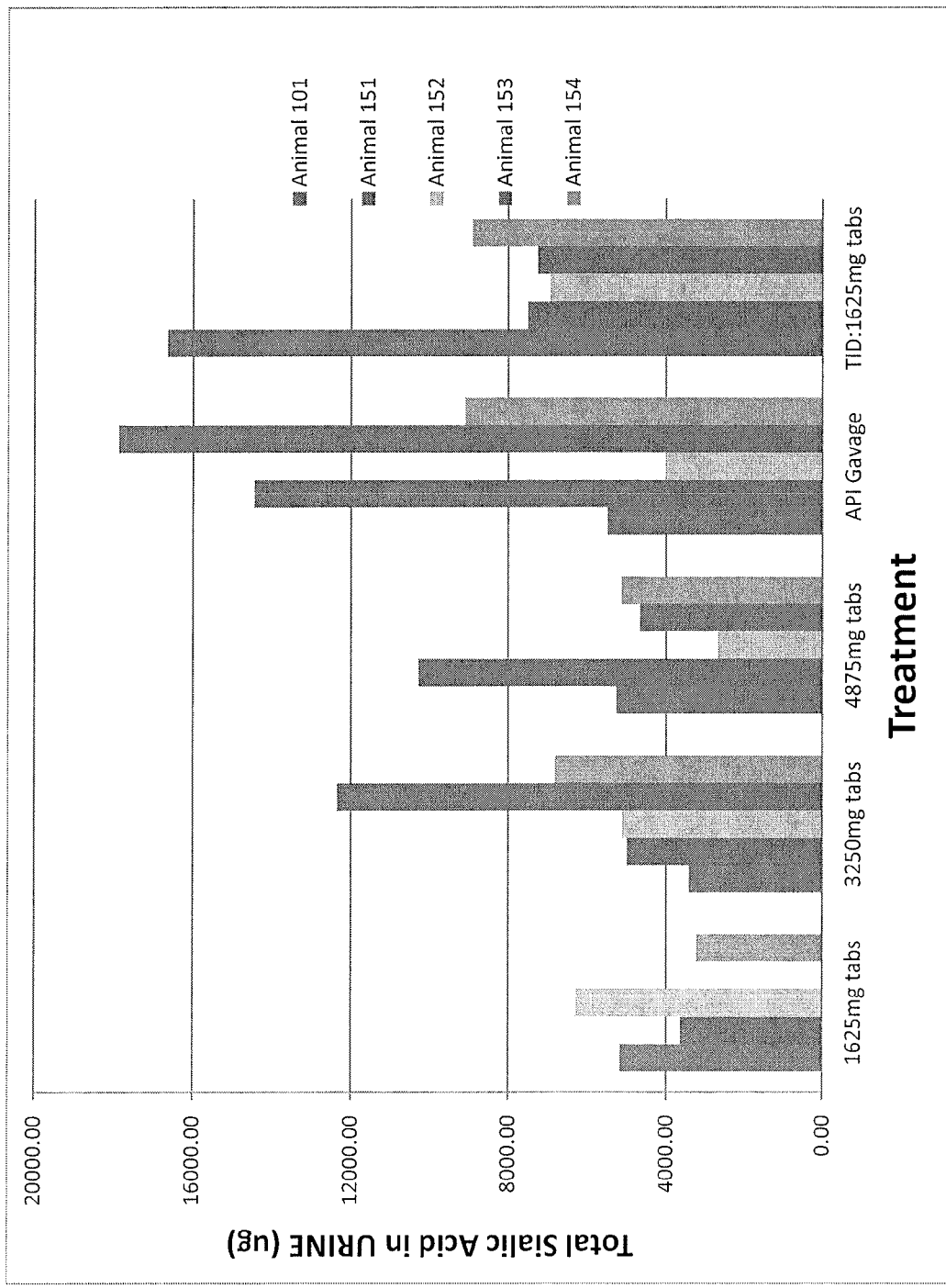
FIG. 11 shows a comparison of urinary SA excretion in a crossover study of orally administered SA-ER in the dog—individual canine excretion levels over a 24 hour period. Three orally administered dose levels versus API versus the last day of 7 days of dosing.
Figure 12:
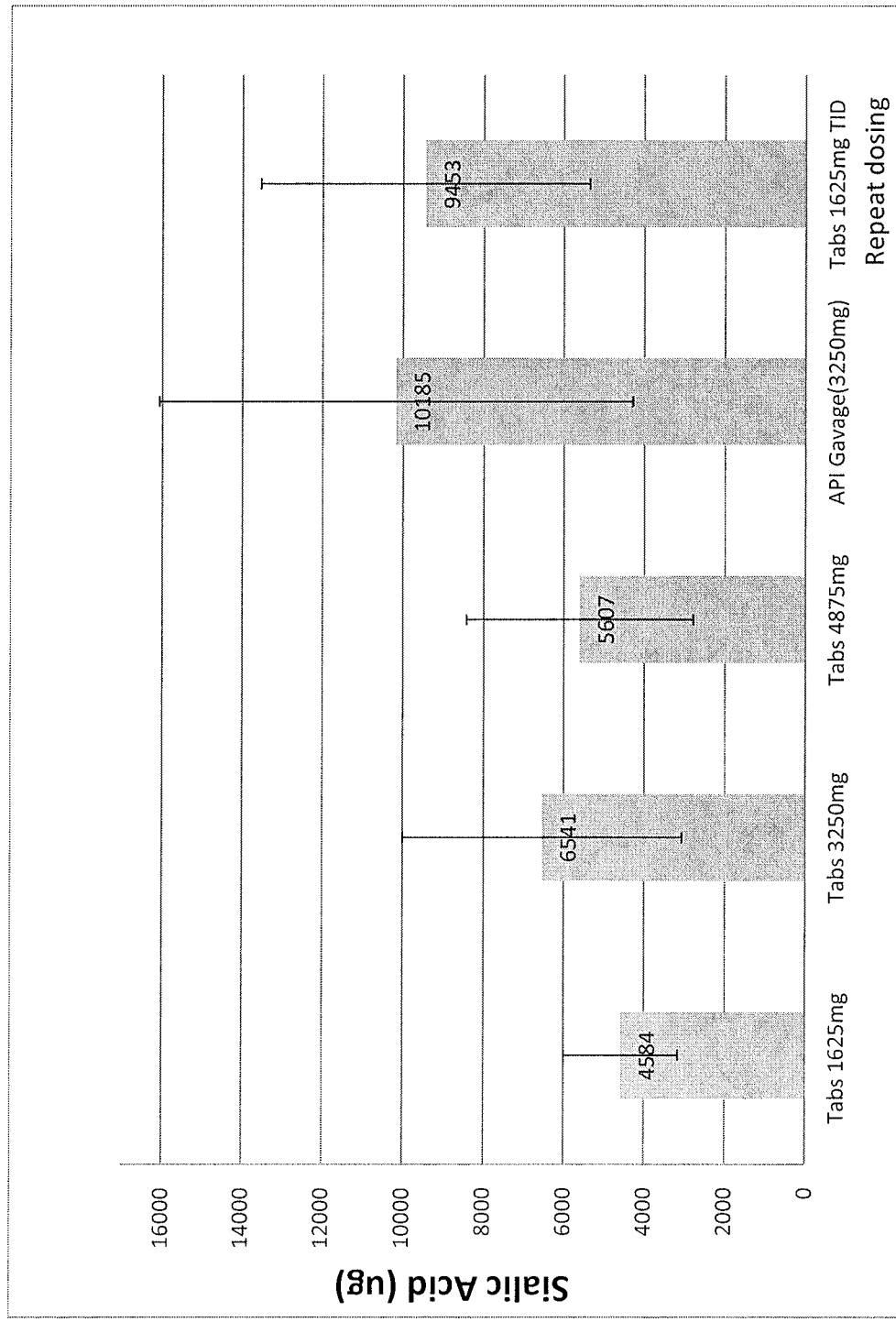
FIG. 12 shows a mean total urinary SA excretion comparison—total sialic acid in urine during 24 hours after/during dosing. Single doses, compared with API and with seventh day of repeat dosing.

The ManNAc title formulation was prepared according to the method detailed above for Sialic Acid. The dissolution profile of ManNAc 325 mg Tablets is shown in FIG. 7.
Core Tablet Results

| Assay | |
|---|---|
| % LC = | 93.5% |

| Impurity | % RS |
|---|---|
| Sialic Acid | <0.10% |
| Sodium Pyruvate | <0.10% |
| N-Acetyl-D-Glucosamine | 0.4% |
| Acetic Acid | <0.10% |
| Total | 0.4% |

| KF | |
|---|---|
| Prep | % water |
| 1 | 3.5 |
| 2 | 3.3 |
| Mean(2) | 3.4 |

| Content Uniformity | |
|---|---|
| Unit | % LC |
| 1 | 93.7 |
| 2 | 94.6 |
| 3 | 92.8 |
| 4 | 92.8 |
| 5 | 94.6 |
| 6 | 92.9 |
| 7 | 96.0 |
| 8 | 95.4 |
| 9 | 92.5 |
| 10 | 91.5 |

-continued

| Content Uniformity | |
|---|---|
| Unit | % LC |
| Mean (10) | 93.7 |
| % RSD | 1.5 |
| SD | 1.42735186 |
| AV | 8.2 |

Example 5

Pharmacokinetics of Sialic Acid Formulations Following a Single Oral or Intravenous Dose in Male Dogs The objective of this study was to evaluate the pharmacokinetics of sialic acid following single oral or intravenous dose in male dogs.

A total of six male beagle dogs (*Canis familiaris*), originally from Beijing Marshall Biotechnology Co., Ltd., were obtained from the PCS-SHG colony and subjected to a general physical examination to ensure normal health status before study initiation. All animals were considered suitable for use and each animal was uniquely identified by a permanent skin tattoo number and/or letter on the ventral aspect of one pinna. An acclimation period of five days was allowed between animal transfer and the start of treatment in order to accustom the animals to the laboratory environment.

Before dosing initiation, all animals were weighed and assigned to treatment groups. At the start of treatment, animals were 7-16 months of age and ranged in weight as 6.4 to 9.4 kg. Animals were housed individually in stainless steel cages equipped with a mesh-type floor and an automatic watering valve. A standard certified pelleted commercial dog food (approximately 400 g of Certified Canine Diet 5C07, PMI Nutrition International, Inc.) was provided to each animal once daily, except during designated procedures. Maximum allowable concentrations of contaminants in the diet (e.g., heavy metals, aflatoxin, organophosphates, chlorinated hydrocarbons, PCBs) were controlled and routinely analyzed by the manufacturers. It was considered that there were no known contaminants in the food that could have interfered with the objectives of the study. Municipal tap water, which was softened, purified by reverse osmosis and exposed to ultraviolet light, was freely available except during designated procedures. It was considered that there were no known contaminants in the water that could have interfered with the objectives of the study. Each Animal was provided with a floor toy, except during designated activities.

The study design was as shown in Table 15:

TABLE 15

| Experimental Design | | | | | | | | |
|---|---|---|---|---|---|---|---|---|
| Group No. | Study Day | Test Article | Treatment[a] | Dose Level[#] (mg/kg) | Number of Tablets per animal | Dose Volume (mL/kg) | Dose Concentration (mg/mL) | Animal Number |
| 1 | 1 | TA-1 (capsule) | PO | — | 10 | — | — | 3 |
| | 6 | TA-6 | IV | 25 | — | 0.5 | 50 | |
| | 9 | TA-2 (tablet) | PO | — | 10 | — | — | |
| | 13 | TA-3 (tablet) | PO | — | 10 | — | — | |

TABLE 15-continued

Experimental Design

| Group No. | Study Day | Test Article | Treatment[a] | Dose Level[#] (mg/kg) | Number of Tablets per animal | Dose Volume (mL/kg) | Dose Concentration (mg/mL) | Animal Number |
|---|---|---|---|---|---|---|---|---|
| 2 | 1 | TA-1 (capsule) | PO | — | 10 | — | — | 3 |
|   | 6 | TA-6 | IV | 25 | — | 0.5 | 50 |   |
|   | 9 | TA-4 (tablet) | PO | — | 10 | — | — |   |
|   | 13 | TA-5 (tablet) | PO | — | 10 | — | — |   |

— = not applicable.
[#] Dose level was expressed as free form.
[a] Animals were fasted overnight for approximately 16 hours prior to each dose and were fed immediately after the 6 hr timepoint.

The first day of dosing was designated as Day 1. The subsequent dosing days were Days 6, 9 and 13. On Days 1, 9 and 13, all animals were orally administered prepared capsules or tablets. On Day 6, all animals received a single intravenous dose of TA-6 at 0.5 mL/kg. Each actual volume of TA-6 administered was based on the most recent practical body weight of each animal. The test articles 1 through 6 are specified in Table 16.

TABLE 16

Specification of Test Articles

| Test Article | Identification | Compositon/Concentration | Dose Level | Animal Number |
|---|---|---|---|---|
| TA-1 | API in Capsule Form | 325 mg SA per capsule | 3250 mg SA per animal | 101-103, 201-203 |
| TA-2 | Sialic Acid Delayed Release Tablet Formulation I | 325 mg SA/425 mg excipient (hypromellose) per tablet | 3250 mg SA per animal | 101-103 |
| TA-3 | Sialic Acid Delayed Release Tablet Formulation II | 325 mg SA/425 mg excipient (polyethylene oxide) per tablet | 3250 mg SA per animal | 101-103 |
| TA-4 | Sialic Acid Delayed Release Tablet Formulation III | 500 mg SA/650 mg excipient (hypromellose) per tablet | 5000 mg SA per animal | 201-203 |
| TA-5 | Sialic Acid Delayed Release Tablet Formulation IV | 500 mg SA/650 mg excipient (polyethylene oxide) per tablet | 5000 mg SA per animal | 201-203 |
| TA-6 | Sialic Acid IV Formulation | 50 mg/mL | 25 mg/kg SA | 101-103, 201-203 |

Individual body weights were measured once during the predose period and prior to each dose on dosing days. There were no treatment-related clinical signs observed during the study period and no treatment related changes in body weight or body weight gains noted for any animal during the study period.

Blood samples were collected into serum separate tubes from all animals on Days 1, 6, 9, 13 for processing to serum at the following time points: predose, 2 minutes (i.v. only), 5 minutes (i.v. only), 10 minutes (i.v. only), 15 minutes, 30 minutes, 1, 2, 4, 6, 8 and 24 hours postdose. Urine samples were collected into jars on wet ice or ice packs from all animals on Days 1, 6, 9, 13 at the following time intervals: predose (overnight for approximate 15 hours), 0 to 4, 4 to 8, 8 to 12 hours postdose. Samples were collected according to Table 17 and Table 18:

TABLE 17

PK Sample Collection Schedule

| Group No. | Sample Collection Time Points (Time Post Dose) on Days 1, 6, 9 and 13 | | | | | | | | | | | |
|---|---|---|---|---|---|---|---|---|---|---|---|---|
|  | 0 min[a] | 2 min | 5 min | 10 min | 15 min | 30 min | 1 hr | 2 hr | 4 hr | 6 hr | 8 hr | 24 hr |
| 1 | X | X (IV only) | X (IV only) | X (IV only) | X | X | X | X | X | X | X | X |

TABLE 17-continued

PK Sample Collection Schedule

| Group No. | Sample Collection Time Points (Time Post Dose) on Days 1, 6, 9 and 13 | | | | | | | | | | | |
|---|---|---|---|---|---|---|---|---|---|---|---|---|
| | 0 min[a] | 2 min | 5 min | 10 min | 15 min | 30 min | 1 hr | 2 hr | 4 hr | 6 hr | 8 hr | 24 hr |
| 2 | X | X (IV only) | X (IV only) | X (IV only) | X | X | X | X | X | X | X | X |

X = sample collected
[a]Samples were collected before dosing.

TABLE 18

Urine Sample Collection Schedule

| Group No. | Sample Collection Time Points (Time Post Dose) on Days 1, 6, 9 and 13 | | | |
|---|---|---|---|---|
| | Overnight[a] | 0-4 hr | 4-8 hr | 8-12 hr |
| 1 | X | X | X | X |
| 2 | X | X | X | X | x = sample collected
[a]Blank urine were collected overnight (approximate 15 hours) before each dose.

Blood samples were placed at room temperature for at least 30 minutes but no more than 1 hour to clot prior to refrigerated centrifugation (approximately 4° C.) at approximately 2700 rpm for 10 minutes. The serum separated from each sample was transferred into polypropylene tubes and placed on dry ice until transferred to a freezer (set to maintain −80° C.). Urine samples were stored in a freezer (set to maintain −80° C.) until analyzed.

Drug concentrations in serum and urine were determined by LC MS/MS using a validated analytical procedure (Validation of a Method for the Determination of Free Soluble Sialic Acid in Dog Serum and Urine by Liquid Chromatography-Tandem Mass Spectrometry (LC-MS/MS)-PN 102653; Long-term Matrix Stability Assessment of Free Soluble Sialic Acid in Dog Serum and Urine by Liquid Chromatography-Tandem Mass Spectrometry (LC-MS/MS)-PN 102654. The method had a linear range from 10-1000 µg/mL and the lower limit of quantitation was 10 µg/mL.

Data collection was performed using Analyst® from AB Sciex. Statistical analyses including regression analysis and descriptive statistics including arithmetic means and standard deviations, accuracy and precision were performed using Watson™ Laboratory Information Management System (LIMS) and Microsoft Excel.

Pharmacokinetic parameters were estimated using Win-Nonlin® pharmacokinetic software (Version 5.2.1, Pharsight Corp., Mountain View, Calif., USA). A non-compartmental approach consistent with the intravenous or oral route of administration was used for parameter estimation. All parameters were generated from individual sialic acid concentrations in serum. Parameters were estimated using nominal sampling times relative to the start of each dose administration. Mean concentrations were derived from 3 animals/group/time point for intravenous dosing occasion only. The actual timepoints were within the range of protocol specified. Serum concentration values obtained at the predose time point were used as the concentration at time zero for oral doses. The actual dose levels of test articles 1 through 5 were calculated using the total amount of SA given to each animal based on their most practical body weight.

The area under the sialic acid individual serum concentration versus time curve (AUC) was calculated using the linear trapezoidal method with linear interpolation. The terminal elimination phase of each individual concentration versus time curve was identified using at least the final three observed concentration values. The slope of the terminal elimination phase was determined using log linear regression on the unweighted concentration data. The terminal elimination phase related parameters were not reported if the coefficient of determination was less than 0.800, or the extrapolation of the AUC to infinity represented more than 20% of the total area, or the terminal elimination phase could not be identified. The parameters described in Table 19 were observed or calculated.

All data from serum including concentrations below LLOQ (except for those below zero) were applied to pharmacokinetic analysis.

TABLE 19

Estimated Parameters from Serum Concentrations of Sialic Acid

| Parameters | Description of parameter |
|---|---|
| Cmax | The maximum observed arithmetic individual concentration of sialic acid after dosing. |
| Tmax | The time after dosing when the maximum observed arithmetic individual concentration of sialic acid was observed. |
| AUC (0-t) | The area under the sialic acid arithmetic individual concentration versus time curve from time zero to the time after dosing when the last quantifiable concentration of the drug was observed. |
| MRT (0-t) | The mean residence time of sialic acid estimated from time zero to the time after dosing at which the last quantifiable concentration of the drug was observed estimated or imputed by the linear or linear/log trapezoidal method. |
| T½ | The apparent terminal elimination half life. |
| AUC (0-inf) | The area under the arithmetic individual concentration versus time curve from time zero to infinity. |
| MRT (0-inf) | The mean residence time estimated from time zero to infinity. |
| CL (IV only) | Clearance: the apparent volume of serum cleared of sialic acid per unit time following intravenous dosing. Clearance was calculated for intravenous dose only. |
| Vd (IV only) | The apparent volume of distribution of sialic acid, determined from the terminal elimination phase following intravenous dosing. Volume of distribution was calculated for intravenous dose only. |
| Fs | Absolute bioavailability based on sialic acid levels in the serum following IV and oral administration. |

Urinary concentrations of sialic acid were subjected to calculation using Microsoft® Excel, 2007. All data from urine including concentrations below LLOQ (except for those below zero) were applied.

The data of predose urine samples were applied to calculate the total increase in urinary excretion of sialic acid at 12 hours postdose. The urinary excretion of sialic acid, as a percent of dose administered was estimated for each dosing occasion. Based on the assumption that the amount of drug excreted in urine after oral administration was a reflection of the dose absorbed, the bioavailability of sialic acid was determined based on the percent excretion value following IV and oral administration.

The parameters described in Table 20 were observed or calculated.

TABLE 20

Estimated Parameters from Urine Concentrations of Sialic Acid

| Parameters | Description of parameter |
| --- | --- |
| Dose | The amount of SA dosed per animal contained in each test article. |
| Mass Excreted (0-12 hr) | The total mass of urinary excretion of sialic acid at 12 hours postdose. |
| Mass Excreted (0-12 hr)-Corrected | The corrected value calculated by subtracting out the background masses based on predose data, representing the increase in urinary excretion of sialic acid at 12 hours postdose. If corrected value was less than zero, the value was set to zero. |
| Percent Excretion (0-12 hr) | The corrected mass excreted of sialic acid as a percent of dose administered. |
| Fu | Bioavailability based on the sialic acid levels in the urine following IV and oral administration. |

There were no treatment-related clinical signs noted following either oral or intravenous administration of sialic acid over the study period. Skin red was noted for Animal Nos. 201 and 203 during the study, which was considered as incidental.

There were no treatment related changes in body weight or body weight gains noted for any animal during the study period. Any differences in body weight or body weight gain were likely related to expected biological variation.

Individual concentrations of sialic acid versus time in Beagle dog serum following IV or oral administration are shown in FIGS. 8A-8H.

TA-1

The background sialic acid levels were below zero for predose samples of five of the six animals, except for Animal No. 103, of which was slightly above zero but below 20% of the LLOQ.

Following oral administration of TA-1 in prepared capsules at 3250 mg of SA per animal, peak concentrations were observed ranging from 12.6 to 40.8 µg/mL. $T_{max}$ was observed at 2 hours postdose with the exception of Animal No. 103 (0.5 hours). The concentrations of sialic acid decreased to levels below zero at 24 hours postdose for all six animals. The concentration of Animal No. 201 at 24 hour postdose (22.0989 µg/mL) was considered as aberrant and excluded from analysis, as it was a >LLOQ value but following three <LLOQ samples which followed three quantifiable concentrations in the sampling sequence.

Towards the end of the sampling period, a decrease in sialic acid concentrations was apparent, but the terminal elimination half-life could only be calculated for Animal Nos. 103, 201 and 203, ranging from 1.39 to 1.49 hours.

The bioavailability of TA-1 was estimated to be ranging from 2.73% to 6.76%, based on the individual AUC(0-t) value following IV and oral administration.

All the predose urine samples had a measureable concentration of sialic acid while the data varied for each individual, ranging from 8.16 to 25.1 µg/mL. The maximum excretion of sialic acid was observed for samples collected 4-8 hours postdose, except for Animal No. 202 (0-4 hours postdose). The total mass of sialic acid excreted in the urine was equivalent to 0.43-3.56% of the doses of SA contained in TA-1.

The bioavailability of TA-1 was estimated to be ranging from 1.29% to 39.1% based on the individual urinary percent excretion value following IV and oral administration.

TA-2

The background sialic acid levels were below zero for predose samples of Animal Nos. 102 and 103 except for Animal No. 101, of which was slightly above zero but below 20% of the LLOQ.

Following oral administration of TA-2 in prepared tablets at 3250 mg of SA per animal, $T_{max}$ was observed from 2.00 to 4.00 hours postdose with the peak concentrations ranging from 7.98 to 13.7 µg/mL. The concentrations of sialic acid generally decreased after $T_{max}$ to levels below zero at 24 hours postdose, for all dosed animals. The elimination half life of sialic acid was estimated to be 1.28 hour in Animal No. 103. For Animal Nos. 101 and 102, the half-life could not be estimated as the measurable data were not enough to identify the termination elimination phase.

The oral bioavailability of TA-2 was estimated to be ranging from 1.64% to 3.25%, based on the individual AUC(0-t) value following IV and oral administration.

All the predose urine samples had a measureable concentration of sialic acid ranging from 13.5 to 34.8 µg/mL. The maximum excretion of sialic acid was observed for samples collected 4-8 hours postdose for all animals. The total increase of sialic acid excreted in the urine postdose was equivalent to 1.08-3.20% of the doses of SA contained in TA-2.

The bioavailability of TA-2 was estimated to be 2.53% and 3.73% for Animal Nos. 102 and 103, respectively, based on the individual urinary percent excretion value following IV and oral administration. The bioavailability is 97.4% for Animal No. 101, which was markedly higher than the other two animals due to its low percent excretion value of IV doses.

TA-3

The background sialic acid levels were below zero for predose samples of all three animals.

Following oral administration of TA-3 in prepared tablets at 3250 mg of SA per animal, $T_{max}$ was observed from 2.00 to 4.00 hours postdose with the peak concentrations ranging from 6.52 to 17.0 µg/mL. The concentrations of sialic acid generally decreased after $T_{max}$ to levels below zero at 24 hours postdose for all three animals. However, the half-life could not be estimated for the three animals as the measurable data were not enough to identify the termination elimination phase or the extrapolation of the AUC to infinity represented more than 20% of the total area.

The oral bioavailability of TA-3 was estimated to be ranging from 1.46% to 4.14%, based on the individual AUC(0-t) value following IV and oral administration.

Concentrations of sialic acid of all the predose urine samples were noted to be slightly above LLOQ, ranging from 10.1 to 11.2 µg/mL. The maximum excretion of sialic acid was observed for samples collected 4-8 hours postdose for Animal Nos. 102 and 103, and 8-12 hours postdose for Animal No. 101, respectively. The total increase of sialic acid excreted in the urine postdose was equivalent to 0.94-2.99% of the doses of SA contained in TA-3.

The bioavailability of TA-3 was estimated to be 3.49% and 1.51% for Animal Nos. 102 and 103, respectively, based on the individual urinary percent excretion value following IV and oral administration. The bioavailability is 85.0% for Animal No. 101, which was markedly higher than the other two animals due to its low percent excretion value of IV doses.

TA-4

In animals treated with TA-4, no sialic acid was measureable beyond 30 minutes postdose.

Following oral administration of TA-4 in prepared tablets at 5000 mg of SA per animal, most of the concentrations of sialic acid were below LLOQ with the exception of one dog (Animal No. 201), where the concentrations were slightly above LLOQ at 4 and 6 hours postdose. $T_{max}$ was observed from 2.00 to 4.00 hours postdose with the peak concentrations ranging from 8.97 to 15.7 μg/mL. The concentrations of sialic acid generally decreased after $T_{max}$ to levels below zero at 24 hours postdose for all dosed animals. The half-life could not be estimated as the measurable data were not enough to identify the termination elimination phase.

The oral bioavailability of TA-4 was estimated to be ranging from 1.57% to 2.09%, based on the individual AUC(0-t) value following IV and oral administration.

All the predose urine samples had a measureable concentration of sialic acid ranging from 6.4 to 42.6 μg/mL. The maximum excretion of sialic acid was observed for samples collected 8-12 hours postdose for Animal Nos. 201 and 203, and 0-4 hours for Animal No. 202, respectively. The total increase of sialic acid excreted in the urine postdose was equivalent to 0.54-1.93% of the doses of SA contained in TA-4.

The bioavailability of TA-4 was estimated to be 1.42% and 2.55% for Animal Nos. 202 and 203 based on the individual urinary percent excretion value following IV and oral administration. The bioavailability of Animal No. 101 could not be estimated as the mass excreted of sialic acid postdose was set to be zero when corrected by predose data.

TA-5

The background sialic acid levels of all animals were below zero for both predose samples and 15 minutes postdose.

Following oral administration of TA-5 in prepared tablets at 5000 mg of SA per animal, most of the concentrations of sialic acid were below LLOQ with the exception of Animal No. 201, of which were slightly above LLOQ at 4 and 6 hours postdose. $T_{max}$ was observed from 4.00 to 6.00 hours postdose with the peak concentrations ranging from 7.79 to 15.3 μg/mL. The concentrations the sialic acid generally decreased to levels below zero at 24 hours postdose for all three animals. However, the half-life could not be estimated for the three animals as the measurable data were not enough to identify the termination elimination phase.

The oral bioavailability of TA-5 was estimated to be ranging from 1.47% to 1.96%, based on the individual AUC(0-t) value following IV and oral administration.

Concentrations of sialic acid of all the predose urine samples ranged from 2.27 to 23.6 μg/mL. The maximum excretion of sialic acid was observed for samples collected 4-8 hours postdose for Animal Nos. 202 and 203, and 0-4 hours postdose for Animal No. 201, respectively. The total increase of sialic acid excreted in the urine postdose was equivalent to 0.02-1.70% of the doses of SA contained in TA-5.

The oral bioavailability of TA-5 was estimated to be 0.52% and 2.24%, for Animal Nos. 202 and 203, respectively, based on individual urinary percent excretion value following IV and oral administration. The bioavailability of Animal No. 101 could not be estimated as the mass excreted of sialic acid postdose was set to be zero when corrected by predose data.

TA-6

The serum levels of sialic acid were below zero for predose samples of most animals except for one dog, Animal No. 102, of which was slightly above zero but below 20% of the LLOQ.

Following an intravenous dose of 25 mg/kg of TA-6, the concentrations of sialic acid decreased quickly to levels below LLOQ at the timepoint of 4 hours postdose, and then to levels below zero at the timepoint of 8 hours postdose, for all six animals. The concentrations generally declined in animals, except that Animal No. 203 exhibited much higher concentrations at 6 hours postdose when compared to the previous time point. Sialic acid was eliminated in dogs with the half lives ranging from 0.56 to 1.40 hours.

The concentrations of sialic acid in the urine varied between each animal. It was noted that the sialic acid levels in urine collected postdose were lower than predose for Animal No. 201, with two of the three concentrations of postdose samples detected as below zero.

The IV dose resulted in 72.4-87.7% of the administered dose being excreted in the urine of five of the six animals. One dog (Animal No. 101) demonstrated excretion of only 1.1% of the applied dose.

The individual urinary percent excretion of TA-6 was used to adjust the data of oral doses to account for the fraction of sialic acid absorbed (Fu, %). From the data reported herein, Animal No. 101 were observed to have much lower urinary excretion postdose after IV dose, which resulted in a markedly higher value of bioavailability estimated for its oral doses when compared with other animals in the same group.

In summary, after oral administration of TA-1 through TA-5, low sialic acid levels were detected in serum, most of which fell below the limit of quantitation. Peak concentrations ranging from 6.52 to 40.8 μg/mL were observed from 0.5 to 6 hours postdose. Sialic acid was eliminated with a half-life of 0.56 to 1.40 hours, calculated based on the serum concentration data from intravenous dose of TA-6. The bioavailability was estimated based on the individual AUC (0-t) value following IV and oral administration. The pharmacokinetic parameters estimated for sialic acid in serum are presented in Table 21 to Table 23.

TABLE 21

Pharmacokinetic parameters estimated for sialic acid in serum

| Test Article | Dose Level (mg/kg) | Animal Number | Range | | | |
|---|---|---|---|---|---|---|
| | | | Cmax (μg/mL) | Tmax (h) | AUC(0-t) (μg * h/mL) | Fs (%) |
| TA-1 | 353-445 | 101-103 | 15.8-40.8 | 0.5-2 | 54.1-128 | 3.43-6.76 |
| | 346-508 | 201-203 | 12.6-20.5 | 2 | 43.5-66.7 | 2.73-3.20 |
| TA-2 | 361-451 | 101-103 | 7.98-13.7 | 2-4 | 26.5-62.4 | 1.64-3.25 |
| TA-3 | 353-439 | 101-103 | 6.52-17.0 | 2-4 | 23.1-77.6 | 1.46-4.14 |
| TA-4 | 538-746 | 201-203 | 8.97-15.7 | 2-4 | 38.3-74.4 | 1.57-2.09 |
| TA-5 | 543-781 | 201-203 | 7.79-15.3 | 4-6 | 35.7-73.6 | 1.47-1.96 |
| TA-6 | 25 | 101-103 | — | — | 106-123 | — |
| | 25 | 201-203 | — | — | 108-120 | — |

— = not applicable.

TABLE 22

Pharmacokinetic Parameters of Sialic Acid in Beagle Dog Serum Following Oral Administration

| Test Article | Dose Level (mg/kg) | Animal Number | Cmax (μg/mL) | Tmax (h) | AUC(0-t) (μg *h/mL) | MRT(0-t) (h) | T½ (h) | AUC(0-inf) (μg *h/mL) | MRT(0-inf) (h) | Fs (%) |
|---|---|---|---|---|---|---|---|---|---|---|
| TA-1 | 353 | 101 | 15.8 | 2.00 | 54.1 | 2.63 | a | a | a | 3.43 |
|  | 406 | 102 | 26.3 | 2.00 | 68.4 | 2.45 | a | a | a | 3.44 |
|  | 445 | 103 | 40.8 | 0.50 | 128 | 2.07 | 1.41 | 137 | 2.45 | 6.76 |
| TA-1 | 508 | 201 | 20.5 | 2.00 | 66.7 | 2.51 | 1.49 | 68.6 | 2.72 | 2.73 |
|  | 346 | 202 | 14.2 | 2.00 | 51.9 | 2.39 | a | a | a | 3.20 |
|  | 357 | 203 | 12.6 | 2.00 | 43.5 | 3.00 | 1.39 | 45.4 | 3.29 | 2.81 |
| TA-2 | 361 | 101 | 7.98 | 4.00 | 26.5 | 3.51 | a | a | a | 1.64 |
|  | 392 | 102 | 13.7 | 4.00 | 62.4 | 3.76 | a | a | a | 3.25 |
|  | 451 | 103 | 11.9 | 2.00 | 50.0 | 3.19 | 1.28 | 52.3 | 3.48 | 2.60 |
| TA-3 | 353 | 101 | 6.52 | 4.00 | 23.1 | 3.65 | a | a | a | 1.46 |
|  | 382 | 102 | 17.0 | 4.00 | 77.6 | 3.80 | a | a | a | 4.14 |
|  | 439 | 103 | 11.9 | 2.00 | 30.6 | 1.84 | a | a | a | 1.64 |
| TA-4 | 746 | 201 | 15.7 | 4.00 | 74.4 | 4.41 | a | a | a | 2.07 |
|  | 538 | 202 | 9.69 | 2.00 | 52.6 | 3.91 | b | b | b | 2.09 |
|  | 562 | 203 | 8.97 | 2.00 | 38.3 | 3.37 | a | a | a | 1.57 |
| TA-5 | 781 | 201 | 15.3 | 6.00 | 73.6 | 4.59 | a | a | a | 1.96 |
|  | 543 | 202 | 8.20 | 6.00 | 46.4 | 4.70 | a | a | a | 1.83 |
|  | 562 | 203 | 7.79 | 4.00 | 35.7 | 4.58 | a | a | a | 1.47 | a: parameter was not reportable due to the measurable data were not enough to identify the termination elimination phase.
b: parameter was not reportable due to the extrapolation of the AUC to infinity represented more than 20% of the total area.

TABLE 23

Pharmacokinetic parameters of sialic acid in beagle dog serum following IV administration

| Test Article | Dose Level (mg/kg) | Animal Number | AUC(0-t) (μg *h/mL) | MRT(0-t) (h) | T½ (h) | AUC(0-inf) (μg *h/mL) | MRT(0-inf) (h) | CL (mL/min/kg) | Vd (L/kg) |
|---|---|---|---|---|---|---|---|---|---|
| TA-6 | 25 | 101 | 112 | 0.82 | 0.56 | 113 | 0.84 | 3.70 | 0.18 |
|  | 25 | 102 | 123 | 1.06 | 1.40 | 139 | 1.65 | 3.00 | 0.36 |
|  | 25 | 103 | 106 | 0.79 | 0.66 | 108 | 0.84 | 3.87 | 0.22 |
| TA-6 | 25 | 201 | 120 | 1.08 | 0.86 | 121 | 1.13 | 3.44 | 0.26 |
|  | 25 | 202 | 117 | 1.27 | 0.99 | 119 | 1.35 | 3.51 | 0.30 |
|  | 25 | 203 | 108 | 1.18 | 0.58 | 113 | 1.43 | 3.67 | 0.18 |

All the predose urine samples had a measureable concentration of sialic acid and this was used to correct the total increase in urinary excretion of sialic acid at 12 hours postdose. In contrast to serum, most of the concentrations detected in urine samples exceeded the limit of quantitation. The urinary excretion of sialic acid, as a percent of dose administered was estimated for each dosing occasion. Based on the assumption that the amount of drug excreted in urine after oral administration was a reflection of the dose absorbed, the bioavailability of sialic acid was determined based on the percent excretion value following IV and oral administration. The urinary excretion parameters estimated for sialic acid are presented in Table 24 to Table 26.

TABLE 24

Urinary excretion parameters estimated for sialic acid

| | | | Range | |
| Test Article | Dose Level (mg/kg) | Animal Number | Percent Excretion (0-12 hr) (%) | Fu (%) |
|---|---|---|---|---|
| TA-1 | 353-445 | 101-103 | 0.43-3.56 | 2.47-39.1 |
|  | 346-508 | 201-203 | 0.93-2.57 | 1.29-2.17 |

TABLE 24-continued

Urinary excretion parameters estimated for sialic acid

| | | | Range | |
| Test Article | Dose Level (mg/kg) | Animal Number | Percent Excretion (0-12 hr) (%) | Fu (%) |
|---|---|---|---|---|
| TA-2 | 361-451 | 101-103 | 1.08-3.20 | 2.53-97.4 |
| TA-3 | 353-439 | 101-103 | 0.94-2.99 | 1.51-85.0 |
| TA-4 | 538-746 | 201-203 | 0.54-1.93 | 1.42-2.55 |
| TA-5 | 543-781 | 201-203 | 0.02-1.70 | 0.52-2.24 |
| TA-6 | 25 | 101-103 | 1.11-87.7 | — |
|  | 25 | 201-203 | 0-75.7 | — |

— = not applicable.

TABLE 25

Urinary excretion of sialic acid in beagle dog following oral administration

| Test Article | Dose (mg/animal) | Dose Level (mg/kg) | Animal Number | Mass Excreted (µg) Predose | 0-4 hr | 4-8 hr | 8-12 hr | Mass Excreted (0-12 hr) (µg) | Corrected | Percent Excretion (0-12 hr) (%) | Fu (%) |
|---|---|---|---|---|---|---|---|---|---|---|---|
| TA-1 | 3250 | 353 | 101 | 4652.55 | 149.630 | 13342.9 | 4314.71 | 17807.2 | 14085.2 | 0.43 | 39.1 |
|  |  | 406 | 102 | 2448.73 | 549.029 | 65305.8 | 4816.71 | 70671.5 | 68712.5 | 2.11 | 2.47 |
|  |  | 445 | 103 | 4206.50 | 313.356 | 101372 | 17403.2 | 119089 | 115724 | 3.56 | 4.06 |
| TA-1 | 3250 | 508 | 201 | 2372.90 | 0 | 85288.8 | 0 | 85288.8 | 83390.5 | 2.57 | n/a |
|  |  | 346 | 202 | 1177.24 | 21908.6 | 319.025 | 8998.13 | 31225.8 | 30284.0 | 0.93 | 1.29 |
|  |  | 357 | 203 | 1966.81 | 17.3023 | 53674.5 | 1286.44 | 54978.2 | 53404.8 | 1.64 | 2.17 |
| TA-2 | 3250 | 361 | 101 | 4083.30 | 139.071 | 37257.4 | 942.062 | 38338.5 | 35071.9 | 1.08 | 97.4 |
|  |  | 392 | 102 | 4244.85 | 14977.6 | 76498.4 | 15826.0 | 107302 | 103906 | 3.20 | 3.73 |
|  |  | 451 | 103 | 4006.52 | 1003.46 | 73487.3 | 848.833 | 75339.6 | 72134.4 | 2.22 | 2.53 |
| TA-3 | 3250 | 353 | 101 | 5310.07 | 6980.87 | 482.029 | 27399.5 | 34862.4 | 30614.3 | 0.94 | 85.0 |
|  |  | 382 | 102 | 4269.49 | 33345.4 | 64010.5 | 3337.18 | 100693 | 97277.5 | 2.99 | 3.49 |
|  |  | 439 | 103 | 2936.63 | 1901.40 | 42627.6 | 788.657 | 45317.7 | 42968.3 | 1.32 | 1.51 |
| TA-4 | 5000 | 746 | 201 | 2767.70 | 526.991 | 368.095 | 28316.5 | 29211.6 | 26997.4 | 0.54 | n/a |
|  |  | 538 | 202 | 5621.96 | 29695.1 | 709.442 | 25589.5 | 55994.0 | 51496.5 | 1.03 | 1.42 |
|  |  | 562 | 203 | 4074.90 | 385.991 | 73.4542 | 99426.6 | 99886.0 | 96626.1 | 1.93 | 2.55 |
| TA-5 | 5000 | 781 | 201 | 1178.21 | 1269.32 | 372.873 | 63.4198 | 1705.61 | 763.046 | 0.02 | n/a |
|  |  | 543 | 202 | 966.212 | 303.204 | 19168.7 | 281.709 | 19753.6 | 18980.7 | 0.38 | 0.52 |
|  |  | 562 | 203 | 2479.44 | 443.881 | 63164.8 | 23357.0 | 86965.7 | 84982.2 | 1.70 | 2.24 | n/a = not applicable

TABLE 26

Urinary excretion of sialic acid in beagle dog following IV administration

| Test Article | Dose (mg/animal) | Dose Level (mg/kg) | Animal Number | Mass Excreted (µg) Predose | 0-4 hr | 4-8 hr | 8-12 hr | Mass Excreted (0-12 hr) (µg) | Corrected | Percent Excretion (0-12 hr) (%) |
|---|---|---|---|---|---|---|---|---|---|---|
| TA-6 | 227.5 | 25 | 101 | 256.405 | 1941.56 | 509.021 | 274.902 | 2725.48 | 2520.36 | 1.11 |
|  | 202.5 | 25 | 102 | 3508.71 | 161656 | 10622.6 | 4086.45 | 176365 | 173558 | 85.7 |
|  | 182.5 | 25 | 103 | 6124.14 | 105.980 | 158924 | 5859.68 | 164890 | 159990 | 87.7 |
| TA-6 | 162.5 | 25 | 201 | 3085.53 | 267.937 | 0 | 0 | 267.937 | 0 | 0 |
|  | 237.5 | 25 | 202 | 1977.36 | 165111 | 400.537 | 8095.96 | 173607 | 172026 | 72.4 |
|  | 227.5 | 25 | 203 | 1487.66 | 119734 | 50377.7 | 3394.26 | 173506 | 172316 | 75.7 |

In conclusion, the pharmacokinetics of sialic acid in different formulations following a single oral or intravenous dose in the beagle dog were estimated, based on the serum and urine concentration data in this study.

Example 6

Canine Pharmacokinetics Study Regarding Sialic Acid Extended-Release (SA-ER)

Overview: canine pharmacokinetics (PK) were obtained to assess the absorption and pharmacokinetics of SA-ER tablets at three different single doses in a crossover study design in normal canines. The cumulative dose effect of SA-ER was assessed when given in three times per day dosing for seven days.

Test articles:
325 mg SA-ER tablets (as exemplified in the Examples described above)
Gavage: Sialic Acid Powder dissolved in saline at 325 mg/mL (API)
Design:
Four consecutive one dose studies were performed with 1 week washout in N=5 dogs; 5 tabs, 10 tabs and then 15 tabs
One separate repeat-dose study was performed: 1625 mg/dose (=5 tablets) TID every 8 hrs for 7 days (4875 mg/dog/day)
Food fasted prior to dosing, fed ~4 hrs post dose
Bodyweights (BWs) weekly
PK sampling on dosing days and urine collected (0-24 hr pooled/dog)

TABLE 27

Study design: single dose x 3 levels - crossover followed by 7 day dosing

| Phase | Week | Animals | Treatment | Dose (per animal, PO) | Dosing Regimen | Blood for Serum (store at −80° C.) | Urine (store at −80° C.) |
|---|---|---|---|---|---|---|---|
| I | 1 | 5 males or | SA-ER | 1625 mg (5 × 325-mg tablets) | Single dose, one day (respective Day 0) | Pre-study Pre each treatment 1, 2, 4, 8, 12, & 24 hr post-dose | 2, 6, 10 and 24 hr (±2 hr) post-dose |
|  | 2 | females | SA-ER | 3250 mg (10 × 325-mg tablets) |  |  |  |

TABLE 27-continued

Study design: single dose x 3 levels - crossover followed by 7 day dosing

| Phase | Week | Animals | Treatment | Dose (per animal, PO) | Dosing Regimen | Blood for Serum (store at −80° C.) | Urine (store at −80° C.) |
|---|---|---|---|---|---|---|---|
| | 3 | | SA-ER | 4875 mg (15 × 325-mg tablets) | | | |
| | 4 | | SA | 3250 mg SA Solution/suspension | | | |
| II | 5 | 5 males or females | SA-ER | 1625 mg (5 × 325-mg tablets), TID | TID (0, 8, & 16 hr) on Days 0-6 | Days 0 and 6: Pre-dose, 2, and 4 hr for each (nine samples/day) | 24 hr post-Day-6 dose |

Results:

FIGS. 9-12 show graphical data of the results

SA-ER attained reasonable steady state blood levels in canines

Serum levels showed a dose-dependent difference though not proportional to the dose level Repeat dosing demonstrated some accumulation maintaining a significant trough SA level but no high peak API gavage was better absorbed with a higher $C_{max}$ than SA-ER possibly due to early stomach based absorption Goal was for broad, flat absorption curve, without a peak Total sialic acid in the urine suggested a flattening of absorption at the top two dose levels Overall, the canine PK data showed that on repeat dosing 3× per day, a trough SA level was maintained despite fast clearance at about 10× the background level of free sialic acid Example 7

Evaluation of the Pharmacokinetics of Single and Repeat Doses of Sialic Acid Extended-Release (SA-ER) Tablets in Patients with Hereditary Inclusion Body Myopathy (HIBM)

This study was performed to determine the pharmacokinetics of Sialic Acid Extended-Release (SA-ER) after single and repeated dosing. More particularly, the following study evaluated the pharmacokinetic (PK) parameters of an SA-ER with single doses at four (4) dose levels in both a fasted and fed state, followed by 7-day repeat doses at three (3) dose levels in patients with hereditary inclusion body myopathy (HIBM).

Overall Design and Control Methods

This was an open-label, single-dose (in-patient) and repeat-dose (in-patient and outpatient) study of SA-ER in patients with HIBM. Orally administered extended-release tablets (as exemplifed in the Examples described above), each containing 325 mg of sialic acid, were studied. Repeat doses were administered on a three times a day (TID) schedule.

Each patient entered the study unit after all screening procedures were completed (Study Days −28 to −3) and study eligibility was confirmed for a 3-day single-dose (fasted) period (Study Days 0-3), followed by a 2-day outpatient wash-out period (Study Days 4-5), readmission for 2 days for a single-dose (fed) period (Study Days 6-8), a 5-day outpatient repeat-dose treatment period (Study Days 9-12), readmission for the final 2 days of repeat dosing (Study Days 13-14), and discharge from the study unit the following day (Study Day 15). Each patient received a follow-up telephone call approximately 1 week following final discharge. Study days may or may not have been on consecutive calendar days depending on enrollment and dose level staging.

Enrollment of Study Subjects and Assignment to Treatment Groups

Before undergoing any study-related screening procedures, each potential subject provided informed consent. Informed consent was documented by means of a written, signed, and dated informed consent form. The investigator determined the potential subject's suitability for the study by interviewing the potential subject and by performing per-protocol screening assessments. A sufficient number of potential subjects were screened to enroll approximately 24 study subjects at approximately two (2) study sites. Patients who withdraw or were removed from the study after receiving test drug were replaced on a case-by-case basis.

At check-in on Study Day 0, each patient who qualified for the study was sequentially assigned a unique patient number. This patient number identified the patient's case report form (CRF) data throughout the study.

Duration of the Study

Each patient could participate in the study for approximately 4-8 weeks, including a 14-day treatment phase requiring 7 overnight stays in the hospital unit or Phase 1 unit.

Each patient entered the study unit after all screening procedures were completed (Study Days −28 to −3) and study eligibility was confirmed for a 3-day single-dose (fasted) period (Study Days 0-3), followed by a 2-day outpatient wash-out period (Study Days 4-5), readmission for 2 days for a single-dose (fed) period (Study Days 6-8), a 5-day outpatient repeat-dose treatment period (Study Days 9-12), readmission for the final 2 days of repeat dosing (Study Days 13-14), and discharge from the study unit the following day (Study Day 15). Each patient received a follow-up telephone call approximately 1 week following final discharge. Study days may or may not have been on consecutive calendar days depending on enrollment and dose level staging. The estimated duration for an individual patient in this study was approximately 4 to 8 weeks.

Patient Selection and Restrictions

Inclusion Criteria

Individuals eligible to participate in this study must have met all of the following criteria.

1. Must be 18 years to 70 years of age.

2. Willing and able to provide written, signed informed consent after the nature of the study has been explained, and prior to any research-related procedures.

3. Must have a documented diagnosis, confirmed by genetic testing, of hereditary inclusion body myopathy (HIBM), also known as distal myopathy, rimmed vacuoles (DMRV), or Nonaka myopathy due to demonstrated mutations in gene encoding the GNE/MNK enzyme.

4. Willing and able to comply with all study procedures, including multiple overnight stays at a hospital unit or Phase 1 unit.

5. Sexually active subjects must be willing to use an acceptable method of contraception (i.e. double barrier method) while participating in the study and for 30 days after receiving the last dose of SA-ER.

6. Females of childbearing potential must have a negative pregnancy test at screening and be willing to have additional pregnancy tests during the study. Females considered not of childbearing potential include those who have been in menopause at least 2 years, or had bilateral tubal ligation at least 1 year prior to screening, or who have had total hysterectomy.

Exclusion Criteria

Individuals who met any of the following exclusion criteria were not eligible to participate in the study.

1. Pregnant or breastfeeding at screening or planning to become pregnant (self or partner) at any time during the study.

2. Use of any investigational product or investigational medical device within 30 days prior to screening, or requirement for any investigational agent prior to completion of all scheduled study assessments.

3. Ingestion of ManNAc, sialic acid, or related metabolites or sialic acid donors that provide this substrate in either chemical or nutritional supplement form during the 30 days prior to screening. If ManNAc or other substrate was used more than 30 days prior to screening, the time period of use, the compound used, and the dose and dose regimen should be recorded in the patient's history. If a patient has been on substrate replacement therapy in the past, the investigator must consider the potential confounding effects of this therapy before enrolling the patient.

4. Presence of a condition the severity and acuity of which, in the opinion of the investigator, warrant immediate surgical intervention or other treatment.

5. Presence or history of any hypersensitivity to SA or its excipients that, in the judgment of the investigator, places the subject at increased risk for adverse effects.

6. Presence of a concurrent disease or condition that would interfere with study participation or affect safety such as swallowing difficulties.

7. Presence or history of any condition that, in the view of the investigator, places the subject at high risk of poor treatment compliance or of not completing the study.

8. Serum transaminase (ALT, AST, GGT) levels >3× upper limit of normal (ULN) or serum creatinine >2.0 mg/dL.

Prohibited Medications

Patients were not enrolled if they used any investigational product or investigational medical device within 30 days prior to screening, or if they required any investigational agent prior to completion of all scheduled study assessments. Ingestion of N-acetyl-D-mannosamine (ManNAc), sialic acid, or related metabolites or sialic acid donors that provide this substrate in either chemical or nutritional supplement form was prohibited during the 30 days prior to screening and throughout the study. If ManNAc or other substrate was used more than 30 days prior to screening, the time period of use, the compound used, and the dose and dose regimen were recorded in the patient's history. If a patient had been on substrate replacement therapy in the past, the investigator considered the potential confounding effects of this therapy before enrolling the patient.

Patients were not permitted to use alcohol, tobacco or any nicotine-containing product, any caffeine-containing food or beverage, or grapefruit or any grapefruit-containing product from 4 days prior to screening to the time of discharge from the study unit on Study Day 15.

Permitted Medications

Other than the medications specifically prohibited, patients could receive concomitant medications as required. If a patient took any medication other than SA-ER, the patient recorded the date and time the medication was taken, the name of the medication, and the reason the medication was taken in the drug administration diary.

Any concomitant medications or other treatments were recorded in the patient's medical record and CRF along with the dosage and duration of treatment.

Clinical Trial Supplies and Administration

Formulation, Packaging, and Labeling

Sialic acid extended-release tablets (SA-ER tablets) used in this study were white, oval, film-coated tablets containing 325 mg of sialic acid active ingredient and weighed approximately 780 mg (43% active) as exemplified in the Examples described above. The tablets were for oral dosing and were developed to have sustained release of the active ingredient, SA, for up to 24 hours. All the excipients (inactive) contained in the tablet formulation met USP or USP NF compendia specifications and were generally regarded as safe (GRAS). No animal-derived products were used in the manufacture of the tablets. The drug product (the tablet form) was manufactured, packaged, and labeled according to Good Manufacturing Practice (GMP) regulations.

SA-ER 325 mg tablets were bottled and labeled. Each bottle was marked with a label that displayed the protocol number, the name and city, state, and zip code of the sponsor, the identity and strength of the contents ("Sialic Acid Extended Release Tablets, 325 mg"), the number of tablets in the bottle, the lot number, the storage conditions, and the statement, "Caution: New Drug—Limited by Federal (US) Law to Investigational Use."

Study Drug Administration

Patients received SA-ER tablets orally at one of four (4) dose levels in the single-dose phase and one of three (3) dose levels in the repeat-dose phase. During repeat dosing, the total daily dose was divided evenly into three doses given in the morning, in the evening, and at bedtime (qHS) (see below). No placebo or active comparator was administered and the study drug was administered on an open-label basis.

Each of the 24 enrolled patients was sequentially assigned to a specific dose level and received two single-dose exposures at that same dose level (fasted and fed). The low-dose cohorts were filled before assigning higher-dose cohorts. The patient was then assigned to receive one repeat-dose regimen. The lower-dose repeat-dose cohorts were filled before proceeding to higher repeat-dose levels. Dose levels were as follows.

Single doses:
650 mg (n=6)
1,950 mg (n=6)
2,925 mg (n=6)
4,875 mg (n=6)
Multiple dosing:
650 mg TID (1,950 mg/day; n=8)
975 mg TID (2,925 mg/day; n=8)
1,625 mg TID (4,875 mg/day; n=8)

Single doses of study drug were administered by site personnel while patients were confined to the hospital or Phase 1 units. For the repeat-dosing regimens, each patient was dispensed a 7-day supply of study drug at the sequentially assigned dose level along with a drug accountability diary.

Patients were instructed to take SA-ER with water three times a day according to the following schedule: morning (7:00 AM-9:00 AM), evening (5:00 PM-7:00 PM), and at bedtime (qHS; 10:00 PM-12:00 AM). In preparation for the possibility of forgetting a dose, patients were instructed to take a missed dose up to 6 hours after the appointed time but at least 2 hours before taking the subsequent dose. Patients were not to take a double dose. Patients were asked to swallow the administered tablets whole and not to crush or chew them.

As shown in the Study Scheme (FIG. 13), dose levels were studied sequentially, progressing from lower to higher levels of exposure. At each single-dose level, enrollment was staged such that no more than two patients received the currently studied dose level the first week for that dose level, with the remaining four patients for that dose level treated the next week or shortly thereafter, assuming no significant events occurred after the first two patients received the studied dose. Once all six patients had received single doses at a given dose level, then repeat dosing at that daily exposure (divided into TID doses) began.

As shown above, the maximum daily dose of SA-ER in this study was 4,875 mg, administered as 1,625 mg TID. The maximum duration of administration of study drug was a single dose followed by a 2-day washout period and then a second single dose (without subsequent washout, if applicable) followed by a 7-day TID dosing period. Study days may or may not have been consecutive depending on enrollment and dose level staging.

Monitoring Compliance

Patients were confined to the hospital or Phase 1 unit during the single-dose periods, at which times study medication was dispensed and taken under the supervision of site personnel. For the repeat-dosing regimens, each patient was dispensed a 7-day supply of study drug at the sequentially assigned dose level and was asked to maintain a record of self-administration of study drug in a drug accountability diary. This diary was checked when patients returned to the study unit on Study Day 13 and collected by site personnel prior to discharge on Study Day 15. Site personnel maintained a record of all medication dispensed to each patient.

Blinding Procedures

This was an open-label study. Patients were assigned to an open-label SA-ER dose group sequentially as they checked in at the hospital or Phase 1 unit on Study Day 0.

Study Procedures and Assessments

Types and Sequences of Procedures

Figure 13:
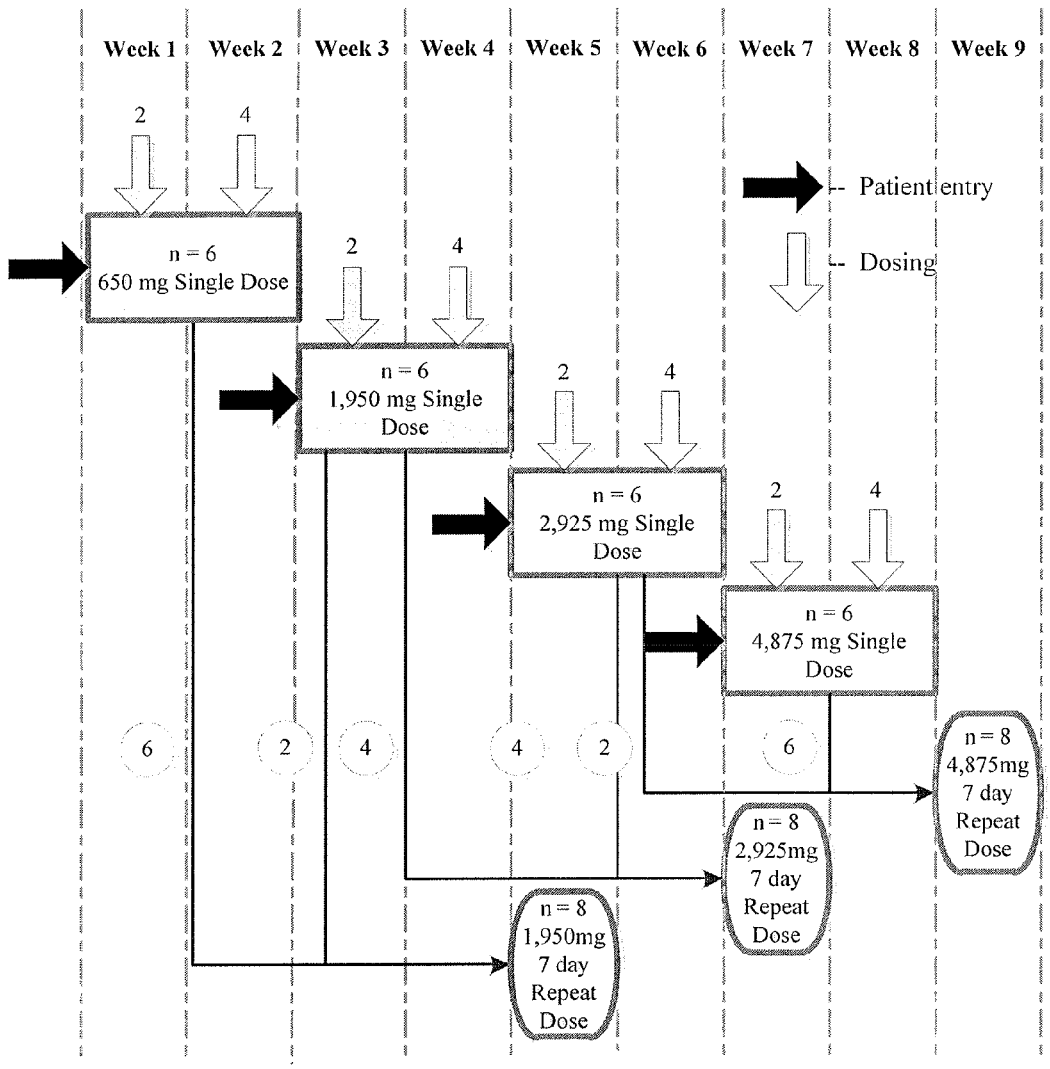
FIG. 13 shows the Study Scheme associated with the ER-SA human clinical trial of Example 7.
Figure 14:
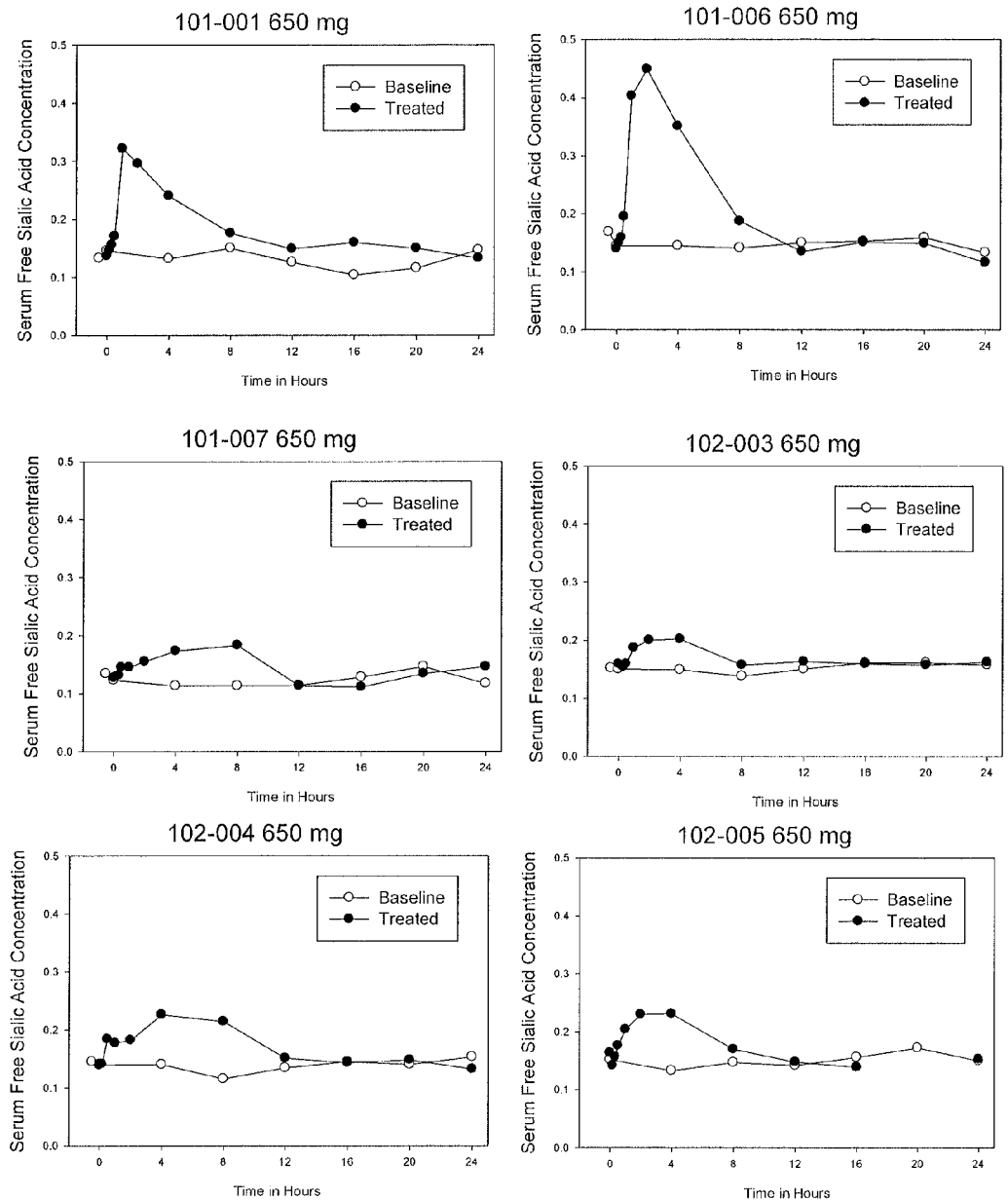
FIG. 14 shows pharmacokinetic data obtained for single dose ER-SA administration (650 mg) for six different human patients. Open circles represent the first day in which baseline monitoring was conducted; closed circles represent the next day when the fasted single dose was administered. Free sialic acid concentration is in µg/mL serum.
Figure 15:
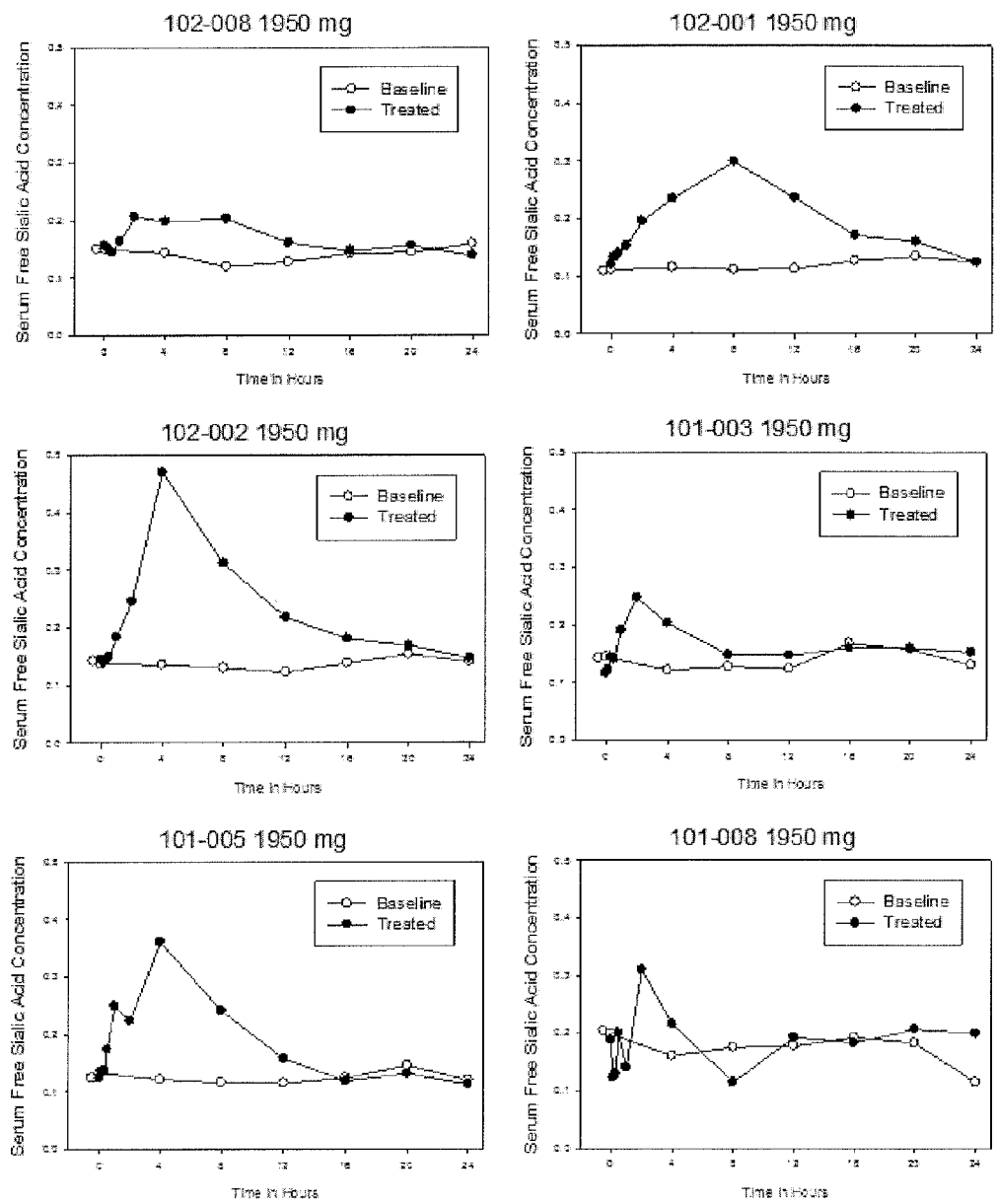
FIG. 15 shows pharmacokinetic data obtained for single dose ER-SA administration (1,950 mg) for six different human patients. Open circles represent the first day in which baseline monitoring was conducted; closed circles represent the next day when the fasted single dose was administered. Free sialic acid concentration is in µg/mL serum.
Figure 16:
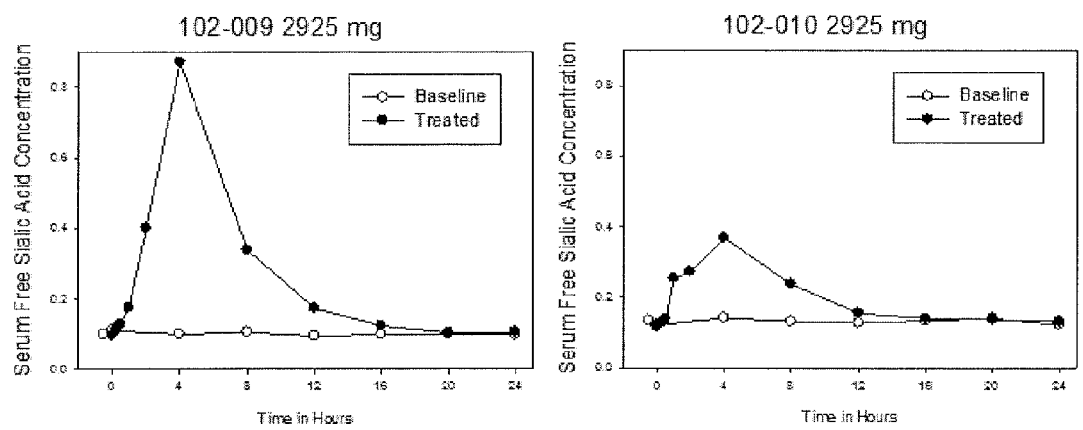
FIG. 16 shows pharmacokinetic data obtained for single dose ER-SA administration (2,925 mg) for two different human patients. Open circles represent the first day in which baseline monitoring was conducted; closed circles represent the next day when the fasted single dose was administered. Free sialic acid concentration is in µg/mL serum.

The overall flow of the study is illustrated in FIG. 13.

Screening Assessments

Potential study participants were screened approximately 3 to 5 days (up to 28 days permitted) prior to admission to the study unit on Study Day 0. Screening procedures included obtaining a medical history, performing a physical and neurological examination, obtaining samples for clinical laboratory tests (blood chemistry, hematology, urinalysis, tests for communicable viral diseases [hepatitis A, B, and C and human immunodeficiency virus], and urine pregnancy test [women only]), and recording vital signs (after 5 minutes sitting, including heart rate, blood pressure, respiratory rate, and temperature), height and weight, and prior medications.

Following evaluation of the results of the screening assessments, patients who met the inclusion and exclusion criteria and who did not present any other reason for exclusion were considered eligible for enrollment into the study.

Screening Failures

If a potential subject provided signed informed consent but failed to meet an inclusion or exclusion criterion, or for any other reason was considered unsuitable for participation in the trial, he or she was considered a screen failure and was not asked or allowed to participate further in the study. The reason for exclusion of the potential subject and the date and time the decision was made to exclude the subject was recorded in the potential subject's CRF.

Single-Dose Phase (Day 0 to Day 7)

Admission and Administration of First Single Dose (Fasted)

Patients who met the screening criteria were admitted to the hospital unit or Phase 1 unit on the evening of Study Day 0. The medical history was updated and continued compliance with entrance criteria was checked. A physical and neurological examination was performed, including weight, and all screening clinical laboratory tests were repeated. In addition, a blood sample was obtained for total and free sialic acid analysis. Vital signs and concomitant medications were recorded.

Patients were sequentially assigned to a dose group on Study Day 0, starting with the lowest dose and following with sequential step assignments to higher doses. Enrollment was staged such that no more than 2 patients received the currently studied dose level the first week for that dose level, with the remaining 4 patients for that dose level treated the next week or shortly thereafter, assuming no significant events occurred after the first 2 patients received the studied dose.

Adverse effects (AEs) were monitored continuously throughout the study (screening through follow-up) by spontaneous reporting as events occur. Drug accountability was recorded following each dispensation of study drug.

On Study Day 1, blood samples were collected at the nominal timepoints 0, 4, 8, 12, 16, 20, and 24 hours to determine the baseline 24-hour, time-matched serum levels of free SA and to establish the diurnal cycle of SA levels. Actual blood collection times were recorded and were within ±30 minutes of the scheduled collection time, except for the Hour 0 timepoint. Patients received nothing by mouth, except water as desired, from 10:00 PM on Day 1 (the night before dosing) through 10:00 AM on Study Day 2 (day of dosing).

On Study Day 2, the initial single dose of study medication was administered with 240 mL of water at approximately 8:00 AM, and blood samples for PK determinations were collected within 30 minutes before administration and at the following nominal timepoints: 10, 20, and 30 minutes and 1, 2, 4, 8, 12, 16, 20, and 24 hours after dosing. Actual blood collection times were recorded and were within ±5 minutes for the 10, 20, 30 minute, and 1 hour timepoints, ±15 minutes for the 2 hour timepoint, and ±30 minutes for all remaining timepoints. Vital signs (sitting) were recorded within 30 minutes predose and 6, 12, and 24 hours after dosing. AEs and any concomitant medications were recorded.

On Study Day 3, samples were obtained for total and free sialic acid at Hour 0 (the same as Study Day 2 Hour 24). Vital signs, AEs, and any concomitant medications were recorded. Patients were discharged from the hospital unit or Phase 1 unit the morning of Study Day 3 after all Study Day 3 procedures had been performed.

Administration of Second Single Dose (Fed)

Patients returned to the hospital unit or Phase 1 unit the evening of Study Day 6. At that time, they received a physical/neurological examination, including weight, and a urine pregnancy test was performed, as applicable (women only). Vital signs (sitting), concomitant medications, and AEs were recorded.

On Study Day 7, the second single dose of study medication (same dose as Study Day 2) was administered with 240 mL of water at approximately 8:00 AM, within 30 minutes following consumption of a full fatty/protein meal. Blood samples for PK determinations were collected within 30 minutes before administration and at the following nominal timepoints: 10, 20, and 30 minutes and 1, 2, 4, 8, 12, 16, 20, and 24 hours after dosing. Actual blood collection times were recorded and within ±5 minutes for the 10, 20, 30 minute, and 1 hour timepoints, ±15 minutes for the 2 hour timepoint, and ±30 minutes for all remaining timepoints. Vital signs (sitting) were recorded within 30 minutes predose and 6, 12, and 24 hours after dosing. AEs and any concomitant medications were recorded.

Repeat-Dose Phase (Study Day 8 to Study Day 14)

On Study Day 8, samples were obtained for total and free sialic acid at Hour 0 (the same as Study Day 7 Hour 24). Vital signs, AEs, and any concomitant medications were recorded. Patients were sequentially assigned to a repeat-dose regimen, as described previously. Patients were given an adequate supply of study medication for 7 days of TID dosing, with full dosing instructions including a drug administration diary or subjects were scheduled at a later date to return to the hospital or Phase 1 unit for a study medication dispensing visit. Subjects took their initial dose of repeat-dose study medication in the hospital or Phase 1 unit prior to discharge.

Study days were or were not consecutive depending on enrollment and dose level staging. Therefore, most subjects were discharged from the hospital or Phase 1 unit on Study Day 8 without receiving study medication for the 7 day repeat dosing. For these patients an additional study visit was required solely for the purposes of dispensing study medication for the 7 days of TID dosing. This visit was scheduled prior to discharge from the hospital or Phase 1 unit. This visit occurred 1 week up to 4 weeks following discharge from the hospital or Phase 1 unit on Study Day 8. For the purpose of the study this visit was considered resumption of Study Day 8 for these subjects.

During this study medication dispensing visit, AEs and concomitant medications were recorded. Patients were given an adequate supply of study medication for 7 days of TID dosing, with full dosing instructions including a drug administration diary. After taking their initial dose of repeat-dose study medication in the hospital or Phase 1 unit, patients were discharged.

Patients returned to the hospital unit or Phase 1 unit the evening of Study Day 13. At that time, they received a physical/neurological examination, including weight. Vital signs (sitting), concomitant medications, and AEs were recorded. A count of remaining tablets of study drug was made. Patients continued to repeat TID dosing while in the study unit.

On Study Day 14, blood samples for PK determinations were collected within 30 minutes (Hour 0) before the morning dose of study medication (at approximately 8:00 AM) and at the nominal timepoints of 4, 8, 12, 16, 20, and 24 hours thereafter to verify the steady-state levels of free sialic acid. Actual blood collection times were recorded and were within ±30 minutes of the scheduled collection time, except for the Hour 0 timepoint. Vital signs (sitting) were recorded within 30 minutes predose and 6, 12, and 24 hours after the morning dose. AEs and any concomitant medications were recorded.

Discharge from Study (Study Day 15)

On Study Day 15, samples were obtained for total and free sialic acid at Hour 0 (the same as Study Day 14 Hour 24). Vital signs, AEs, and any concomitant medications were recorded. Any remaining study medication was obtained from the patients, and no further dose was taken. Barring any residual safety concerns, patients were then discharged from the hospital unit or Phase 1 unit at the discretion of the investigator after all Study Day 15 procedures have been performed.

Patients were considered to have completed the study after the final; Study Day 15 discharge procedures were completed.

Vital Signs

Vital signs (recorded after 5 minutes sitting, including heart rate, blood pressure, respiratory rate, and temperature) were assessed at screening and daily during the three in-patient study periods (Study Days 0-3, 6-8, and 13-15). On Study Days 2, 7, and 14, vital signs were recorded within 30 minutes before dosing (before inital dose on Study Day 14) and 6, 12, and 24 hours thereafter. Weight was measured at screening and on Study Days 0, 6, and 13.

Concomitant Medication Monitoring

Use of concomitant medications was recorded when they were taken.

Pharmacokinetic Assessment

Evaluation of the pharmacokinetics of SA-ER included steady-state levels of free, soluble sialic acid in serum after repeated dosing.

On Study Day 1, blood samples were collected at the nominal timepoints 0, 4, 8, 12, 16, 20, and 24 hours to determine the baseline 24-hour, time-matched serum levels of free sialic acid (SA) and to establish the diurnal cycle of SA levels. Actual blood collection times were recorded and within +30 minutes of the scheduled collection time, except for the Hour 0 timepoint.

On Study Days 2 and 7, blood was drawn for PK analysis within 30 minutes before study drug administration and at the nominal timepoints 10, 20, and 30 minutes and 1, 2, 4, 8, 12, 16, 20, and 24 hours thereafter. Actual blood collection times were recorded and within ±5 minutes for the 10, 20, and 30 minute and 1 hour timepoints, ±15 minutes for the 2 hour timepoint, and ±30 minutes for all remaining timepoints.

On Day 14, blood samples for PK determinations were collected within 30 minutes (Hour 0) before the morning dose of study medication (at approximately 8:00 AM) and at the nominal timepoints of 4, 8, 12, 16, 20, and 24 hours thereafter to verify the steady-state levels of SA. Actual blood collection times were recorded and within ±30 minutes of the actual collection time, except for the Hour 0 timepoint.

Total Volume of Blood Collected

The total volume of blood collected for all scheduled study assessments was approximately 219 mL.

Statistical Considerations and Planned Analyses

Estimate of Sample Size

The sample size of 6 per group for the single-dose phase and 8 per group for the repeat-dosing phase was expected to provide sufficient information to meet the objectives of the study. The sample size was estimated by evaluating the number of patients required to assess PK parameters. Based on prior historical PK studies in rare diseases, 6 to 8 patients per dose group was determined to be sufficient for PK determinations, particularly with the slow extended-release profile expected. A sample size of 6 to 8 patients per dose group and the total of 24 patients was also believed to be an indication of dose-drug level relationship adequate for planning dose levels for future studies.

Pharmacokinetic Analysis

Free sialic acid and its metabolites were quantified using a specific liquid chromatography-tandem mass spectroscopy (LC-MS/MS) analytical method. Serum concentrations of free sialic acid were measured, and the resulting data was listed and tabulated.

Accountability of Clinical Trial Supplies

Storage and Handling

Clinical trial supplies were stored in a secure location at controlled room temperature, shielded from bright light, and kept off the floor.

At each pharmacokinetic sampling timepoint, 3.5 mL of blood was drawn into serum separator tubes and spun at 2000 RPM (or equivalent conversion) at 4° C. for 20 minutes. Serum was separated and transferred into two equal aliquots and stored upright in a −70° C. freezer prior to analysis.

Results—Pharmacokinetic Data

Figure 17:
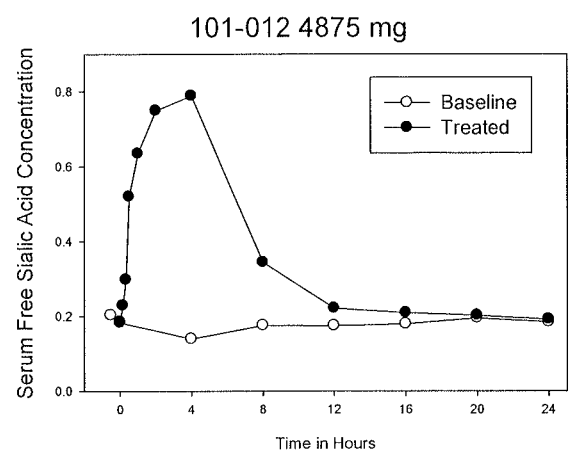
FIG. 17 shows pharmacokinetic data obtained for single dose ER-SA administration (4,825 mg) for one human patient. Open circles represent the first day in which baseline monitoring was conducted; closed circles represent the next day when the fasted single dose was administered. Free sialic acid concentration is in µg/mL serum.
Figure 18:
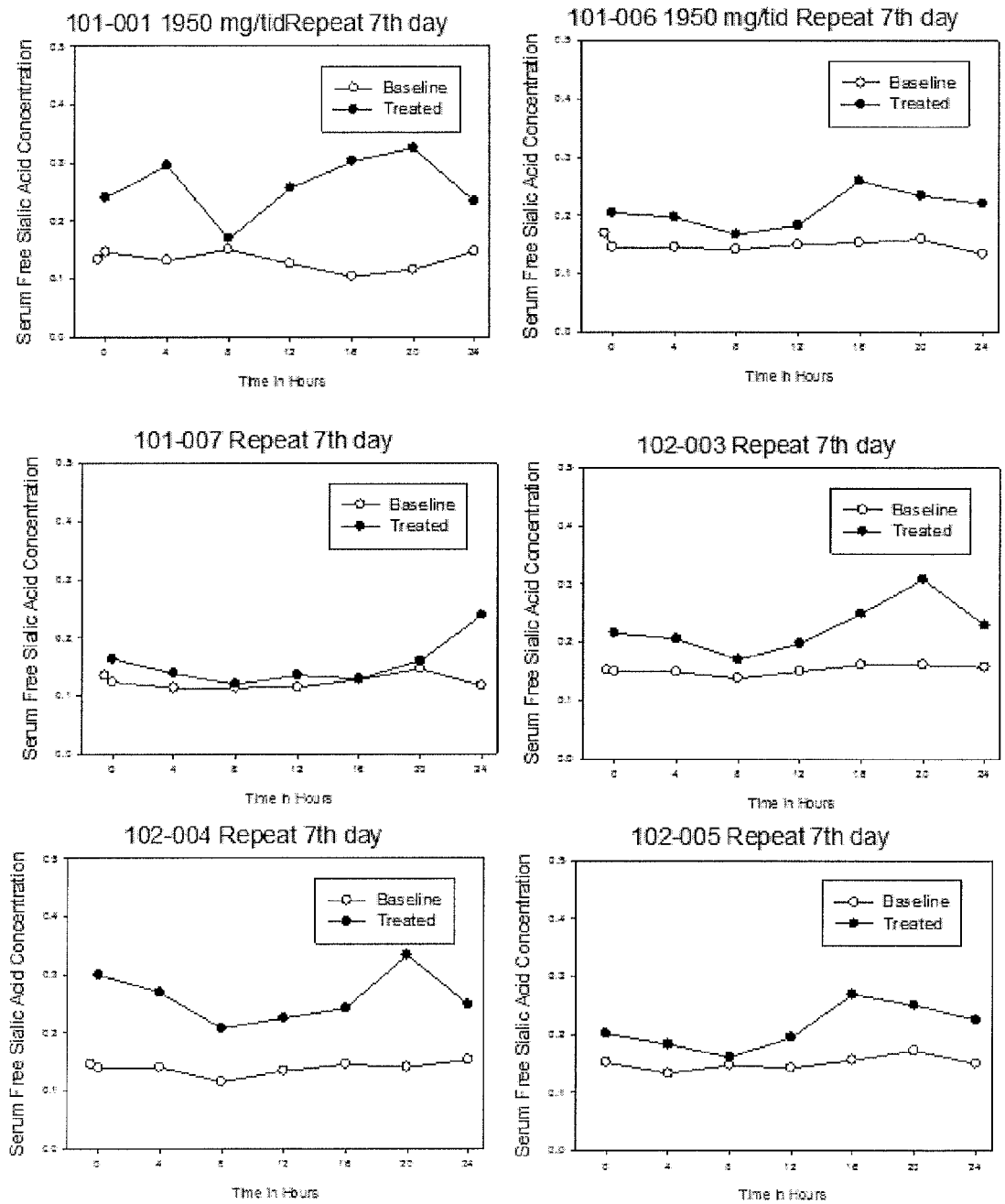
FIG. 18 shows pharmacokinetic data obtained for ER-SA repeated administration (650×3; 1,950 mg) for six different human patients. Open circles represent the first day in which baseline monitoring was conducted; closed circles represent data from the last day of 7 days of three times per day divided dosing. Free sialic acid concentration is in µg/mL serum.
Figure 19:
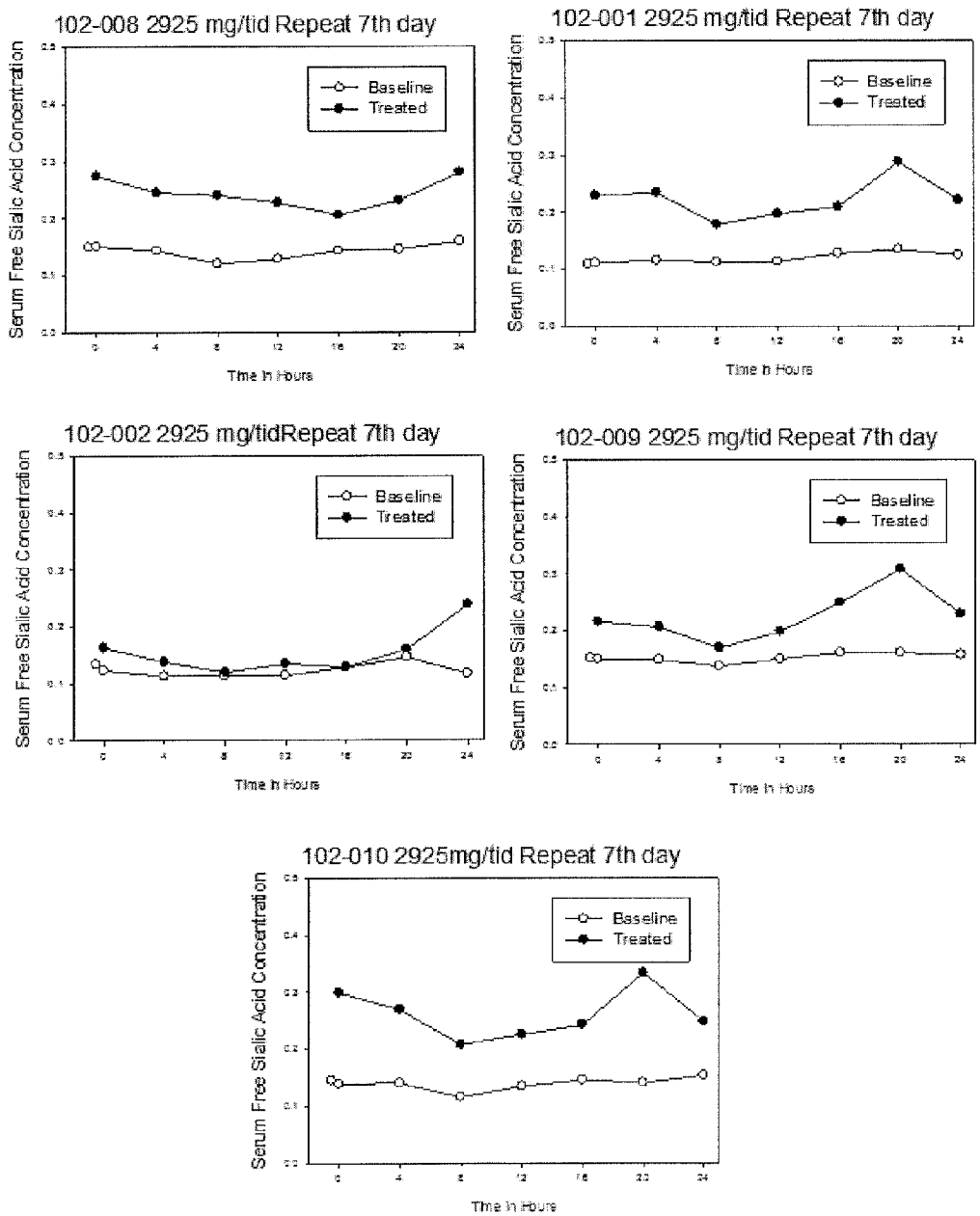
FIG. 19 shows pharmacokinetic data obtained for ER-SA repeated administration (975×3; 2,925 mg) for five different human patients. Open circles represent the first day in which baseline monitoring was conducted; closed circles represent data from the last day of 7 days of three times per day divided dosing. Free sialic acid concentration is in µg/mL serum.

FIGS. 14-17 show PK data obtained for single dose fasted administration for doses of 650 mg (FIG. 13), 1,950 mg (FIG. 14), 2,925 mg (FIG. 15), and 4,825 mg (FIG. 16) for human patients. FIG. 17 shows PK data obtained for repeated dose administration (650 mg×3; 1,950 mg) for human patients. FIG. 18 shows PK data obtained for different repeated dose administration (975×3; 2,925 mg). The levels observed exceed normal patient levels and were close to levels observed in childhood before HIBM disease onset occurs. This suggests that the levels are clinically relevant. Further, the data of FIGS. 18 and 19 demonstrate achievement of excellent steady state control levels without substantial peaks or troughs at which the high enough doses are twice that of normal continuously all day and all night.

Example 8

Phase 1 Clinical ER/SA Study: Interim Safety Study

A Phase 1 study titled "A Phase 1 Study to Evaluate the Safety and Pharmacokinetics of Single and Repeat Doses of Sialic Acid-Extended Release (SA-ER) Tablets in Patients with Hereditary Inclusion Body Myopathy (HIBM)" was conducted. The study evaluated the safety and pharmacokinetics (PK) of single doses and 7 day repeat dosing of SA-ER in HIBM patients. The study was conducted in HIBM patients because the deficiency state of sialic acid in HIBM patients could fundamentally change the metabolism of the active ingredient versus normal healthy volunteers. The original protocol included doses up to 4875 mg/day utilizing a 325 mg tablet size (see Table 8, with Hypromellose), and was subsequently amended to include an additional cohort at 6000 mg/day utilizing a 500 mg tablet size. The 500 mg tablet is the same formulation as the 325 mg tablet and was developed for the convenience of patient administered higher doses of SA-ER.

The specific goals of this study were as follows:

Evaluate the safety of single doses of 650 mg, 1950 mg, 2925 mg, 4875 mg, and 6000 mg/day with and without food.

Evaluate the safety of repeat dosing of SA-ER at doses of 1950 mg/day, 2925 mg/day, 4875 mg/day and 6000 mg/day divided equally and administered three times per day over 7 days.

Determine the PK of SA-ER, including $C_{max}$ and AUC of single doses with and without food, and steady state levels after repeated dosing. The background baseline SA levels in HIBM patients will also be determined.

Establish the best choice for doses to study in Phase 2.

Study Design

A total of 27 HIBM patients were enrolled at two (2) study sites but only 26 received drug. Subjects received SA-ER tablets orally at one of five (5) dose levels in the single-dose phase and one of four (4) dose levels in the repeat-dose phase. Enrolled subjects were sequentially assigned to a specific dose level and received two single-dose exposures at the assigned dose level (Fasted and Fed state). The subjects were then assigned to receive one repeat-dose regimen. During repeat dosing, the total daily dose was divided equally into three doses, and given in the morning, in the evening, and at bedtime (qHS). No placebo or active comparator was administered and the study drug was administered on an open-label basis.

Single doses of study drug were administered by site personnel while subjects were confined to the hospital or Phase 1 unit. Single doses levels were as follows: 650 mg (n=6); 1950 mg (n=6); 2925 mg (n=6); 4875 mg (n=4); and 6000 mg (n=6). For the repeat-dosing regimens, each subject was dispensed a 7-day supply of study drug at the sequentially assigned dose level along with a drug accountability diary. Multiple dose levels were as follows: 650 mg TID (1950 mg/day; n=8); 975 mg TID (2925 mg/day; n=8); 1625 mg TID (4875 mg/day; n=6) and 2000 mg TID (6000 mg/day; n=6).

Figure 20:
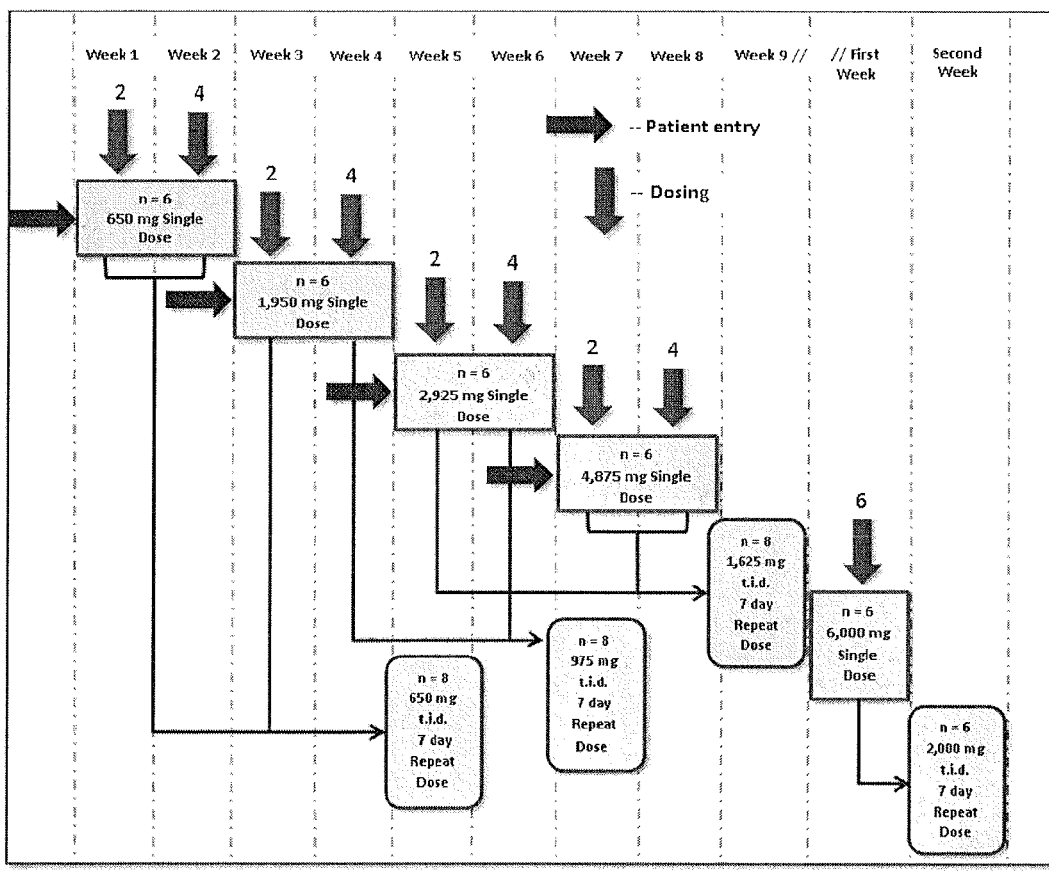
FIG. 20 is a schematic of the Phase I Interim Safety Study dosing schedule.

As shown in FIG. 20, dose levels were sequential, progressing from lower to higher levels of exposure. At the 650 mg, 1950 mg, 2925 mg and 4875 mg single-dose levels, enrollment was staged such that at least two subjects received both single doses (Fasted and Fed state) prior to dosing of the remaining four subjects at the same dose level. Proceeding with the remaining four subjects was contingent on the safety profile observed. Once all 6 subjects received single doses at a given dose level, repeat dosing at that daily exposure (divided into TID doses) began. Subjects in the 6000 mg/day cohort were treated as enrolled and not staged. The lower-dose repeat-dose cohorts were filled before proceeding to higher repeat-dose levels.

Study Results

Preliminary safety and pharmacokinetic results from the study are presented below.

Summary of Preliminary Safety Results

Enrollment

Enrollment status and assignment to treatment groups of subjects are shown in Table 28 and Table 29 below. A total of 37 patients were screened, and 27 were enrolled. Twenty-six (26) individual subjects completed dosing, one subject terminated early (prior to dosing), and eight (8) subjects withdrew consent before being dosed. All subjects dosed with at least one dose, completed all dosing.

In the 650 mg, 1950 mg 2925 mg and the 6000 mg single dose cohorts, 6 patients were dosed per cohort. In the 1950 mg/day and 2925 mg/day multiple dose cohorts, 8 patients were dosed per cohort. The 4875 mg cohort had 4 patients at the single dose stage and 6 patients in the repeat dose stage. There were 6 subjects total in the 6000 mg dose level, both single and repeat stages. Two subjects in the 6000 mg dose cohort had participated earlier in the study in previous dose groups (subjects' 101-010B and 102-004B).

A total of 8 patients withdrew from the study before dosing and these withdrawals were due to the following reasons: 3 withdrew consent (personal reasons), 4 were screen failures (1 elevated GGT levels, 1 not a confirmed diagnosis of HIBM, 2 prohibited concomitant medication). One subject was an early termination (i.e., prior to the initiation of treatment). One subject was eligible and consented but was not dosed because the 6000 mg cohort was full. No subjects withdrew due to adverse events and no subjects withdrew after initiating dosing.

TABLE 28

Patient Enrollment* Status & Dose Assignment

| Subject ID | Status | Dose Assignment | |
|---|---|---|---|
| | | Single | Repeat |
| 101-001 | Enrolled | 650 | 1950 |
| 101-002 | Withdrew consent | | |
| 101-003 | Enrolled | 1950 | 1950 |
| 101-004 | Enrolled | 2925 | 4875 |
| 101-005 | Enrolled | 1950 | 2925 |
| 101-006 | Enrolled | 650 | 1950 |
| 101-007 | Enrolled | 650 | 1950 |
| 101-008 | Enrolled | 1950 | 1950 |
| 101-009 | Withdrew consent | | |
| 101-010 | Enrolled | 2925 | 4875 |
| 101-010B | Enrolled | 6000 | 6000 |
| 101-011 | Enrolled | 2925 | 2925 |
| 101-012 | Enrolled | 4875 | 4875 |
| 101-013 | Enrolled | 2925 | 2925 |
| 101-014 | Withdrew consent | | |
| 101-015 | Enrolled | 4875 | 4875 |
| 101-016 | Enrolled | 4875 | 4875 |
| 101-017 | Enrolled | 4875 | 4875 |
| 101-018 | Enrolled | 6000 | 6000 |
| 101-019 | Screen Failure | | |
| 101-020 | Enrolled | 6000 | 6000 |
| 102-001 | Enrolled | 1950 | 2925 |
| 102-002 | Enrolled | 1950 | 2925 |
| 102-003 | Enrolled | 650 | 1950 |
| 102-003B | Consented/Eligible Not Dosed | | |
| 102-004 | Enrolled | 650 | 1950 |
| 102-004B | Enrolled | 6000 | 6000 |
| 102-005 | Enrolled | 650 | 1950 |
| 102-006 | Screen Failure | | |
| 102-007 | Early Termination | | |
| 102-008 | Enrolled | 1950 | 2925 |
| 102-009 | Enrolled | 2925 | 2925 |
| 102-010 | Enrolled | 2925 | 2925 |
| 102-011 | Screen Failure | | |
| 102-012 | Screen Failure | | |
| 102-013 | Enrolled | 6000 | 6000 |
| 102-014 | Enrolled | 6000 | 6000 |

*Enrolled = includes all patients who took at least one dose of drug.
B = denotes patients that participated twice in study at two different dose assignments.

TABLE 29

Patient Enrollment and Dose Group Assignment as Enrolled

| Subject ID | Status | Dose Assignment | |
|---|---|---|---|
| | | Single | Repeat |
| 101-001 | Enrolled | 650 | 1950 |
| 101-006 | Enrolled | 650 | 1950 |
| 101-007 | Enrolled | 650 | 1950 |
| 102-003 | Enrolled | 650 | 1950 |
| 102-004 | Enrolled | 650 | 1950 |
| 102-005 | Enrolled | 650 | 1950 |
| 101-003 | Enrolled | 1950 | 1950 |
| 101-008 | Enrolled | 1950 | 1950 |
| 101-005 | Enrolled | 1950 | 2925 |
| 102-001 | Enrolled | 1950 | 2925 |
| 102-002 | Enrolled | 1950 | 2925 |
| 102-008 | Enrolled | 1950 | 2925 |
| 101-011 | Enrolled | 2925 | 2925 |
| 101-013 | Enrolled | 2925 | 2925 |
| 102-009 | Enrolled | 2925 | 2925 |
| 102-010 | Enrolled | 2925 | 2925 |
| 101-004 | Enrolled | 2925 | 4875 |
| 101-010 | Enrolled | 2925 | 4875 |
| 101-012 | Enrolled | 4875 | 4875 |
| 101-015 | Enrolled | 4875 | 4875 |
| 101-016 | Enrolled | 4875 | 4875 |
| 101-017 | Enrolled | 4875 | 4875 |
| 101-018 | Enrolled | 6000 | 6000 |
| 102-004B | Enrolled | 6000 | 6000 |
| 102-013 | Enrolled | 6000 | 6000 |
| 102-014 | Enrolled | 6000 | 6000 |
| 101-020 | Enrolled | 6000 | 6000 |
| 101-010B | Enrolled | 6000 | 6000 |

B = denotes patients that participated twice in study at two different dose assignments.

Adverse Events (AEs)

Deaths and Other Significant or Serious Adverse Events (SAEs)

No deaths or significant or serious adverse events (SAEs) have been reported in this study.

Adverse Events (AEs)

The summary of all AEs is shown in Table 30. A total of 31 adverse events were reported from 16 (61.5%) of the 26 subjects dosed. All events were rated as either mild or moderate. Three events were reported with an outcome of unknown: 1) bronchitis that was deemed unrelated to study drug; 2) cough that was also deemed unrelated to study drug (these two events were from the same subject 101-016); and 3) oedema peripheral (finger swelling) which began the day of the first 4875 mg single dose and was deemed possibly related to study drug (subject 101-017).

There were four adverse events rated as moderate: 1) a bruise from a fall (subject 101-001) that was deemed unrelated to study drug; 2) fatigue/tiredness (subject 101-008) which began 3 days after a 1950 mg single dose, resolved within 1 day, and was deemed possibly related to study drug; 3) headache (subject 102-008) which began the day after completing the 2925 mg repeat dose phase (i.e., Study Day 15 following discharge and noted during the follow-up phone call), resolved within 2 days, and was deemed possibly related to study drug; and 4) backache (subject 102-014) which was reported 2 days prior to initiation of study drug, resolved the same day, and was deemed unrelated to study drug.

Of the total 31 adverse events reported to date, 16 were possibly related, two of the 16 events were moderate and resolved (as described previously), and the remaining 14 events were mild with all but one resolved. The one that was not resolved had an outcome of unknown. Of the 14 adverse events rated as mild, there were:

Five events of gastrointestinal (GI) disorders, three of which occurred in one patient (subject 101-003) at the 1950 mg dose and did not appear to be treatment emergent, one event of "heavy in stomach" that was mild and occurred on the first day of the 7 day dosing period for the 1950 mg dose (subject 101-008), and one event of "dry mouth" that occurred during the 7 day treatment period while continuing therapy on 1950 mg (subject 102-005);

One event reported as mild fatigue at the 1950 mg dose that resolved within one day (subject 101-003);

One event of asthenia/all over body weakness that occurred on the first day of the 2925 mg dose, was mild and resolved while continuing on therapy (subject 102-002);

One event each of back pain and leg pain in one subject (subject 101-013) occurring on the same day and starting in the period between the single dose periods and the 1 week treatment period at the 2925 mg dose level;

One event of drowsiness on day 1 of the 7 day dosing period for the 1950 mg dose (subject 102-004);

One event of sore throat on the second day of the 7 day therapy period with the 1950 mg dose level (subject 101-008);

One event of mild headache in each of 2 subjects that resolved within one day and were reported on the first day of the 7 day dosing period at the 4875 mg dose (subject 101-012) and the 6000 mg dose (subject 102-004B);

One event of finger swelling (oedema peripheral) at the 4875 mg single dose level that was mild with an unknown outcome (subject 101-017).

The most common adverse event was GI disorders. Six total GI events were reported by 3 patients, and 4 of the 6 events were from a single patient (subject 101-003) at the 1950 mg dose. Three of those four events in subject 101-003 were deemed possibly related and they occurred at the same time before and at the beginning of the 7 day treatment period. However, the timing did not appear to reflect a treatment emergent event and there were no GI events in the highest 6000 mg dose group. There was no pattern to the gastrointestinal disorders that suggested a treatment or dose related effect. The amount of sialic acid being ingested is well below the amount needed to generate osmotic diarrhea, i.e., loosening of stools was observed in the canine chronic toxicology study at the very highest 2,000 mg/kg dose level, but this effect is not relevant to the clinical study based on these results.

Among the general disorders, fatigue, asthenia or finger swelling occurred in a total of 4 subjects. The events lasted a day or two, and resolved either while continuing in the study or while on therapy (subject 102-002 at the 2925 mg dose). These subjects have substantial muscle weakness and fatigue is a common symptom of HIBM patients. There was no pattern of fatigue observed that would suggest a treatment emergent problem. There were no events of fatigue in the highest dose group 6000 mg.

TABLE 30

Summary of All Adverse Events

| Number of Subjects That Took Drug = 26 | n (% of number of subjects that have taken drug) |
|---|---|
| Subjects that experienced any AE | 16 (61.5) |
| Gastrointestinal disorders | 3 (11.6) |
| Abdominal distension | 1 (3.8) |
| Abdominal pain upper | 1 (3.8) |
| Constipation | 1 (3.8) |
| Diarrhea | 1 (3.8) |
| Dry mouth | 1 (3.8) |
| Flatulence | 1 (3.8) |
| General disorders and administration site conditions | 4 (15.4) |
| Asthenia | 1 (3.8) |
| Fatigue | 2 (7.7) |
| Edema peripheral | 1 (3.8) |

TABLE 30-continued

Summary of All Adverse Events

| Number of Subjects That Took Drug = 26 | n (% of number of subjects that have taken drug) |
|---|---|
| Infections and infestations | 3 (11.5) |
| Bronchitis | 1 (3.8) |
| Nasopharyngitis | 1 (3.8) |
| Upper respiratory tract infection | 1 (3.8) |
| Injury, poisoning and procedural complications | 4 (15.4) |
| Joint injury | 1 (3.8) |
| Laceration | 1 (3.8) |
| Limb injury | 1 (3.8) |
| Procedural site reaction | 1 (3.8) |
| Musculoskeletal and connective tissue disorders | 3 (11.5) |
| Back pain | 3 (11.5) |
| Pain in extremity | 1 (3.8) |
| Nervous system disorders | 3 (11.5) |
| Headache | 3 (11.5) |
| Somnolence | 1 (3.8) |
| Respiratory, thoracic and mediastinal disorders | 3 (11.5) |
| Cough | 2 (7.7) |
| Oropharyngeal pain | 1 (3.8) |
| Respiratory tract congestion | 1 (3.8) |
| Skin and subcutaneous tissue disorders | 1 (3.8) |
| Rash | 1 (3.8) |

In summary, the adverse event profile observed to date has been unremarkable, shows no dose relationship and does not show a pattern of adverse effects that suggest there is any reasonable safety impact at any dose level. The range and type of adverse events observed are common and there was no dose dependent pattern for any drug related or unrelated event that might suggest SA-ER was having any discernible adverse effect in these 26 subjects.

Clinical Assessments

Medical History

A comprehensive medical history was obtained at screening. This history was reviewed in the course of determining each potential subject's eligibility for enrollment.

In general, subjects demonstrated the expected profound muscle atrophy and weakness. A variety of other conditions were observed that are typical for patients in this age group (29 to 61 years).

Physical Examination

Complete physical and neurological examinations were performed at screening and each time the patient checked in to the hospital or Phase 1 unit on Study Days 0, 6, and 13. The neurological examination included assessments of cognition, cranial nerves, motor function, coordination and gait, reflexes, and sensory function.

There were no unexpected findings at baseline. Subjects generally demonstrated moderate to profound weakness in the lower extremities and upper extremities that affected the gait and muscle strength. There was no indication of increasing weakness or loss of muscle strength in this study.

Vital Signs

No significant findings were observed. In general, systolic and diastolic blood pressures were in the low normal range at baseline and during the study. All other vital signs were unremarkable. No significant abnormality was apparent and no changes occurred with treatment.

Clinical Laboratory Assessments

The clinical laboratory evaluations performed in this trial are listed in Table 31.

TABLE 31

List of Clinical Laboratory Tests Performed

Clinical chemistry

Alanine aminotransferase (ALT/SGPT)
Alkaline phosphatase
Amylase
Aspartate aminotransferase (AST/SGOT)
Bilirubin (direct and total)
Blood urea nitrogen (BUN)
Calcium
Chloride
Cholesterol (total)
Creatine kinase (CK)
Creatinine
Gamma-glutamyl transpeptidase (GGT)
Glucose
Lactate dehydrogenase (LDH)
Lipase
Phosphorus
Potassium
Protein (albumin and total)
Sodium
Triglycerides
Uric acid
Communicable viral diseases (screening)

Hepatitis A surface antigen (HAV Ab total)
Hepatitis B surface antigen (HBsAg)
Hepatitis C antibody (HCAb)
Human immunodeficiency virus types 1 and 2 ($HIV_1$ and $HIV_2$)
Hematology Hematocrit
Hemoglobin
MCH concentration (MCHC)
Mean corpuscular hemoglobin (MCH)
Mean corpuscular volume (MCV)
Platelet count
Red blood cell (RBC) count
Reticulocyte count
WBC differential
Neutrophil count (absolute and %)
Lymphocyte count (absolute and %)
Monocyte count (absolute and %)
Eosinophil count (absolute and %)
Basophil count (absolute and %)
White blood cell (WBC) count
Urinalysis (routine)

Blood
Glucose
Ketones
Microscopic examination of the sediment
Bacteria
Casts
Red blood cells
White blood cells
pH
Protein
Specific gravity
Urine pregnancy test (women only)

Abbreviations:
SGOT, serum glutamic-oxaloacetic transaminase;
SGPT, serum glutamic-pyruvic transaminase A number of mild clinical lab abnormalities were observed most often in screening, but there were no abnormalities that were distinctly treatment emergent. The following common abnormalities were observed:

In general, an elevation in creatine kinase was observed which is a known finding in HIBM patients and is expected. These abnormal levels ranged from mildly above the normal range to about 2-3× the normal range and were present at baseline. There was no pattern of change with treatment.

Low creatinine was observed in the majority of patients. Creatinine was usually about ½ the normal level at baseline and did not change with treatment. This finding is mostly likely due to the low muscle mass in HIBM patients which results in a decrease in the total amount of creatinine.

Low urinary uric acid levels were observed in these subjects at screening, and this did not change with treatment. The low urinary uric acid levels may be related to low muscle mass (like creatinine) and a low amount of adenosine-5'-triphosphate (ATP) turnover and purine degradation. The no change with treatment suggests that SA-ER is not inducing an adverse secondary nucleotide metabolic turnover. That is, sialic acid requires addition of cytidine triphosphate (CTP) to become the CMP-sialic acid carrier. If CTP was being excessively consumed, this would lead to the need for increased ATP degradation to balance nucleotide concentrations, and would generate increased uric acid from purine degradation. This degradation pathway is not occurring based on these results.

Alkaline phosphatase was low in many subjects at baseline and this did not change with treatment. This result may reflect a lack of physical activity and less bone turnover in HIBM patients.

Lipase and LDH were marginally elevated in some subjects at baseline. Also noted were marginal low hemoglobins and/or hematocrits, variations in white cell counts, modest or borderline transaminase levels. There was no relationship to treatment observed.

Safety Conclusions

In conclusion, the study drug was well tolerated in this group of HIBM patients based on the AE profile, the absence of SAE's, and the lack of treatment emergent changes in any parameter (AEs, physical examinations, vital signs and clinical laboratory evaluations). The adverse event profile observed to date has been unremarkable, shows no dose relationship and does not show a pattern of adverse effect that suggests there is any significant safety impact. Potential issues (such as diarrhea from the sialic acid load) were not observed and there was no dose dependent relationship for the GI symptoms. Fatigue was observed in 2 patients but resolved. Given the prevalence of fatigue and weakness in this population, the lack of dose dependent changes and resolution on therapy in 1 case, fatigue does not appear to be a treatment emergent phenomenon.

Based on the safety evaluation to date in this Phase 1 study, there are no safety concerns in proceeding to Phase 2.

Summary of Preliminary Pharmacokinetic Results

Enrollment

Data from 26 subjects has been obtained at 5 single dose levels (Fasted and Fed state), and at 4 repeat dose levels for 7 days of dosing divided three times per day (tid). The enrollment of patients in the different cohorts is shown in Table 32.

TABLE 32

Subject Enrollment*, Dose Assignment and PK Data Collection

| Status | All Unique Subjects [a] | Single Dose | | | | | Repeat Dose | | | |
|---|---|---|---|---|---|---|---|---|---|---|
| | | 650 mg | 1950 mg | 2925 mg | 4875 mg | 6000 mg | 1950 mg | 2925 mg | 4875 mg | 6000 mg |
| Enrolled | 27 | | | | | | | | | |
| Have dosing data from: | | | | | | | | | | |
| Any time in the phase | 26 | 6 | 6 | 6 | 4 | 6 | 8 | 8 | 6 | 6 |
| Day 2 | 26 | 6 | 6 | 6 | 4 | 6 | | | | |
| Day 7 | 26 | 6 | 6 | 6 | 4 | 6 | | | | |
| Day 14 | 25 | | | | | | 8 | 8 | 5 | 6 |
| Have Usable PK data from Day: | | | | | | | | | | |
| 1 | 26 | 6 | 6 | 6 | 4 | 6 | 8 | 8 | 6 | 6 |
| 2 | 26 | 6 | 6 | 6 | 4 | 6 | | | | |
| 7 | 25 | 6 | 6 | 5 | 4 | 5 | | | | |
| 14 | 25 | | | | | | 8 | 8 | 4 | 6 |
| Have Date Completed or Discontinued | 27 | 6 | 6 | 6 | 4 | 6 | 8 | 8 | 6 | 6 |

*Enrollment:
27 = number of subjects who enrolled in study including one subject who terminated early prior to dosing.
26 = All subjects who took at least one dose of drug.
25 = number of subjects that have PK data available, sample tubes from one subject were lost and there is a delay in reassaying back-up samples.

PK Data Collection

The protocol put each subject within a cohort through a sequence of free serum sialic acid (SA) assessments at baseline, SA-ER administration, and collection of PK and SA assessments as follows:

Day 1: 24-hour monitoring of SA levels as a baseline to establish the diurnal cycle of free serum sialic acid levels.

Day 2: PK and 24-hour monitoring of SA levels after administration of the fasted dose Day 7: PK and 24-hour monitoring of SA levels after administration of the fed dose Day 14: 24-hour monitoring of SA levels during the 7th day of administration of SA-ER in three times per day divided dosing. During the 7th day, SA-ER was administered during monitoring of the subjects to help establish steady state SA levels on chronic administration.

Analysis of Free SA Levels after Single Doses of SA-ER (Fasted and Fed State)

Free serum sialic acid (SA) levels were determined by a validated assay using a liquid chromatography tandem mass spectrometry (LC/MS/MS) methodology with a Lower Limit of Quantitation (LLOQ) at 0.05 micrograms/ml. The free SA data after a single dose of SA-ER (Fasted and Fed state) and at baseline are summarized for each cohort and are graphically displayed in FIG. 21.

The mean baseline level of SA was 0.143 (SD 0.0094) mcg/ml for all enrolled HIBM-affected subjects, which is significantly lower than the mean SA of 0.203 (SD 0.047) mcg/ml for normal individuals (samples obtained outside this protocol; n=47, age range 18-78 years, and tested using the same validated assay). Baseline SA levels do not reveal any significant diurnal variation in SA levels for any of the subjects individually (not shown) nor as a group with fairly tight standard deviations for the flat baseline curves (FIG. 21).

Figure 21:
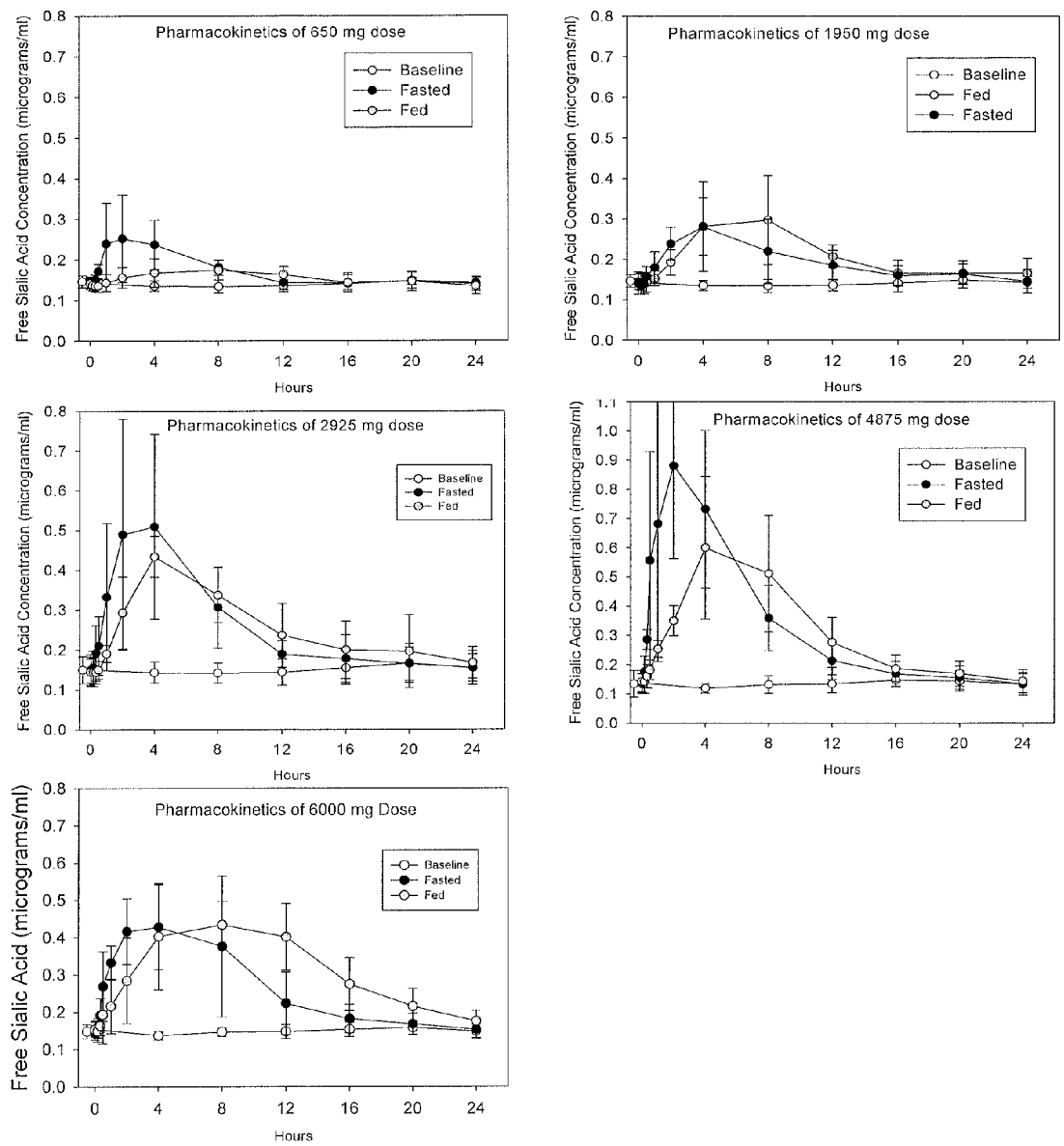
FIG. 21 shows graphs depicting the mean free sialic acid concentrations at single dose levels (fasted and fed states). The individual mean PK curves are shown for the 650 mg, 1950 mg, 2925 mg, 4875 mg and 6000 mg dose levels to compare fasted, fed and baseline SA levels. Panels for 650 mg, 1950 mg, 2925 mg and 6000 mg have the same size y-axis but the 4875 mg panel has a larger y-axis due to the higher levels achieved. Baseline curves for the subjects in each cohort are shown as open circles, fasted levels as black circles and fed curves as grey circles. Baseline sialic acid levels for day 1 for a group of subjects (both Fasted and Fed states) are presented graphically on the same axis so that easy visual comparison can be made of before treatment to after treatment sialic acid levels. The 6000 mg group was administered the 500 mg tablet whereas the rest of the dose groups were administered the 325 mg tablet.

The PK plots in FIG. 21 show that the drug is being absorbed in a generally dose dependent fashion, with increasing doses leading to an increase in the size and shape of the curve, except for the 6000 mg dose (with 500 mg tablet) for which the curve had a lower peak level than the 4875 mg dose level (with 325 mg tablet). The PK curves show increased SA levels for 8-12 hours for most dose levels, with the 6000 mg dose achieving increased levels for 12-16 hours. In general, the onset of absorption was earlier for the fasted treatment relative to fed, and the fed curves extended out longer than the more rapidly declining fasted treatment curves.

The comparisons of the Fed curves (FIG. 21) show that food had variable effects in the different dose groups. The PK curves were lower in the 650 and 4875 mg dose groups with food, similar in the 2925 mg dose group in both fed and fasted state and higher in the 1950 and 6000 mg dose groups with food. In general, the onset of absorption was earlier for the fasted treatment relative to fed, and the fed curves extended out longer than the more rapidly declining fasted treatment curves.

For most dose groups, the fasted curve hit a higher $C_{max}$, but for the 1950 mg and the 6000 mg dose, the apparent $C_{max}$ for fed and fasted is similar. The shift in time and the broadening of the exposure curve is particularly notable for the 6000 mg dose with the 500 mg tablet, which shows a significant increase in blood levels for 16-20 hours.

Figure 22:
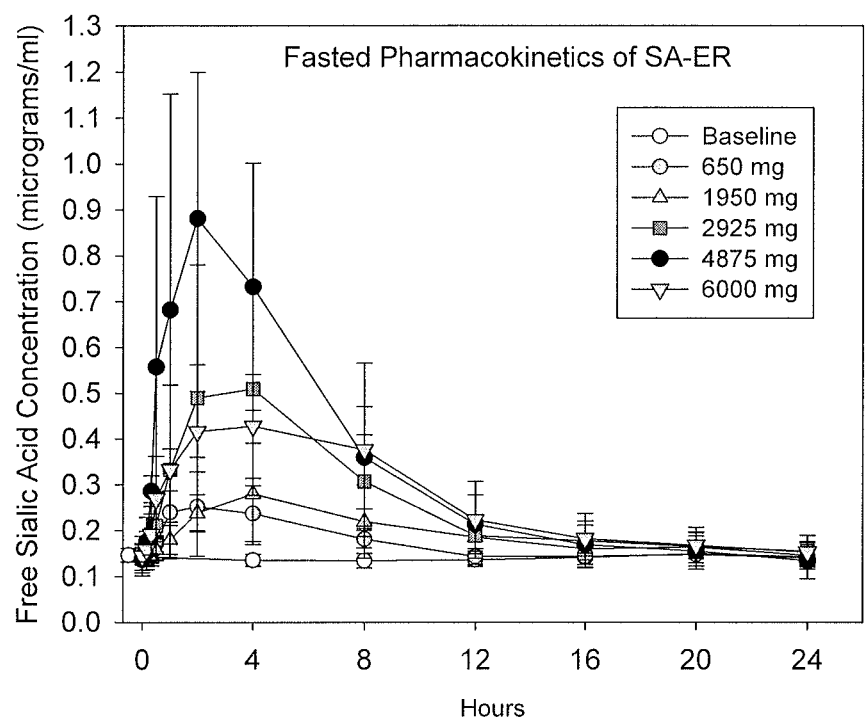
FIG. 22 is a graph depicting mean free sialic acid concentrations at different single dose levels (fasted state). The mean PK curves and standard deviations are shown for the 650 mg, 1950 mg, 2925 mg, 4875 mg and 6000 mg dose levels (Fasted state). The 6000 mg group was administered the 500 mg tablet whereas the rest of the dose groups were administered the 325 mg tablet.

When comparing the Fasted and Fed curves (FIG. 22 and FIG. 23), it is clear that below 4875 mg, there is a dose dependent rise in the SA levels (as expected) and that uptake of SA does not appear to be reaching saturation below 4875 mg/day. At the higher dose levels, there is increasing variability in the peak dose levels which represents very significant inter-subject variability in the absorption pattern for SA. In the 4875 mg single dose level (n=4), two of the 4 subjects had very high levels of free SA (subject 101-016: 1.36 mcg/ml; subject 101-015: 1.18 mcg/ml) as compared to normal (0.203 mcg/mL) and the two other subjects in the same group (subject 101-012: 0.79 mcg/ml; subject 101-017: 0.5 mcg/ml). The 6000 mg dose group would be predicted to have a little higher $C_{max}$ as compared to the 4875 mg dose (given 6000 mg is about 20% more drug), but results were actually lower for the single dose PK. The reason for this is not fully established but may be due to the exceptionally high free SA levels achieved in two out of four total subjects in the 4875 mg single dose group (that may have randomly skewed the data towards a higher mean SA level in this smaller group), or a slower and more prolonged absorption curve for the 500 mg tablet as compared with the 325 mg tablet.

Figure 23:
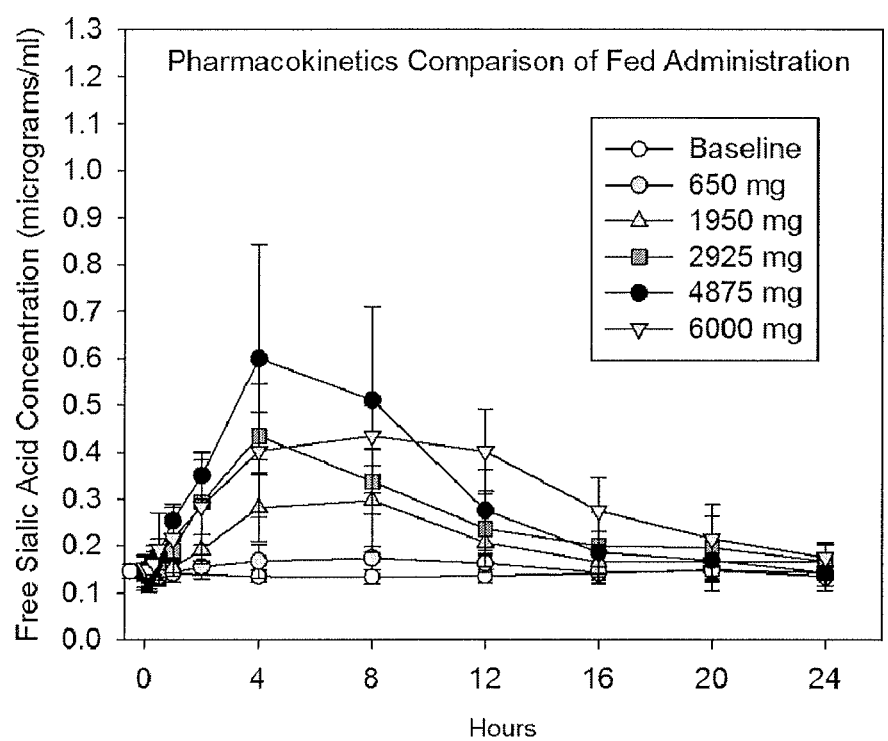
FIG. 23 is a graph depicting mean free sialic acid concentrations at different single dose levels (fed state). The mean PK curves and standard deviations are shown for the 650 mg, 1950 mg, 2925 mg, 4875 mg and 6000 mg dose levels (Fed state). The 6000 mg group was administered the 500 mg tablet whereas the rest of the dose groups were administered the 325 mg tablet.

When comparing the PK plots for the "fed" state in FIG. 23, the difference between the 4875 mg dose and the 6000 mg dose is far less than in the fasted state. In addition, the long period of absorption for the 6000 dose with levels that are almost the same at 4, 8 and 12 hours, suggests a more prolonged absorption curve relative to the other "fed" dose groups. The other dose groups behave similarly with dose dependent absorption and about 12 hours of significant exposure with food.

Analysis of Free SA Levels After 7 Days of Repeat Dosing of SA-ER

Figure 24:
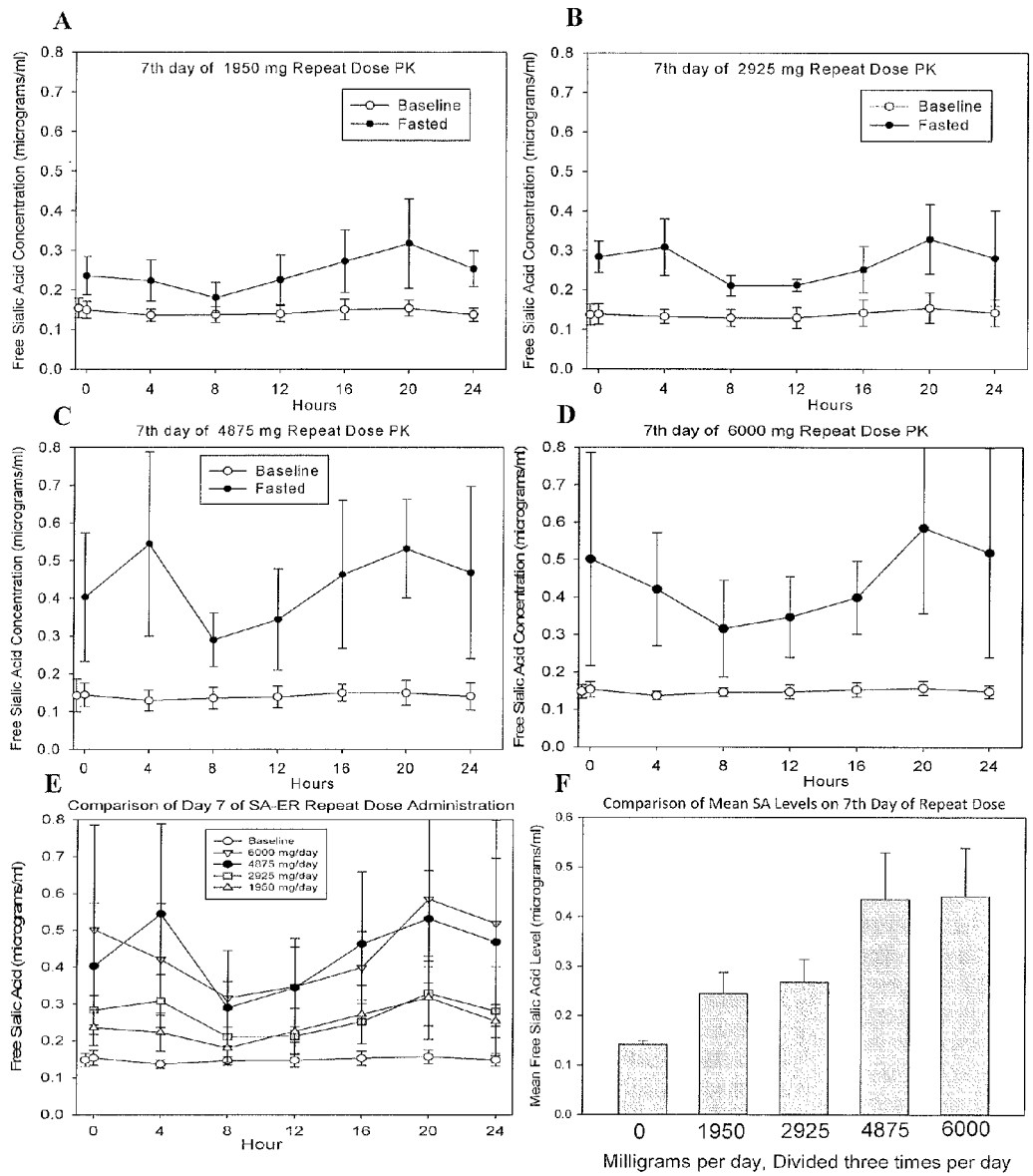
FIGS. 24A-F show graphs depicting free sialic acid concentrations in serum at different repeat dose levels.

Each subject was administered one of four repeat dose levels divided into three times per day dosing over a period of 7 days. On the 7$^{th}$ day of dosing (protocol Day 14), 24-hour monitoring of SA levels was performed to assess whether steady and continuous exposure levels were being achieved. The PK curves over the 24-hour monitoring period are shown in FIG. 24. Individual repeat dose group PK curves are shown (FIGS. 24A-24D), and then all curves are graphed on one panel for comparison (FIG. 24E). The last panel at the bottom right (FIG. 24) shows a comparison of mean SA levels over a 24-hour cycle for each dose group.

The curves (FIGS. 24A-24D) show that steady levels of SA are achieved over the 24-hour cycle with the trough never reaching the baseline mean SA concentration of 0.143 mcg/ml. At the lowest dose of 1950 mg divided three times a day (FIG. 24A) (which is 650 mg three times per day and dosed before morning meal, before evening meal, and at bedtime), the curve reaches the lowest point at 8 hours, but again achieves relatively steady levels over the 24 hour cycle. The peak level is at 20 hours, and likely represents the confluence of the PM dose and the bedtime dose in the subjects. Given the physiology of muscle with nighttime anabolic activity, the SA concentration curve does show adequate coverage of the critical night period.

At the higher dose levels of 4875 mg or 6000 mg divided three times a day, more significant levels are achieved at all time points (FIG. 24C and FIG. 24D). Although the single dose PK levels were very different for the 4875 and 6000 mg doses with different tablet sizes (325 and 500 mg tablets, respectively), the two doses are comparable when given as divided doses over multiple days, and when we compare the 24-hour mean SA levels for 6 subjects in each group (FIG. 24F). The longer PK exposure time of the 500 mg tablet may be providing greater overlap between administrations and thereby resulting in higher cumulative levels at the 6000 mg dose. When compared with untreated HIBM patient baselines, the two lower repeat dose groups have free SA levels about 2× baseline and the two highest dose levels are about 3× the baseline SA level. All doses resulted in free SA levels well above the normal free SA serum levels of 0.203 (SD 0.047) mcg/ml.

Formal Analysis of Pharmacokinetic Parameters

PK analyses were performed using WinNonLin, version 5.3 (PharSight Inc. Mountain View Calif., USA) to assess the standard PK parameters for the single dose data. Given that there is an endogenous level of SA, the proper calculation of PK parameters required the subtraction of the baseline SA levels in order to assess the changing levels for the administered and absorbed SA. Although there was no significant diurnal effect, the baseline SA levels for each subject were subtracted from the corresponding PK level for that time point to create an "adjusted" data point. Therefore, whenever the term "adjusted" is used, it means that the PK parameter was calculated after subtraction of the baseline SA levels. For timepoints in which there is no corresponding baseline level, such as the short 30 min time point from Day 2 PK, a mean baseline level from that subject was subtracted to determine the adjusted net increase in SA level over baseline. These data are shown fully in the PK tables in Table 33A to Table 33D, the key $C_{max}$, AUC, $T_{max}$ and $T_{1/2}$ values are presented below.

TABLE 33A

Listing of PK Serum Parameters for Free Sialic Acid

| Subject ID [a] | Dose Single | Dose Repeat | Phase | Visit | Cmax (mcg/mL) | Tmax (hr) | AUC 0-24 (mcg × hr/mL) | T½ (hr) | R-squared [c] |
|---|---|---|---|---|---|---|---|---|---|
| 101-001 | 650 mg Single Dose SA-ER | 1950 mg Repeat Dose SA-ER | Baseline/No dose | Day 1 | 0.15 | 8.00 | 3.10 | 223.77 | 0.0158 |
| | | | Single/Fasting | Day 2 | 0.32 | 1.00 | 1.25 | 8.20 | 0.5315 |
| | | | Single/Fed | Day 7 | 0.20 | 8.08 | 1.10 | | |
| | | | Repeat | Day 14 | 0.33 | 19.68 | 3.20 | | |
| 101-003 | 1950 mg Single Dose SA-ER | 1950 mg Repeat Dose SA-ER | Baseline/No dose | Day 1 | 0.17 | 16.00 | 3.34 | 21.70 | 0.9321 |
| | | | Single/Fasting | Day 2 | 0.25 | 2.05 | 0.66 | 6.01 | 0.5250 |
| | | | Single/Fed | Day 7 | 0.39 | 4.00 | 1.64 | 6.54 | 0.8002 |
| | | | Repeat | Day 14 | 0.53 | 20.03 | 4.67 | | |
| 101-004 | 2925 mg Single Dose SA-ER | 4875 mg Repeat Dose SA-ER | Baseline/No dose | Day 1 | 0.18 | 24.00 | 3.99 | | |
| | | | Single/Fasting | Day 2 | 0.65 | 1.00 | 3.24 | 3.39 | 0.9224 |
| | | | Single/Fed | Day 7 | 0.49 | 4.03 | 2.69 | 3.73 | 0.9996 |
| | | | Repeat | Day 14 | 0.52 | 12.00 | 5.50 | 7.46 | 0.8579 |
| 101-005 | 1950 mg Single Dose SA-ER | 2925 mg Repeat Dose SA-ER | Baseline/No dose | Day 1 | 0.15 | 19.95 | 2.99 | | |
| | | | Single/Fasting | Day 2 | 0.36 | 4.00 | 1.62 | 3.24 | 0.9800 |
| | | | Single/Fed | Day 7 | 0.49 | 8.02 | 2.55 | 3.43 | 0.7068 |
| | | | Repeat | Day 14 | 0.46 | 4.00 | 3.26 | 3.61 | 0.9949 |
| 101-006 | 650 mg Single Dose SA-ER | 1950 mg Repeat Dose SA-ER | Baseline/No dose | Day 1 | 0.16 | 19.98 | 3.55 | | |
| | | | Single/Fasting | Day 2 | 0.45 | 2.00 | 1.48 | 2.14 | 0.9813 |
| | | | Single/Fed | Day 7 | 0.20 | 2.00 | 0.32 | 18.13 | 0.2814 |
| | | | Repeat | Day 14 | 0.26 | 16.08 | 1.44 | 25.89 | 0.3499 |

TABLE 33A-continued

Listing of PK Serum Parameters for Free Sialic Acid

| Subject ID [a] | Dose Single | Dose Repeat | Phase | Visit | Cmax (mcg/mL) | Tmax (hr) | AUC 0-24 (mcg × hr/mL) | T½ (hr) | R-squared [c] |
|---|---|---|---|---|---|---|---|---|---|
| 101-007 | 650 mg Single Dose SA-ER | 1950 mg Repeat Dose SA-ER | Baseline/No dose | Day 1 | 0.15 | 20.05 | 2.94 | | |
| | | | Single/Fasting | Day 2 | 0.18 | 8.00 | 0.60 | | |
| | | | Single/Fed | Day 7 | 0.14 | 8.00 | 0.20 | | |
| | | | Repeat | Day 14 | 0.24 | 24.00 | 0.59 | | |

Note:
Missing values for Cmax, Tmax and AUC 0-24 for subjects 101-010, 101-016, and 101-020 are due to data inconsistencies. Other missing values for T ½ and R-Squared are due to lack of fit of the regression line, so that T½ could not be calculated.
[a] Some subjects enrolled in the study twice. These subjects are identified with the first enrollment experience listed as a subject number, and the second experience listed with the same subject number and a B.
[b] All parameters at Baseline/No dose are unadjusted (calculated on the concentration value at visit). On all other days, Cmax and Tmax are unadjusted; AUC 0-24, T½ and R-squared are adjusted (calculated on the change from baseline concentration value).
[c] R-squared is an indication of how well the regression line for the terminal portion of the curve fits: the closer to 1.0, the better the fit, while <0.5 is not a good fit. Appropriateness of the estimated values have not yet been evaluated. Regression results are used only in the estimation of half life.
Data as of 12 Mar 2012 21:34

TABLE 33B

Listing of PK Serum Parameters for Free Sialic Acid

| Subject-ID [a] | Dose Single | Dose Repeat | Phase | Visit | Cmax (mcg/mL) | Tmax (hr) | AUC 0-24 (mcg × hr/mL) | T½ (hr) | R-squared [c] |
|---|---|---|---|---|---|---|---|---|---|
| 101-008 | 1950 mg Single Dose SA-ER | 1950 mg Repeat Dose SA-ER | Baseline/No dose | Day 1 | 0.20 | 0.00 | 4.17 | 10.64 | 0.8261 |
| | | | Single/Fasting | Day 2 | 0.31 | 2.03 | 0.67 | 32.12 | 0.0501 |
| | | | Single/Fed | Day 7 | 0.37 | 8.12 | 1.99 | 11.50 | 0.2582 |
| | | | Repeat | Day 14 | 0.40 | 20.03 | 3.16 | | |
| 101-010 | 2925 mg Single Dose SA-ER | 4875 mg Repeat Dose SA-ER | Baseline/No dose | Day 1 | 0.18 | 16.07 | 3.75 | 36.06 | 0.7506 |
| | | | Single/Fasting | Day 2 | 0.42 | 4.17 | 1.97 | 3.55 | 0.9431 |
| | | | Single/Fed | Day 7 | | | | | |
| 101-010B | 6000 mg Single Dose SA-ER | 6000 mg Repeat Dose SA-ER | Baseline/No dose | Day 1 | 0.17 | 12.00 | 3.64 | 40.86 | 0.5900 |
| | | | Single/Fasting | Day 2 | 0.46 | 2.00 | 2.14 | 1.44 | 0.9746 |
| | | | Single/Fed | Day 7 | 0.59 | 4.00 | 4.41 | 3.03 | 0.9995 |
| | | | Repeat | Day 14 | 0.43 | 20.00 | 4.67 | | |
| 101-011 | 2925 mg Single Dose SA-ER | 2925 mg Repeat Dose SA-ER | Baseline/No dose | Day 1 | 0.21 | 16.00 | 4.31 | 34.52 | 0.9959 |
| | | | Single/Fasting | Day 2 | 0.30 | 2.00 | 0.70 | 1.12 | 0.9194 |
| | | | Single/Fed | Day 7 | 0.38 | 4.05 | 1.31 | 1.72 | 0.8900 |
| | | | Repeat | Day 14 | 0.33 | 0.00 | 1.33 | 25.35 | 0.1125 |
| 101-012 | 4875 mg Single Dose SA-ER | 4875 mg Repeat Dose SA-ER | Baseline/No dose | Day 1 | 0.20 | 19.93 | 4.15 | | |
| | | | Single/Fasting | Day 2 | 0.79 | 3.93 | 4.31 | 2.96 | 0.9557 |
| | | | Single/Fed | Day 7 | 0.95 | 3.95 | 5.74 | 3.41 | 0.9372 |
| | | | Repeat | Day 14 | 0.91 | 4.08 | 10.26 | | |
| 101-013 | 2925 mg Single Dose SA-ER | 2925 mg Repeat Dose SA-ER | Baseline/No dose | Day 1 | 0.23 | 20.00 | 4.11 | | |
| | | | Single/Fasting | Day 2 | 0.99 | 2.00 | 4.14 | 4.49 | 0.8343 |
| | | | Single/Fed | Day 7 | 0.41 | 4.02 | 3.84 | 4.97 | 0.8388 |
| | | | Repeat | Day 14 | 0.56 | 24.00 | 4.02 | | |
| 101-015 | 4875 mg Single Dose SA-ER | 4875 mg Repeat Dose SA-ER | Baseline/No dose | Day 1 | 0.12 | 16.00 | 2.63 | 29.62 | 0.9578 |
| | | | Single/Fasting | Day 2 | 1.18 | 2.03 | 3.78 | 2.76 | 0.9296 |
| | | | Single/Fed | Day 7 | 0.42 | 4.07 | 2.25 | 4.05 | 0.7588 |
| | | | Repeat | Day 14 | 0.56 | 20.00 | 4.79 | | |
| 101-016 | 4875 mg Single Dose SA-ER | 4875 mg Repeat Dose SA-ER | Baseline/No dose | Day 1 | 0.15 | 16.08 | 3.07 | 27.76 | 0.9956 |
| | | | Single/Fasting | Day 2 | 1.36 | 1.07 | 7.45 | 1.66 | 0.9094 |
| | | | Single/Fed | Day 7 | 0.67 | 8.00 | 4.94 | 3.61 | 1.0000 |
| | | | Repeat | Day 14 | | | | | |
| 101-017 | 4875 mg Single Dose SA-ER | 4875 mg Repeat Dose SA-ER | Baseline/No dose | Day 1 | 0.14 | 16.00 | 3.08 | 48.83 | 0.9969 |
| | | | Single/Fasting | Day 2 | 0.50 | 4.17 | 4.05 | 3.37 | 0.9180 |
| | | | Single/Fed | Day 7 | 0.47 | 8.00 | 4.05 | 2.84 | 0.9733 |
| | | | Repeat | Day 14 | 0.71 | 16.07 | 9.22 | 10.00 | 0.8269 |
| 101-018 | 6000 mg Single Dose SA-ER | 6000 mg Repeat Dose SA-ER | Baseline/No dose | Day 1 | 0.18 | 0.00 | 3.87 | 53.60 | 0.5930 |
| | | | Single/Fasting | Day 2 | 0.61 | 4.00 | 3.41 | 3.87 | 0.9097 |
| | | | Single/Fed | Day 7 | 0.49 | 8.00 | 4.98 | 3.16 | 0.9953 |
| | | | Repeat | Day 14 | 1.05 | 0.00 | 11.82 | 547.96 | 0.0007 |
| 101-020 | 6000 mg Single Dose SA-ER | 6000 mg Repeat Dose SA-ER | Baseline/No dose | Day 1 | 0.13 | 7.92 | 2.97 | 520.11 | 0.0400 |
| | | | Single/Fasting | Day 2 | 0.56 | 2.00 | 2.27 | 1.87 | 0.9924 |
| | | | Single/Fed | Day 7 | | | | | |
| | | | Repeat | Day 14 | 0.49 | 24.00 | 4.55 | | |

TABLE 33B-continued

Listing of PK Serum Parameters for Free Sialic Acid

| Subject- | Dose | | | | Cmax | Tmax | AUC 0-24 (mcg × | T½ | R-squared |
|---|---|---|---|---|---|---|---|---|---|
| ID [a] | Single | Repeat | Phase | Visit | (mcg/mL) | (hr) | hr/mL) | (hr) | [c] |
| 102-001 | 1950 mg Single Dose SA-ER | 2925 mg Repeat Dose SA-ER | Baseline/No dose | Day 1 | 0.13 | 20.00 | 2.86 | | |
| | | | Single/Fast ing | Day 2 | 0.30 | 8.00 | 2.07 | 4.00 | 0.9775 |
| | | | Single/Fed | Day 7 | 0.21 | 4.03 | 1.26 | 1.64 | 0.9312 |
| | | | Repeat | Day 14 | 0.29 | 20.00 | 2.45 | | |

Note:

Missing values for Cmax, Tmax and AUC 0-24 for subjects 101-010, 101-016, and 101-020 are due to data inconsistencies. Other missing values for T½ and R-Squared are due to lack of fit of the regression line, so that T½ could not be calculated.

[a] Some subjects enrolled in the study twice. These subjects are identified with the first enrollment experience listed as a subject number, and the second experience listed with the same subject number and a B.

[b] All parameters at Baseline/No dose are unadjusted (calculated on the concentration value at visit). On all other days, Cmax and Tmax are unadjusted; AUC 0-24, T½ and R-squared are adjusted (calculated on the change from baseline concentration value).

[c] R-squared is an indication of how well the regression line for the terminal portion of the curve fits: the closer to 1.0, the better the fit, while <0.5 is not a good fit. Appropriateness of the estimated values have not yet been evaluated. Regression results are used only in the estimation of half life.

Data as 12 Mar 2012 Source: Listing1.sas 14 Mar 2012 21:34

TABLE 33C

Listing of PK Serum Parameters for Free Sialic Acid

| Subject | Dose | | | | Cmax | Tmax | AUC 0-24 (mcg × | T½ | R-squared |
|---|---|---|---|---|---|---|---|---|---|
| ID [a] | Single | Repeat | Phase | Visit | (mcg/mL) | (hr) | hr/mL) | (hr) | [c] |
| 102-002 | 1950 mg Single Dose SA-ER | 2925 mg Repeat Dose SA-ER | Baseline/No dose | Day 1 | 0.15 | 20.00 | 3.27 | | |
| | | | Single/Fasting | Day 2 | 0.47 | 4.00 | 2.55 | 2.86 | 0.9990 |
| | | | Single/Fed | Day 7 | 0.29 | 8.00 | 1.83 | 4.63 | 0.7248 |
| | | | Repeat | Day 14 | 0.38 | 20.10 | 3.45 | | |
| 102-003 | 650 mg Single Dose SA-ER | 1950 mg Repeat Dose SA-ER | Baseline/No dose | Day 1 | 0.16 | 16.00 | 3.57 | 211.64 | 0.7160 |
| | | | Single/Fasting | Day 2 | 0.20 | 4.00 | 0.41 | 8.40 | 0.9986 |
| | | | Single/Fed | Day 7 | 0.19 | 8.00 | 0.22 | | |
| | | | Repeat | Day 14 | 0.31 | 20.00 | 1.77 | | |
| 102-004 | 650 mg Single Dose SA-ER | 1950 mg Repeat Dose SA-ER | Baseline/No dose | Day 1 | 0.15 | 23.70 | 3.24 | | |
| | | | Single/Fasting | Day 2 | 0.23 | 4.00 | 0.87 | 3.59 | 0.8356 |
| | | | Single/Fed | Day 7 | 0.19 | 8.00 | 0.60 | 1.91 | 0.8866 |
| | | | Repeat | Day 14 | 0.33 | 20.00 | 2.93 | | |
| 102-004B | 6000 mg Single Dose SA-ER | 6000 mg Repeat Dose SA-ER | Baseline/No dose | Day 1 | 0.16 | 16.32 | 3.39 | 66.84 | 0.8003 |
| | | | Single/Fasting | Day 2 | 0.71 | 8.00 | 5.26 | 2.70 | 0.9937 |
| | | | Single/Fed | Day 7 | 0.52 | 12.00 | 4.66 | 3.93 | 0.9995 |
| | | | Repeat | Day 14 | 0.74 | 20.00 | 7.38 | | |
| 102-005 | 650 mg Single Dose SA-ER | 1950 mg Repeat Dose SA-ER | Baseline/No dose | Day 1 | 0.17 | 20.05 | 3.59 | | |
| | | | Single/Fasting | Day 2 | 0.39 | 20.00 | 1.47 | | |
| | | | Single/Fed | Day 7 | 0.21 | 4.00 | 0.55 | 4.03 | 1.0000 |
| | | | Repeat | Day 14 | 0.27 | 16.00 | 1.49 | 13.53 | 0.8434 |
| 102-008 | 1950 mg Single Dose SA-ER | 2925 mg Repeat Dose SA-ER | Baseline/No dose | Day 1 | 0.16 | 23.92 | 3.32 | | |
| | | | Single/Fasting | Day 2 | 0.21 | 2.00 | 0.78 | 3.39 | 0.6418 |
| | | | Single/Fed | Day 7 | 0.22 | 24.00 | 0.97 | 9.50 | 0.2531 |
| | | | Repeat | Day 14 | 0.28 | 24.00 | 2.37 | 72.21 | 0.1123 |

Note:

Missing values for Cmax, Tmax and AUC 0-24 for subjects 101-010, 101-016, and 101-020 are due to data inconsistencies. Other missing values for T½ and R-Squared are due to lack of fit of the regression line, so that T½ could not be calculated.
[a] Some subjects enrolled in the study twice. These subjects are identified with the first enrollment experience listed as a subject number, and the second experience listed with the same subject number and a B.
[b] All parameters at Baseline/No dose are unadjusted (calculated on the concentration value at visit). On all other days, Cmax and Tmax are unadjusted; AUC 0-24, T½ and R-squared are adjusted (calculated on the change from baseline concentration value).
[c] R-squared is an indication of how well the regression line for the terminal portion of the curve fits: the closer to 1.0, the better the fit, while <0.5 is not a good fit. Appropriateness of the estimated values have not yet been evaluated. Regression results are used only in the estimation of half life.
Data as 12 Mar 2012 Source: Listing1.sas 14 Mar 2012 21:34

TABLE 33D

Listing of PK Serum Parameters for Free Sialic Acid

| Subject ID [a] | Dose Single | Dose Repeat | Phase | Visit | Cmax (mcg/mL) | Tmax (hr) | AUC 0-24 (mcg × hr/mL) | T½ (hr) | R-squared [c] |
|---|---|---|---|---|---|---|---|---|---|
| 102-009 | 2925 mg Single Dose SA-ER | 2925 mg Repeat Dose SA-ER | Baseline/No dose | Day 1 | 0.11 | 0.00 | 2.40 | 184.12 | 0.4227 |
| | | | Single/Fasting | Day 2 | 0.87 | 3.97 | 4.25 | 2.73 | 0.9110 |
| | | | Single/Fed | Day 7 | 0.49 | 4.00 | 2.91 | 4.28 | 0.7607 |
| | | | Repeat | Day 14 | 0.41 | 20.00 | 3.93 | | |
| 102-010 | 2925 mg Single Dose SA-ER | 2925 mg Repeat Dose SA-ER | Baseline/No dose | Day 1 | 0.14 | 4.00 | 3.16 | 196.81 | 0.2298 |
| | | | Single/Fasting | Day 2 | 0.37 | 4.00 | 1.59 | 3.87 | 0.7843 |
| | | | Single/Fed | Day 7 | 0.40 | 4.00 | 2.49 | 4.72 | 0.8815 |
| | | | Repeat | Day 14 | 0.44 | 20.00 | 3.24 | | |
| 102-013 | 6000 mg Single Dose SA-ER | 6000 mg Repeat Dose SA-ER | Baseline/No dose | Day 1 | 0.17 | 0.00 | 3.74 | | |
| | | | Single/Fasting | Day 2 | 0.34 | 2.00 | 1.18 | 4.90 | 0.8967 |
| | | | Single/Fed | Day 7 | 0.36 | 12.00 | 2.94 | 2.34 | 0.9238 |
| | | | Repeat | Day 14 | 0.35 | 20.12 | 2.51 | | |
| 102-014 | 6000 mg Single Dose SA-ER | 6000 mg Repeat Dose SA-ER | Baseline/No dose | Day 1 | 0.17 | 20.00 | 3.72 | | |
| | | | Single/Fasting | Day 2 | 0.45 | 8.00 | 2.88 | 3.53 | 0.9721 |
| | | | Single/Fed | Day 7 | 0.42 | 12.00 | 3.84 | 4.63 | 1.0000 |
| | | | Repeat | Day 14 | 0.90 | 20.00 | 9.51 | | |

Note:
Missing values for Cmax, Tmax and AUC 0-24 for subjects 101-010, 101-016, and 101-020 are due to data inconsistencies. Other missing values for T½ and R-Squared are due to lack of fit of the regression line, so that T½ could not be calculated.
[a] Some subjects enrolled in the study twice. These subjects are identified with the first enrollment experience listed as a subject number, and the second experience listed with the same subject number and a B.
[b] All parameters at Baseline/No dose are unadjusted (calculated on the concentration value at visit). On all other days, Cmax and Tmax are unadjusted; AUC 0-24, T½ and R-squared are adjusted (calculated on the change from baseline concentration value).
[c] R-squared is an indication of how well the regression line for the terminal portion of the curve fits: the closer to 1.0, the better the fit, while <0.5 is not a good fit. Appropriateness of the estimated values have not yet been evaluated. Regression results are used only in the estimation of half life.
Data as 12 Mar 2012 Source: Listing1.sas 14 Mar 2012 21:34

The $C_{max}$ data (Table 34) shows that in general, fasted data (Day 2) showed the highest $C_{max}$, for all dose levels except for the 1950 mg dose level. The highest $C_{max}$ (0.958 mcg/ml) was achieved in the 4875 mg dose group (n=4), using the 325 mg tablets, but the range of values was about 3 fold (i.e., from 0.423 to 1.36 mcg/ml) within this dose group. The $C_{max}$ achieved at the 6000 mg dose level (n=6), using the 500 mg tablet, was lower at 0.520 mcg/ml but with a much tighter standard deviation and range of values from 0.335 to 0.711 mcg/ml. Interestingly, during the repeat dose phase the two top doses of 4875 mg (n=6) and 6000 mg (n=6) had similar $C_{max}$ levels of 0.676 and 0.661, respectively.

TABLE 34

$C_{max}$ (mcg/ml) Values Following Single Dose Administration (Fed and Fasted) and Repeat Doses of SA-ER

| Parameter | Phase | Visit | Statistic | 650 mg | 1950 mg | 2925 mg | 4875 mg | 6000 mg |
|---|---|---|---|---|---|---|---|---|
| Number of Subjects Who Took Drug | Single | | N | 6 | 6 | 6 | 4 | 6 |
| | Repeat | | N | | 8 | 8 | 6 | 6 |
| Cmax (mcg/mL) | Baseline (No Dose) | Day 1 | N | 6 | 6 | 6 | 4 | 6 |
| | | | Mean | 0.157 | 0.160 | 0.174 | 0.151 | 0.162 |
| | | | SD | 0.009 | 0.022 | 0.043 | 0.031 | 0.017 |
| | | | Median | 0.156 | 0.157 | 0.178 | 0.143 | 0.167 |
| | | | Min, Max | 0.146, 0.172 | 0.134, 0.198 | 0.110, 0.226 | 0.122, 0.195 | 0.131, 0.179 |
| | | | CV(%) | 5.919 | 13.755 | 24.783 | 20.776 | 10.225 |
| | Single/Fasting | Day 2 | N | 6 | 6 | 6 | 4 | 6 |
| | | | Mean | 0.296 | 0.315 | 0.600 | 0.958 | 0.520 |
| | | | SD | 0.110 | 0.093 | 0.282 | 0.386 | 0.134 |
| | | | Median | 0.274 | 0.305 | 0.538 | 0.984 | 0.507 |
| | | | Min, Max | 0.183, 0.449 | 0.206, 0.470 | 0.300, 0.985 | 0.503, 1.360 | 0.335, 0.711 |
| | | | CV(%) | 37.068 | 29.353 | 47.107 | 40.295 | 25.676 |
| | Single/Fed | Day 7 | N | 6 | 6 | 5 | 4 | 5 |
| | | | Mean | 0.187 | 0.326 | 0.434 | 0.629 | 0.494 |
| | | | SD | 0.025 | 0.106 | 0.051 | 0.240 | 0.124 |
| | | | Median | 0.192 | 0.326 | 0.413 | 0.571 | 0.489 |
| | | | Min, Max | 0.139, 0.209 | 0.213, 0.485 | 0.379, 0.493 | 0.423, 0.950 | 0.356, 0.685 |
| | | | CV(%) | 13.277 | 32.627 | 11.834 | 38.111 | 25.183 |
| | Baseline (No Dose) | Day 1 | N | | 8 | 8 | 6 | 6 |
| | | | Mean | | 0.163 | 0.160 | 0.160 | 0.162 |
| | | | SD | | 0.017 | 0.039 | 0.028 | 0.017 |
| | | | Median | | 0.160 | 0.150 | 0.161 | 0.167 |
| | | | Min, Max | | 0.146, 0.198 | 0.110, 0.226 | 0.122, 0.195 | 0.131, 0.179 |
| | | | CV(%) | | 10.105 | 24.447 | 17.602 | 10.225 |

TABLE 34-continued $C_{max}$ (mcg/ml) Values Following Single Dose Administration (Fed and Fasted) and Repeat Doses of SA-ER

| Parameter | Phase | Visit | Statistic | 650 mg | 1950 mg | 2925 mg | 4875 mg | 6000 mg |
|---|---|---|---|---|---|---|---|---|
| | Repeat | Day 14 | N | | 8 | 8 | 4 | 6 |
| | | | Mean | | 0.333 | 0.393 | 0.676 | 0.661 |
| | | | SD | | 0.095 | 0.093 | 0.180 | 0.282 |
| | | | Median | | 0.317 | 0.395 | 0.635 | 0.618 |
| | | | Min, Max | | 0.238, 0.531 | 0.280, 0.555 | 0.520, 0.914 | 0.346, 1.050 |
| | | | CV(%) | | 28.495 | 23.806 | 26.575 | 42.624 |

NOTE:
Baseline values for single and repeat dose levels slightly vary because some patients who are included in one dose group for the single dose phase are included in a different dose group for the repeat dose phase. Therefore, the baseline means attempt to reflect the mean of the same patients that are being compared, and the mean changes slightly when you take some patients in or out.

The $AUC_{0-24\ hours}$ data (Table 35) shows adjusted values for day 2, 7 and 14. The baseline PK values (Day 1) are not adjusted and are not relevant given that no drug was given. All curves showed a slower onset of absorption and longer exposure curves with food. Unlike the impact on $C_{max}$, the impact of food on AUC is complex with some dose levels showing higher AUC with fasted conditions (650 mg and 4,875 mg dose), similar AUC under both fasted and fed conditions (2925 mg dose) and higher AUC with food (1950 and 6000 mg dose). The extension of the curves appear to compensate for the effect of a lower $C_{max}$ peak for some dose levels by a wider curve in the 8-16 hour period leading to greater potential overlap between doses. For the 6000 mg dose, the AUC is significantly greater (~+46%) when administered in the fed state at 4.165 mcg-hr/ml compared with 2.856 fasted. Given that the 6000 mg dose was administered using the 500 mg tablet, the differences observed may be due to a subtle effect of the larger tablet size on the absorption curve, even though in vitro dissolution data is comparable for the 325 mg and 500 mg tablets. The larger tablet may have a longer time of release in vivo. This difference coupled with food effect delaying the exit of SA from the stomach may enhance the overall absorption of SA (acidity should improve sialic acid absorption by neutralizing its charge). Therefore all things considered and based on the data, and without being bound by theory, providing the larger tablet with food may provide net better drug absorption. Regardless, from the results it is clear that either with or without food, adequate absorption of the drug is occurring at all dose levels.

In addition, $AUC_{0-24\ hours}$ during Day 14 (or $7^{th}$ day of repeat dosing) shows that overall higher AUC levels can be achieved at steady state when dosing is divided three times per day, which suggests that there is some saturation effect on absorption. For example, at the 6000 mg dose level, the adjusted repeat dose $AUC_{0-24\ hours}$ was 6.740 mcg*hr/ml, as compared with the AUC levels of 2.856 mcg*hr/ml (Fasted state) and 4.165 mcg*hr/ml (Fed state) at single doses of 6000 mg. The 6000 mg dose group's AUC is ~235% and ~160% higher when the dose was given as a divided repeat dose rather than as one single dose. The $AUC_{0-24\ hours}$ for the 4875 mg repeat dose group was 7.442 mcg*hr/ml (Std dev 2.702), which is comparable to that for 6000 mg repeat dose group at 6.740 mcg*hr/ml (Std. dev 3.487). Although the difference in PK for the 4875 mg and 6000 mg following single dose administration appears large, the data look similar following administration of divided doses three times a day, which is more relevant to the clinical setting. Given that absorption of SA may be an active pinocytosis-based process (Oetke C., Hinderlich S., Brossmer R., Reutter W., Pawlita M., and Keppler O T. 2001. Evidence for efficient uptake and incorporation of sialic acid by eukaryotic cells. Eur. J. Biochem. 268(16):4553-4561), saturation and competition for absorption of drug may be occurring simultaneously.

TABLE 35

$AUC_{0-24\ hr}$ (mcg × hr/mL) Values Following Single Dose Administration (Fed and Fasted) and Repeat Doses of SA-ER

| Parameter | Phase | Visit | Statistic | 650 mg | 1950 mg | 2925 mg | 4875 mg | 6000 mg |
|---|---|---|---|---|---|---|---|---|
| AUC(0-24) | Baseline (No Dose) | Day 1 | N | 6 | 6 | 6 | 4 | 6 |
| (mcg × hr/mL) | | | Mean | 3.330 | 3.326 | 3.620 | 3.231 | 3.554 |
| | | | SD | 0.279 | 0.459 | 0.715 | 0.649 | 0.329 |
| | | | Median | 3.394 | 3.297 | 3.868 | 3.073 | 3.683 |
| | | | Min, Max | 2.939, 3.587 | 2.861, 4.173 | 2.404, 4.308 | 2.627, 4.152 | 2.968, 3.865 |
| | | | CV(%) | 8.383 | 13.790 | 19.738 | 20.080 | 9.243 |
| Adjusted AUC(0-24) | Single/Fasting | Day 2 | N | 6 | 6 | 6 | 4 | 6 |
| (mcg × hr/mL) | | | Mean | 1.011 | 1.393 | 2.649 | 4.899 | 2.856 |
| | | | SD | 0.457 | 0.811 | 1.451 | 1.712 | 1.398 |
| | | | Median | 1.058 | 1.204 | 2.601 | 4.185 | 2.574 |
| | | | Min, Max | 0.405, 1.476 | 0.661, 2.555 | 0.703, 4.253 | 3.781, 7.446 | 1.177, 5.263 |
| | | | CV(%) | 45.223 | 58.244 | 54.764 | 34.948 | 48.951 |
| | Single/Fed | Day 7 | N | 6 | 6 | 5 | 4 | 5 |
| | | | Mean | 0.497 | 1.707 | 2.651 | 4.246 | 4.165 |
| | | | SD | 0.339 | 0.558 | 0.909 | 1.501 | 0.803 |
| | | | Median | 0.436 | 1.733 | 2.693 | 4.495 | 4.406 |
| | | | Min, Max | 0.195, 1.099 | 0.971, 2.551 | 1.314, 3.845 | 2.249, 5.745 | 2.940, 4.981 |
| | | | CV(%) | 68.322 | 32.693 | 34.303 | 35.339 | 19.278 |

TABLE 35-continued

AUC$_{0-24\,hr}$ (mcg × hr/mL) Values Following Single Dose Administration (Fed and Fasted) and Repeat Doses of SA-ER

| Parameter | Phase | Visit | Statistic | 650 mg | 1950 mg | 2925 mg | 4875 mg | 6000 mg |
|---|---|---|---|---|---|---|---|---|
| AUC(0-24) (mcg × hr/mL) | Baseline (No Dose) | Day 1 | N | | 8 | 8 | 6 | 6 |
| | | | Mean | | 3.437 | 3.303 | 3.444 | 3.554 |
| | | | SD | | 0.380 | 0.631 | 0.606 | 0.329 |
| | | | Median | | 3.448 | 3.218 | 3.412 | 3.683 |
| | | | Min, Max | | 2.939, 4.173 | 2.404, 4.308 | 2.627, 4.152 | 2.968, 3.865 |
| | | | CV(%) | | 11.048 | 19.094 | 17.585 | 9.243 |
| Adjusted ADC(0-24) (mcg × hr/mL) | Repeat | Day 14 | N | | 8 | 8 | 4 | 6 |
| | | | Mean | | 2.407 | 3.069 | 7.442 | 6.740 |
| | | | SD | | 1.315 | 0.782 | 2.702 | 3.487 |
| | | | Median | | 2.349 | 3.250 | 7.361 | 6.026 |
| | | | Min, Max | | 0.594, 4.673 | 1.831, 4.022 | 4.788, 10.258 | 2.511, 11.816 |
| | | | CV(%) | | 54.625 | 25.470 | 36.308 | 51.728 |

NOTE:
Baseline values for single and repeat dose levels slightly vary because some patients who are included in one dose group for the single dose phase are included in a different dose group for the repeat dose phase. Therefore, the baseline means attempt to reflect the mean of the same patients that are being compared, and the mean changes slightly when you take some patients in or out.

The $T_{max}$ data (Table 36) show that food can have a substantial impact on peak levels, with the $T_{max}$ shifting much later when drug was administered with food. For the 4875 mg and 6000 mg dose levels, the shift was from 2.8 hours (Fasted) to 6.0 hours (Fed) and from 4.3 hours (Fasted) to 9.6 hours (Fed), respectively. Similar changes are observed at the other dose levels, with the exception of the lowest 650 mg dose. The change in peak concentration time and overall shape of the curves suggest that food may be an important factor in absorption of SA-ER.

The $T_{max}$ during repeat dosing shows a peak in the evening/nighttime (i.e., when the evening dose and the bedtime dose overlap). This timing is positive in terms of assuring an adequate level of sialic acid at night during peak protein synthesis.

TABLE 36

$T_{max}$ (Hours) Values Following Single Dose Administration (Fed and Fasted) and Repeat Doses of SA-ER

| Parameter | Phase | Visit | Statistic | 650 mg | 1950 mg | 2925 mg | 4875 mg | 6000 mg |
|---|---|---|---|---|---|---|---|---|
| Tmax (hr) | Baseline (No Dose) | Day 1 | N | 6 | 6 | 6 | 4 | 6 |
| | | | Mean | 17.964 | 16.644 | 13.344 | 17.004 | 9.372 |
| | | | SD | 5.456 | 8.530 | 9.356 | 1.953 | 8.317 |
| | | | Median | 20.017 | 19.975 | 16.033 | 16.042 | 9.958 |
| | | | Min, Max | 8.000, 23.700 | 0.000, 23.917 | 0.000, 24.000 | 16.000, 19.933 | 0.000, 20.000 |
| | | | CV(%) | 30.370 | 51.247 | 70.113 | 11.486 | 88.743 |
| | Single/Fasting | Day 2 | N | 6 | 6 | 6 | 4 | 6 |
| | | | Mean | 6.500 | 3.681 | 2.856 | 2.800 | 4.333 |
| | | | SD | 7.036 | 2.326 | 1.354 | 1.499 | 2.944 |
| | | | Median | 4.000 | 3.025 | 2.983 | 2.983 | 3.000 |
| | | | Min, Max | 1.000, 20.000 | 2.000, 8.000 | 1.000, 4.167 | 1.067, 4.167 | 2.000, 8.000 |
| | | | CV(%) | 108.240 | 63.205 | 47.426 | 53.549 | 67.937 |
| | Single/Fed | Day 7 | N | 6 | 6 | 5 | 4 | 5 |
| | | | Mean | 6.347 | 9.361 | 4.020 | 6.004 | 9.600 |
| | | | SD | 2.669 | 7.438 | 0.022 | 2.305 | 3.578 |
| | | | Median | 8.000 | 8.008 | 4.017 | 6.033 | 12.000 |
| | | | Min, Max | 2.000, 8.083 | 4.000, 24.000 | 4.000, 4.050 | 3.950, 8.000 | 4.000, 12.000 |
| | | | CV(%) | 42.049 | 79.458 | 0.541 | 38.391 | 37.268 |
| | Baseline (No Dose) | Day 1 | N | | 8 | 8 | 6 | 6 |
| | | | Mean | | 15.473 | 15.483 | 18.014 | 9.372 |
| | | | SD | | 7.799 | 8.653 | 3.321 | 8.317 |
| | | | Median | | 17.992 | 19.975 | 16.075 | 9.958 |
| | | | Min, Max | | 0.000, 23.700 | 0.000, 23.917 | 16.000, 24.000 | 0.000, 20.000 |
| | | | CV(%) | | 50.402 | 55.887 | 18.436 | 88.743 |
| | Repeat | Day 14 | N | | 8 | 8 | 4 | 6 |
| | | | Mean | | 19.479 | 16.513 | 13.038 | 17.353 |
| | | | SD | | 2.543 | 9.186 | 6.805 | 8.648 |
| | | | Median | | 20.000 | 20.000 | 14.033 | 20.000 |
| | | | Min, Max | | 16.000, 24.000 | 0.000, 24.000 | 4.083, 20.000 | 0.000, 24.000 |
| | | | CV(%) | | 13.056 | 55.632 | 52.192 | 49.838 |

NOTE:
Baseline values for single and repeat dose levels slightly vary because some patients who are included in one dose group for the single dose phase are included in a different dose group for the repeat dose phase. Therefore, the baseline means attempt to reflect the mean of the same patients that are being compared, and the mean changes slightly when you take some patients in or out.

The terminal half-life ($T_{1/2}$) of SA-ER at the three higher doses is similar (~3 hours) and modestly lengthened by food (Table 37). At the two lowest doses, the $T_{1/2}$ appears longer at 5.6 hours (650 mg) and 8.6 hours (1950 mg) but these values do not change consistently with food. It is possible that even though the endogenous SA was subtracted in these adjusted PK calculations, the $T_{1/2}$ values were still affected by the presence of an endogenous pool of SA of very similar size. The $T_{1/2}$ values for the baseline and repeat dosing are not meaningful given the absence of drug or the presence of repeated dosing, respectively.

mg/day dose. This is likely due to the longer PK exposure time of the 500 mg tablet, which led to an overlap between dose events (since dose was provided three times per day) and resulted in higher overall AUC levels at that dose.

Given that the SA levels achieved at all doses are well above the normal range, and that the PK curves are relatively steady over the 24 hour cycle, SA-ER tablets are performing as expected for an extended release formulation and should achieve levels of free SA that are expected to correct the deficiency of sialic acid levels and improve sialylation in the muscle of HIBM patients.

TABLE 37

$T_{1/2}$ (Hours) Values Following Single Dose Administration (Fed and Fasted) and Repeat Doses of SA-ER

| Parameter | Phase | Visit | Statistic | 650 mg | 1950 mg | 2925 mg | 4875 mg | 6000 mg |
|---|---|---|---|---|---|---|---|---|
| T ½ (hr) | Baseline (No Dose) | Day 1 | N | 2 | 2 | 4 | 3 | 4 |
| | | | Mean | 217.709 | 16.169 | 112.878 | 35.404 | 170.353 |
| | | | SD | 8.579 | 7.823 | 89.742 | 11.666 | 233.409 |
| | | | Median | 217.709 | 16.169 | 110.091 | 29.624 | 60.222 |
| | | | Min, Max | 211.643, 223.775 | 10.637, 21.701 | 34.520, 196.808 | 27.758, 48.831 | 40.862, 520.105 |
| | | | CV(%) | 3.940 | 48.382 | 79.504 | 32.950 | 137.015 |
| Adjusted T ½ (hr) | Single/Fasting | Day 2 | N | 4 | 6 | 6 | 4 | 6 |
| | | | Mean | 5.581 | 8.605 | 3.191 | 2.687 | 3.053 |
| | | | SD | 3.191 | 11.576 | 1.167 | 0.732 | 1.300 |
| | | | Median | 5.893 | 3.698 | 3.469 | 2.859 | 3.118 |
| | | | Min, Max | 2.144, 8.396 | 2.856, 32.123 | 1.123, 4.492 | 1.657, 3.371 | 1.440, 4.900 |
| | | | CV(%) | 57.175 | 134.528 | 36.580 | 27.254 | 42.587 |
| | Single/Fed | Day 7 | N | 3 | 6 | 5 | 4 | 5 |
| | | | Mean | 8.023 | 6.206 | 3.882 | 3.476 | 3.418 |
| | | | SD | 8.814 | 3.741 | 1.299 | 0.504 | 0.882 |
| | | | Median | 4.033 | 5.584 | 4.277 | 3.509 | 3.165 |
| | | | Min, Max | 1.909, 18.127 | 1.641, 11.499 | 1.715, 4.970 | 2.836, 4.050 | 2.337, 4.627 |
| | | | CV(%) | 109.858 | 60.276 | 33.470 | 14.495 | 25.795 |
| T ½ (hr) | Baseline (No Dose) | Day 1 | N | | 4 | 3 | 4 | 4 |
| | | | Mean | | 116.939 | 138.483 | 35.568 | 170.353 |
| | | | SD | | 116.552 | 90.258 | 9.531 | 233.409 |
| | | | Median | | 116.672 | 184.122 | 32.842 | 60.222 |
| | | | Min, Max | | 10.637, 223.775 | 34.520, 196.808 | 27.758, 48.831 | 40.862, 520.105 |
| | | | CV(%) | | 99.669 | 65.176 | 26.795 | 137.015 |
| Adjusted T ½ (hr) | Repeat | Day 14 | N | | 2 | 3 | 2 | 1 |
| | | | Mean | | 19.709 | 33.723 | 8.733 | 547.962 |
| | | | SD | | 8.741 | 35.060 | 1.797 | |
| | | | Median | | 19.709 | 25.351 | 8.733 | 547.962 |
| | | | Min, Max | | 13.528, 25.890 | 3.606, 72.211 | 7.463, 10.003 | 547.962, 547.962 |
| | | | CV(%) | | 44.352 | 103.966 | 20.572 | |

NOTE:
Baseline values for single and repeat dose levels slightly vary because some patients who are included in one dose group for the single dose phase are included in a different dose group for the repeat dose phase. Therefore, the baseline means attempt to reflect the mean of the same patients that are being compared, and the mean changes slightly when you take some patients in or out.

Pharmacokinetics Conclusions

The data show that SA-ER is absorbed and provides steady and significant drug levels over a period of 8-16 hours (depending on the dose level) and that there is definite inter-patient variability in the degree of SA absorption. The impact of food on AUC is complex, but in general, it appears that the $C_{max}$ is lowered and the $T_{max}$ is delayed with food. The AUC for the 6000 mg repeat dose was significantly improved with food. At higher dose levels, mean SA concentrations reached levels that exceeded normal SA levels by 2×-3×.

The data at the highest dose of 6000 mg/day did not show greater absorption than the 4875 mg/day dose level, which may be due to upward skewing of the data in the smaller 4875 mg single dose cohort in which two out of the four subjects had very high levels of free SA. During the single dose administration of 6000 mg/day, the PK parameters suggest a lower maximum drug level and a longer PK absorption curve as compared to the 4875 mg/day dose. In the repeat dosing period (and clinically more relevant setting), the 6000 mg/day dose performed similar to the 4875

Example 9

Combination Dose Canine Studies

Immediate Release Sialic Acid in Combination with Extended Release Sialic Acid (Tablets)

Preliminary data from canine study showed that Sialic Acid immediate release formulation (SA-API) was better absorbed and gave a higher peak earlier but was cleared faster. Thus, the purpose of the combination dose canine studies is to determine whether the addition of immediate release sialic acid to Extended Release Sialic Acid (SA-ER) can provide an increase in free and total SA levels.

Figure 25:
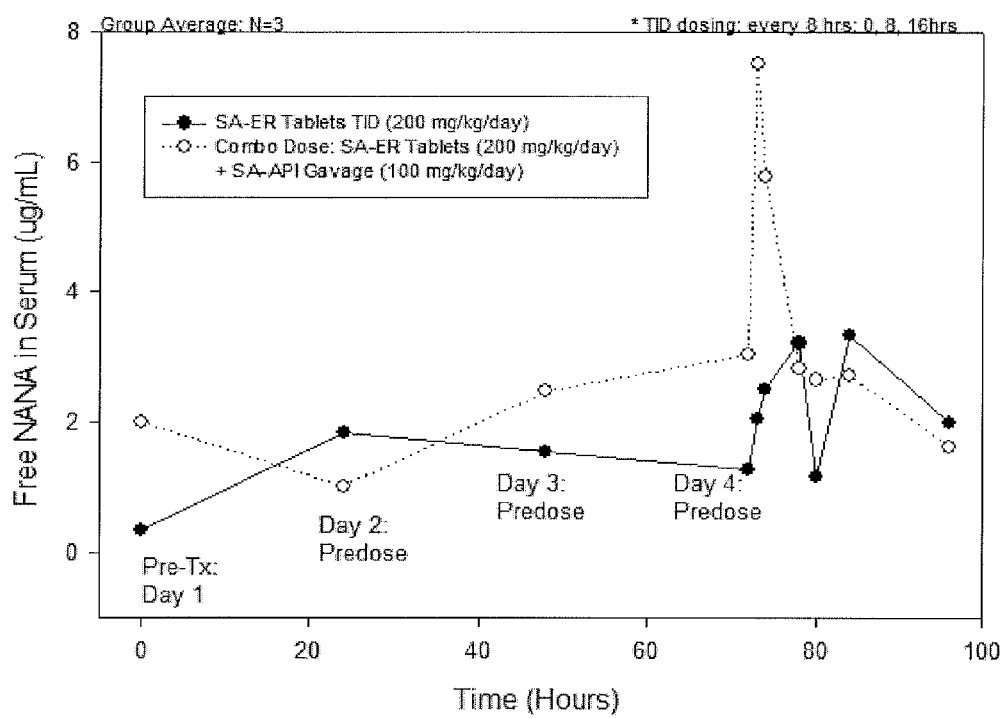
FIG. 25 shows a graph depicting free sialic acid concentrations in serum by 4 days of dosing sialic acid extended release formulation followed by 4 days of dosing sialic acid extended release formulation plus sialic acid immediate release formulation.

Study 1:

To determine whether the addition of immediate release sialic acid to SA-ER can provide an increase in total SA absorbed and mean free SA levels, two consecutive phases of dosing were conducted: SA-API (TID) was orally delivered for 4 days followed by 4 days of combination dose SA-API+SA-ER tablets (TID) in dogs. Phase 1: SA-ER tablets: 200 mg/kg/day for 4 days. Phase 2: SA-ER tablets (200 mg/kg/day) plus SA-API (100 mg/kg/day) for 4 days. Free sialic acid levels in serum was measured. The results were shown in FIG. 25.

Figure 26:
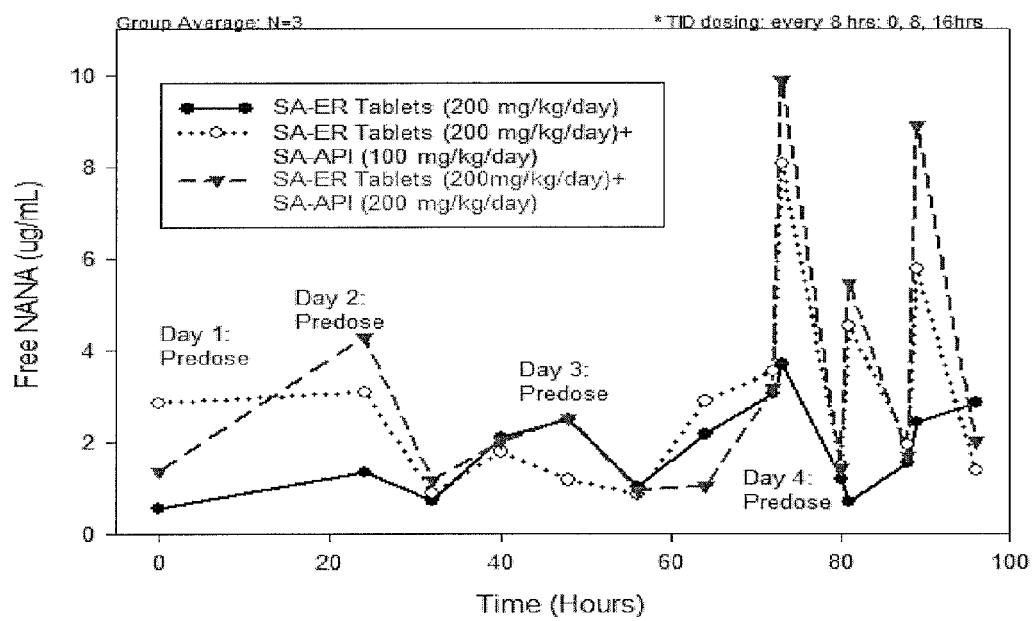
FIG. 26 shows a graph depicting free sialic acid concentrations in serum by 4 days of dosing sialic acid extended release formulation followed by 4 days of dosing sialic acid extended release formulation plus sialic acid immediate release formulation.

Study 2:

To determine whether the addition of immediate release sialic acid to SA-ER can reach steady state after a longer duration of dosing and provide an increase in total SA absorbed/mean free SA levels, three consecutive phases of dosing were conducted: SA-API (TID) was orally delivered for 4 days followed by 4 days of combination dose SA-API+ SA-ER tablets (TID) and measure free sialic acid levels in serum (dogs). Phase 1: SA-ER tablets: 200 mg/kg/day for 4 days. Phase 2: SA-ER tablets (200 mg/kg/day)+SA-API (100 mg/kg/day) for 4 days. Phase 3: SA-ER tablets (200 mg/kg/day)+SA-API (200 mg/kg/day) for 4 days. Free sialic acid levels in serum was measured on Days 4 and 8 and 12 (last day of each dosing phase). The results were shown in FIG. 26.

Area Under the Curve (AUC) for the end of each phase (Day 4: 0-24 hrs):

TID SA-ER Tablets 200 mg/kg/day: 37.8
TID SA-ER Tablets 200 mg/kg/day+SA-API 100 mg/kg/day: 66.4
TID SA-ER Tablets 200 mg/kg/day+SA-API 200 mg/kg/day: 90.4

CONCLUSION

Oral combination of SA-ER tablets and SA-API boosts overall absorption than SA-ER tablets alone. Thus, with 50% more drug in immediate release form, the free sialic acid levels in the serum can be doubled.

All publications and patent applications cited in this specification are incorporated herein by reference as if each individual publication or patent application were specifically and individually indicated to be incorporated by reference.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A method for treating a sialic acid deficiency in a human patient in need thereof comprising orally administering a solid dosage form two, three, or four times per day,
    wherein the solid dosage form is an extended release formulation comprising a blend of about 40% to 45% w/w of N-acetylneuraminic acid (NeuAc), or a pharmaceutically acceptable salt thereof;
    a hydrophilic polymer or hydrogel; wherein the hydrophilic polymer comprise one or more water-swellable, pH independent polymer selected from hypromellose, hydroxypropyl ethyl cellulose, hydroxypropyl cellulose, hydroxyethyl cellulose, and methyl cellulose; and the hydrogel is selected from polyhydroxyethyl methylacrylate (PHEMA), polyvinyl alcohol (PVA), polyvinylpyrrolidone (PVP), polyethylene oxide (PEO), or polyacrylamide (PA);
    an anionic, pH-dependent, gel-forming copolymer, wherein the anionic, pH-dependent, gel-forming copolymers comprise one or more alginate or salts thereof, or carboxymethyl cellulose or salts thereof; and
    a hydrocolloid polymer, wherein the hydrocolloid polymer is carrageenan; and
    wherein about 1950 mg to about 12000 mg of NeuAc or a pharmaceutically acceptable salt thereof, is administered per day;
    the method provides a therapeutically effective amount of NeuAc over a period of greater than about four hours and a steady plasma level of free NeuAc; and
    the method provides a mean plasma concentration of free NeuAc at steady state during dosing intervals that is at least about 50% higher than the mean plasma concentration of free NeuAc in the human patient before the administration of the NeuAc or a pharmaceutically acceptable salt thereof, and the mean plasma concentration of free NeuAc at steady state during the dosing intervals is at least about 0.16 mcg/ml.

2. The method of claim 1, wherein the solid dosage form further comprises an immediate release formulation containing N-acetylneuraminic acid (NeuAc), or a pharmaceutically acceptable salt thereof.

3. The method of claim 1, wherein the solid dosage form is administered three times per day.

4. The method of claim 3, which provides a therapeutically effective amount of NeuAc over a period of greater than about eight hours.

5. The method of claim 3, which provides a therapeutically effective amount of NeuAc over a period of greater than about twelve hours.

6. The method of claim 3, which provides a plasma concentration profile of free NeuAc at steady state such that the minimum plasma concentration of free NeuAc during the dosing interval is at least about 35% of the maximum plasma concentration during the dosing interval.

7. The method of claim 3, which provides an improved absorption profile when the extended release formulation is administered under fed conditions than being administered under fasting conditions.

8. The method of claim 7, wherein the mean $C_{max}$ determined at a fasted state is higher than the mean $C_{max}$ determined at a fed state.

9. The method of claim 7, wherein the mean $T_{max}$ determined at a fed state is higher than the mean $T_{max}$ determined at a fasted state.

10. The method of claim 3, wherein a total amount of about 3000 mg to about 12000 mg N-acetylneuraminic acid (NeuAc), or a pharmaceutically acceptable salt thereof, is administered per day.

11. The method of claim 1, wherein the sialic acid deficiency is a myopathy associated with sialic acid deficiency.

12. The method of claim 11, the myopathy associated with sialic acid deficiency is Hereditary Inclusion Body Myopathy (HIBM), Nonaka myopathy, and/or Distal Myopathy with Rimmed Vacuoles (DMRV).

13. The method of claim 1, wherein the extended release formulation is in a solid matrix form.

14. The method of claim 13, wherein the solid matrix form is compressed tablet.

15. The method of claim 4, which provides a therapeutically effective amount of NeuAc over a period of about eight to about ten hours.

16. The method of claim 4, which provides a therapeutically effective amount of NeuAc over a period of about eight to about twelve hours.

17. The method of claim 6, which provides a plasma concentration profile of free NeuAc at steady state such that the minimum plasma concentration of free NeuAc during the dosing interval is about 40% of the maximum plasma concentration during the dosing interval.

18. The method of claim 6, which provides a plasma concentration profile of free NeuAc at steady state such that the minimum plasma concentration of free NeuAc during the dosing interval is about 45% of the maximum plasma concentration during the dosing interval.

19. The method of claim 18, which provides a plasma concentration profile of free NeuAc at steady state such that the minimum plasma concentration of free NeuAc during the dosing interval is about 50% of the maximum plasma concentration during the dosing interval.

20. The method of claim 1, which provides a mean plasma concentration free NeuAc of at least about 0.20 mcg/ml at steady state during the dosing intervals.

21. The method of claim 10, wherein the total amount of NeuAc or a pharmaceutically acceptable salt thereof is about 6000 mg.

22. The method of claim 14, wherein the compressed tablet comprises about 500 mg of N-acetylneuraminic acid (NeuAc) in each unit dose.

* * * * *